(12) United States Patent  
Long et al.

(10) Patent No.: US 8,637,194 B2  
(45) Date of Patent: Jan. 28, 2014

(54) BIO-NANO POWER CELLS AND THEIR USES

(75) Inventors: Nathan R. Long, Conklin, MI (US); Jie Wang, Mt. Pleasant, MI (US); Hosam Gharib Abdelhady, Mt. Pleasant, MI (US)

(73) Assignee: Bio-Nano Power, LLC, Grand Rapids, MI (US)

( * ) Notice: Subject to any disclaimer, the term of this patent is extended or adjusted under 35 U.S.C. 154(b) by 632 days.

(21) Appl. No.: 12/584,232

(22) Filed: Sep. 2, 2009

(65) Prior Publication Data

US 2013/0330293 A1    Dec. 12, 2013

Related U.S. Application Data

(60) Provisional application No. 61/190,720, filed on Sep. 2, 2008.

(51) Int. Cl.  
*H01M 8/16* (2006.01)

(52) U.S. Cl.  
USPC .......................................................... 429/401

(58) Field of Classification Search  
USPC ............................. 525/451, 328.4; 429/2, 401  
See application file for complete search history.

(56) References Cited

U.S. PATENT DOCUMENTS

| | | |
|---|---|---|
| 5,378,628 A | 1/1995 | Gratzel et al. |
| 5,393,903 A | 2/1995 | Gratzel et al. |
| 5,958,783 A | 9/1999 | Josel et al. |
| 5,965,380 A | 10/1999 | Heller et al. |
| 5,981,286 A | 11/1999 | Herrmann et al. |
| 6,162,611 A | 12/2000 | Heller et al. |
| 6,294,281 B1 | 9/2001 | Heller |
| 6,329,161 B1 | 12/2001 | Heller et al. |
| 6,399,717 B1 | 6/2002 | Newkome et al. |
| 6,514,718 B2 | 2/2003 | Heller et al. |
| 6,531,239 B2 | 3/2003 | Heller |
| 6,605,200 B1 | 8/2003 | Mao et al. |
| 6,605,201 B1 | 8/2003 | Mao et al. |
| 6,676,816 B2 | 1/2004 | Mao et al. |
| 6,881,551 B2 | 4/2005 | Heller et al. |
| 7,018,735 B2 | 3/2006 | Heller |
| 7,090,756 B2 | 8/2006 | Mao et al. |
| 7,190,988 B2 | 3/2007 | Say et al. |
| 7,238,442 B2 | 7/2007 | Heller |
| 7,250,534 B1 | 7/2007 | Newkome |
| 7,368,190 B2 * | 5/2008 | Heller et al. .................. 429/2 |
| 8,092,662 B2 * | 1/2012 | Mao et al. ................ 204/403.12 |
| 2003/0096997 A1 | 5/2003 | Mao |
| 2004/0040840 A1 | 3/2004 | Mao |
| 2004/0099529 A1 | 5/2004 | Mao |
| 2006/0149067 A1 | 7/2006 | Mao |
| 2007/0007132 A1 * | 1/2007 | Mao et al. .................... 204/400 |
| 2007/0248850 A1 | 10/2007 | Heller |
| 2007/0298006 A1 | 12/2007 | Tomalia |

(Continued)

OTHER PUBLICATIONS

Ceroni et al. Progress in Polymer Science 30 (2005) p. 453-573.*

(Continued)

*Primary Examiner* — Patrick Ryan  
*Assistant Examiner* — Lucas J O'Donnell

(57) ABSTRACT

The present invention concerns bio-nano power cells and methods of their manufacture and use. More particularly, the present invention relates to the preparation of bio-nano power cells that are biocompatible and capable of producing flash, intermittent, or continuous power by electrolyzing compounds in biological systems.

28 Claims, 15 Drawing Sheets

(56) References Cited

U.S. PATENT DOCUMENTS

| | | | |
|---|---|---|---|
| 2008/0044721 A1* | 2/2008 | Heller et al. | 429/43 |
| 2009/0099434 A1 | 4/2009 | Liu et al. | |
| 2010/0288634 A1* | 11/2010 | Mao et al. | 204/403.14 |
| 2011/0303538 A1* | 12/2011 | Mao et al. | 204/403.14 |

OTHER PUBLICATIONS

"Dendrimers based on ruthenium(II) and osmium(II) polypyridine complexes and the approach of using complexes as ligands and complexes as metals", Serroni et al, Chem. Soc. Rev., 2001, 30, 367-375.*

F. Vogtle, et al., Chem. Eur. J., 1997, 3 (5), pp. 706-712.

* cited by examiner

BIO-NANO POWER CELLS AND THEIR USES

CROSS REFERENCE TO RELATED APPLICATION AND PRIORITY CLAIM

This application claims priority from U.S. Provisional Application 61/190,720, filed on Sep. 2, 2008, the disclosure thereof is hereby incorporated by reference.

BACKGROUND OF THE INVENTION

1. Field of the Invention

The present invention concerns nano-scale power cells and power cell aggregates (bio-nano power cells or BNPC) that derive power from compounds found in biological systems and methods of their manufacture and use. Bio-nano power cells include bio-nano sensors, bio-nano fuel cells, bio-nano batteries, biosensors, biofuel cells and biobatteries. More particularly, the present invention relates to the preparation of bio-nano power cells that are biocompatible and capable of producing flash, intermittent, or continuous power by electrolyzing compounds found in biological systems and methods of their manufacture and use.

2. Description of Related Art

Producing flash, intermittent, or continuous electrical power from energy sources available in biological systems has long been desired. As availability of traditional energy systems diminish, compounds and systems that efficiently convert energy rich compounds found in biological systems offer seemingly unlimited potential for energy production. Also, compounds and systems that efficiently generate electrical power in situ are needed to power smaller, integrated medical devices and to power on-demand, targeted delivery of pharmaceuticals. These compounds and systems, while highly desired, have been difficult to prepare and implement for a variety of reasons.

Various systems to meet this need have been attempted. Those that are useful as a component of this invention are discussed below.

Enzyme Based Redox Mediators

Electrochemical sensors, based on enzyme mediators, are widely used in the detection of analytes in agricultural and biotechnological, clinical, and environmental applications. The electro-oxidation or electro-reduction of the enzyme is often facilitated by the presence of a redox mediator that assists in the electrical communication between the working electrode and the enzyme. When the substrate of the enzyme is electro-oxidized, the redox mediator transports electrons from the substrate-reduced enzyme to the electrode; when the substrate is electro-reduced, the redox mediator transports electrons from the electrode to the substrate-oxidized enzyme.

Transition metal complexes, developed by Michael Grätzel (e.g., described in U.S. Pat. Nos. 5,378,628; 5,393,903, the disclosures of which are hereby incorporated by reference) and developed by Adam Heller (e.g., described in U.S. Pat. Nos. 5,965,380; 6,162,611; 6,329,161; 6,514,718; 6,605,200; 6,605,201; 6,676,816; 6,881,551; and 7,090,756, and US Published Patent Applications 20030096997; 20040040840; 20040099529; 20060149067; 20070007132; and 20090099434, the disclosures of which are hereby incorporated by reference) can be used as redox mediators in enzyme based electrochemical sensors. The following formula depicts these entities.

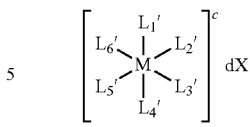

Formula A

The metal (M) in Formula A can be various metals, including iron, cobalt, ruthenium, osmium or vanadium. The ligands ($L_1'$, $L_2'$, $L_3'$, $L_4'$, $L_5'$, $L_6'$) can be various chelants, including monomeric, cyclic, bidentate, or polymeric entities which form a chelate with (M). c is an integer selected from −1 to −5, 0 or +1 to +5 indicating a negative, neutral or positive charge. X represents a counter ion and d is an integer from 1 to 5 representing the number of counter ions. Formula A is charge neutral. These biosensor can be functionalized by coupling targeting moieties, such as glucose oxidase, lactate oxidase, and other moieties to form amperometric biosensors for the measurement of glucose, lactate and other analytes, respectively.

Redox centers, for example $Os^{2+/3+}$, can be coordinated with five heterocyclic nitrogens and an additional ligand such as, for example, a chloride anion. An example of such a coordination complex includes: two bipyridine ligands which form stable coordinative bonds; the pyridine of poly(4-vinylpyridine) which forms a weaker coordinative bond; or a chloride anion which forms the least stable coordinative bond.

Alternatively, redox centers, such as $Os^{2+/3+}$, can be coordinated with six heterocyclic nitrogen atoms in its inner coordination sphere. The six coordinating atoms are preferably paired in the ligands; for example, each ligand is composed of at least two rings. Pairing of the coordinating atoms can influence the potential of an electrode used in conjunction with redox polymers.

Metal complexes with charged linkers for use as luminescent marker groups in an immunoassay are described in U.S. Pat. Nos. 5,958,783 and 5,981,286, illustrating the use of metal ions with ligands that have reactive or activatable functional groups.

Transition Metal Complex Polymers [TMC Polymers]

Transition metal complexes can be directly or indirectly attached to a polymeric backbone, depending on the availability and nature of the reactive groups on the complex and the polymeric backbone. For example, the pyridine groups in poly(4-vinylpyridine) or the imidazole groups in poly(N-vinylimidazole) are capable of acting as monodentate ligands and thus can be attached to a metal center (M) directly. Alternatively, the pyridine groups in poly(4-vinylpyridine) or the imidazole groups in poly(N-vinylimidazole) can be quaternized with a substituted alkyl moiety having a suitable reactive group, such as a carboxylate function, that can be activated to form a covalent bond with a reactive group, such as an amine, of the transition metal complex. Use of these TMC to analyze various analytes has been tried.

Voltages

Typically, for analysis of glucose, the potential at which the working electrode, coated with the redox polymer, is poised negative at about ±250 mV vs. SCE (standard calomel electrode). Preferably, the electrode is poised negative at about +150 mV vs. SCE. Poising the electrode at these potentials reduces the interfering electro-oxidation of constituents of biological solutions (such as, for example, urate, ascorbate and acetaminophen). The potential can be modified by altering the ligand structure of the complex of Formula A.

The redox potential of a redox polymer, as described herein, is related to the potential at which the electrode is poised. Selection of a redox polymer with a desired redox potential allows tuning of the potential at which the electrode is best poised. The redox potentials of a number of the redox polymers described herein are negative at about +150 mV vs. SCE and can be negative at about +50 mV vs. SCE to allow the poising of the electrode potentials negative at about +250 mV vs. SCE and preferably negative at about +150 mV vs. SCE.

The strength of the coordination bond can influence the potential of the redox centers in the redox polymers. Typically, the stronger the coordinative bond, the more positive the redox potential. A shift in the potential of a redox center resulting from a change in the coordination sphere of the transition metal can produce a labile transition metal complex. For example, when the redox potential of an $Os^{2+/3+}$ complex is downshifted by changing the coordination sphere, the complex becomes labile. Such a labile transition metal complex may be undesirable when fashioning a metal complex polymer for use as a redox mediator and can be avoided through the use of weakly coordinating multidentate or chelating heterocyclics as ligands.

Voltages that different transition metal complexes (TMC) can generate are discussed in various patents (for example U.S. Pat. Nos. 6,605,200; 6,605,201; 6,676,816; 6,881,551; 7,090,756, and US Published Patent Applications 20030096997; 20040040840; 20040099529; 20060149067; 20070007132; and 20090099434, the disclosures of which are hereby incorporated by reference).

Some examples of TMC of Formula A are shown below:

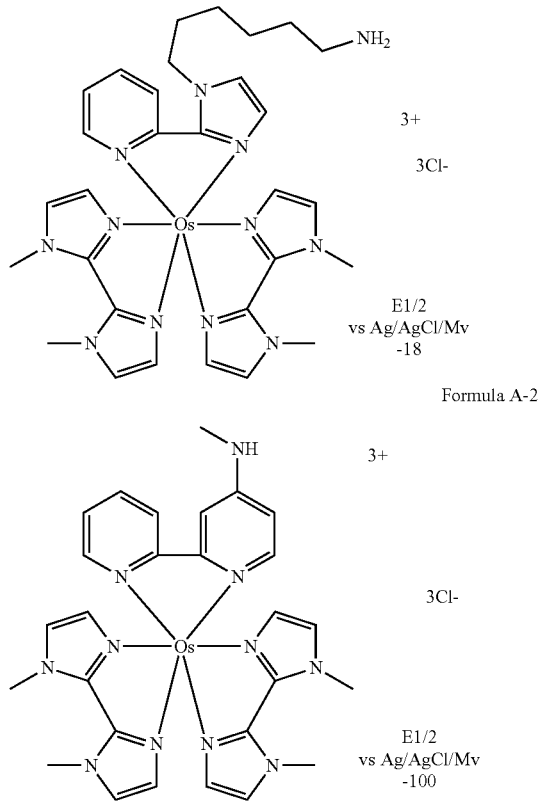

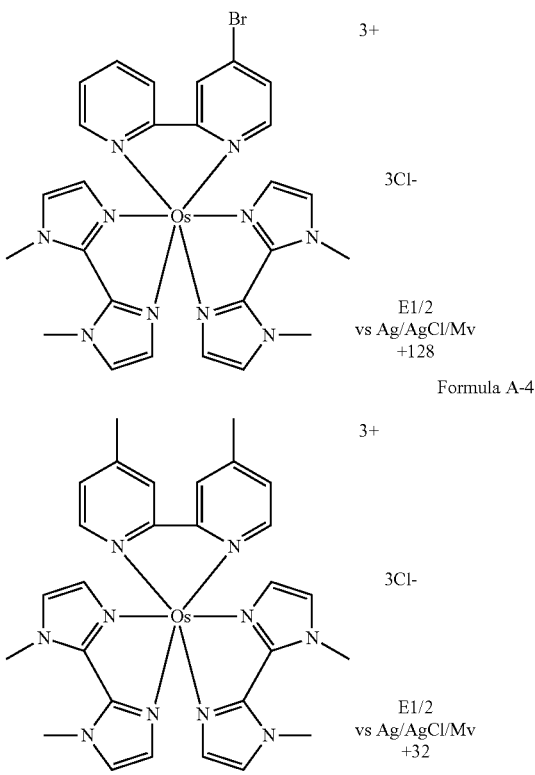

Biosensors

An example of the components of a functionalized transition metal complex (TMC) is shown below.

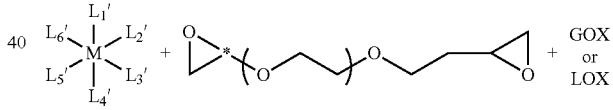

It is the reaction product of osmium hexachloride, bipyridine, polyimidazole, and polyethylene glycol diglycidyl ether. Either glucose oxidase (GOX) or lactate oxidase (LOX) can be added to create a biosensor complex for the measurement of glucose or lactate, respectively. An example of such biosensors is shown in FIG. 1. TMC Polymers, discussed above, improve electron transport; when used the biosensors are called "wired enzyme" biosensors. These polymers can be used for biosensors as described as examples in U.S. Pat. Nos. 5,965,380; 6,162,611; 6,329,161; 6,514,718; 6,881,551 and 7,190,988.

Biofuel Cells

Transition metal complexes described above in Formula A can also be used for the preparation of biological fuel cells (e.g., U.S. Pat. Nos. 6,294,281; 6,531,239; 7,018,735; 7,238,442 and US Published Patent Applications 20070248850 and 20080044721). The use of anode enzymes (e.g., oxidase or dehydrogenase), use of cathode enzymes (e.g., laccase, ascorbate oxidase, creuloplamine or bilirubin oxidase) are also discussed.

Issues of Biosensors

While the biosensors described by Adam Heller, et al. in the patents listed above generate good voltages, the practical utility of these compounds is restricted because of bio-fouling. Generally, a separate membrane layer or other layer is needed to have adequate biocompatibility for use (see FIG. 1) and this greatly reduces the utility of these transition metal complexes.

Clearly, it would be advantageous to increase the biocompatibility of such a system.

Dendritic Polymers

A wide range of dendritic polymers have been disclosed (see *Dendrimers and Other Dendritic Polymers*, eds. J. M. J. Fréchet, D. A. Tomalia, pub. John Wiley and Sons, 2001). Among the possible dendritic polymers are dendrimers such as PAMAM dendrimers [poly(amidoamine)], PEI dendrimers [poly(ethyleneimine)], PEHAM dendrimers [poly(etherhydroxylamine)]. Also included as dendritic polymers are dendrons, dendrigrafts, tectodendrimers, comb-branched polyethers and others known as dendritic polymers such as polylysine and hyperbranched polyethers.

Other dendritic polymers are hyper-branched polymers, developed by Donald A. Tomalia and others, where a core is surrounded with branching atoms that provide unique solubility, biocompatibility, and/or structural properties. These polymers do not have the complete regularity of the dendrimers but are useful in many applications.

Nano-scale technologies offer considerable promise to create power cells with the necessary biocompatibility for nano-scale molecules and larger polymeric compounds without requiring secondary fabrication steps. Recent advances, by Tomalia, et al. in US Published Patent Application 20070298006 (which disclosure is hereby incorporated by reference), illustrate how dendritic polymers can add biocompatible groups to the surface of nano-scale molecules and polymeric compounds. (See FIG. 2 for a depiction of these dendrimers.) Particularly described are the PEHAM dendrimers. Also discussed are ring-opening reactions to prepare branched polymer systems, explanations of how steric effects impact design of synthetic compounds at the nanoscale level, (i.e. 1-100 nm) and inherent difficulties in the synthesis of dendrimers.

Dendritic bipyridines with reactive sites have been synthesized by Issberger and Vogtle, et al. and used to make ruthenium chelates. [See Jörg Issberger, Fritz Vogtle, Luisa DeCola, Vincenzo Balzani, *Chem Eur., J.,* 1997, 3 (5).]

Dendritic materials for enhanced performance of energy storage devices have been prepared by Newkome and Moorefield in U.S. Pat. No. 6,399,717 and Newkome in U.S. Pat. No. 7,250,534. These patents illustrate the use of dendritic building blocks to create metallo-based (macro) molecules for magneto resistive disk drive heads.

Dendritic Polymers with Carried Materials

These dendritic polymers can be used for a wide variety of applications, including those that require useful materials to be carried within the interstitial spaces of the dendritic polymer and/or on its surface for many uses, including but not limited to, for chemotherapies, controlled release, carried material delivery, drug releasing devices, polyvalent pharmaceutical moieties, targeted therapies, diagnostics, and therapeutics. Among those carried materials that offer great utility are agricultural materials, antibodies, antibody fragments, aptamers, bioactive agents, biological response modifiers, diagnostic opacifiers, fluorescent moieties, pharmaceuticals, scavenging agents, agricultural materials, hormones, immune-potentiating agents, pesticides, bioactive agents, signal absorbers, signal generators, metal ions, pesticides, pharmaceuticals, radionuclides, scavenging insecticides, bioactive agents, toxins, and many other materials. Any material can be carried within the dendritic polymer so long as it does not appreciably disturb the physical structure of the polymer and is compatible with it. The material may be encapsulated or surface attached as explained in US Published Patent Application 20070298006. When these materials are present with a dendrimer then it is termed a conjugate. Thus FIG. 2A with a carried material is a dendrimer conjugate; FIG. 2B with a carried material is a dendrimer dimer aggregate conjugate.

The surface groups can be modified to have a targeting receptor moiety present and solubilizer groups to aid in the delivery of the carried material.

Issues with Dendritic Polymers

While dendritic polymers offer significant potential, delivery of carried material is not "on-demand" but rather involves changes in pH or slow diffusion to release the carried material at the desired site.

Clearly, it would be advantageous to have a system that could meet the needs for on-demand delivery of carried materials.

BRIEF SUMMARY OF THE INVENTION

The BNPC moieties of this invention are shown by the following formula:

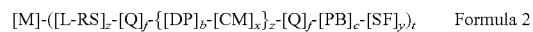

$$[M]\text{-}([L\text{-}RS]_z\text{-}[Q]_f\text{-}\{[DP]_b\text{-}[CM]_x\}_z\text{-}[Q]_f\text{-}[PB]_c\text{-}[SF]_y)_t \quad \text{Formula 2}$$

wherein:
[M] is an iron, cobalt, ruthenium, osmium, or vanadium metal ion;
[L-RS] means a ligand or groups of ligands, including monodentate, bidentate, and tridentate ligands (as shown by Formula 1 hereinbelow) that have a Reactive Site [RS];
z is independently 0 or from 1 to 6;
[Q] means a linker moiety having at least 2 reactive sites and if more that 1 [Q] is present, they may be the same or different moieties;
f is independently 0 or from 1 to the number of [RS];
[DP] means Dendritic Polymer and has all the characteristics of such Dendritic Polymers as discussed herein having the ability to react with [RS] and the number of generations, G, of [DP], counting as concentric branch cell shells outward from the core [TMC] and usually counting sequentially from the core, where G=from 0 to the de Gennes dense packing of the surface or N-SIS effects; preferably the surface groups on the [DP] are biocompatible;
b is independently 0 or from 1 to at least the number of [L-RS] present;
[CM] means carried material;
x means 0 or an integer from 1 to 4000;
[PB] means polymer backbone;
c is independently 0 or from 1 to 6;
[SF] means the surface functionality groups that can either react with or associate with an enzyme, analyte, cross-linking group, [CM], or be inert;
y means from 1 to the total number of possible surface groups available, and if greater than 1 may be the same or different moiety; and
t is from 1 to 6, provided that when t is less than 6, the other available sites on [M] may be [L], H, F, Cl, Br, I, CN, SCN, OH, $H_2O$, $NH_3$, alkylamine, dialkylamine, trialkylamine, alkoxy, heterocyclic compounds or polymer backbones that do not have reactive sites; and provided that for at least one entity where t is 1 or more, all z are at least 1 and b is 1.

The present invention concerns bio-nano power cells and methods of their manufacture and use. More particularly, the present invention relates to the preparation of bio-nano power cells that are biocompatible and capable of producing flash, intermittent, or continuous power by electrolyzing compounds in biological systems.

DETAILED DESCRIPTION OF THE INVENTION

Figure 1:
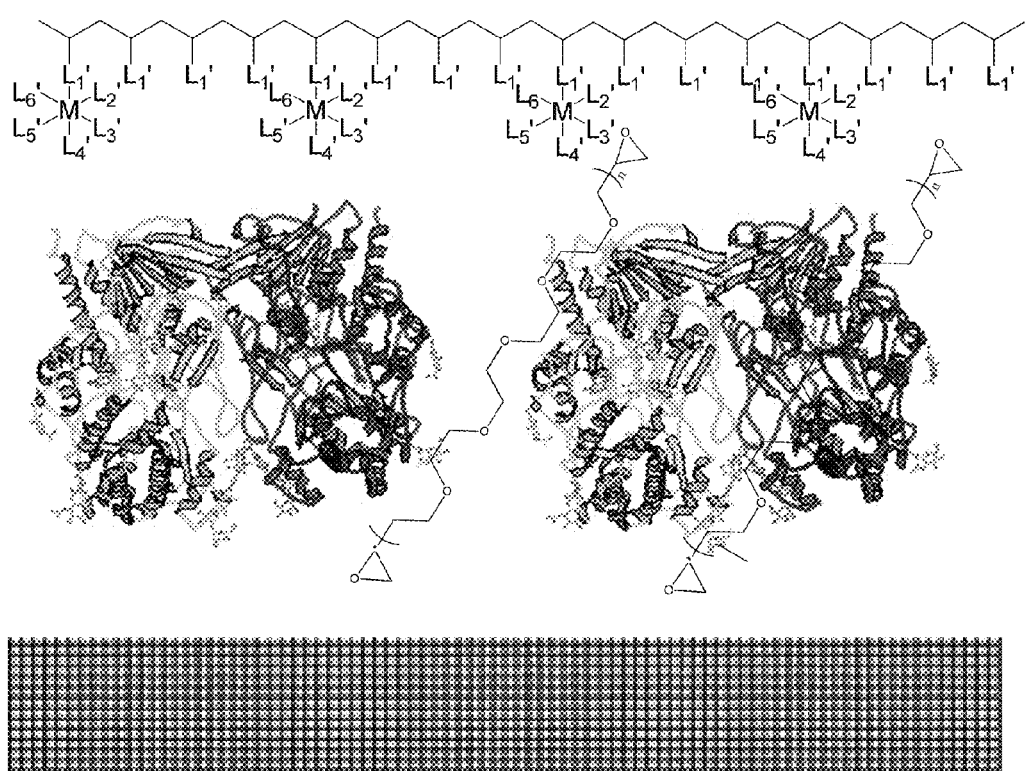
FIG. 1 illustrates a known biosensor with membrane.
Figure 2A:
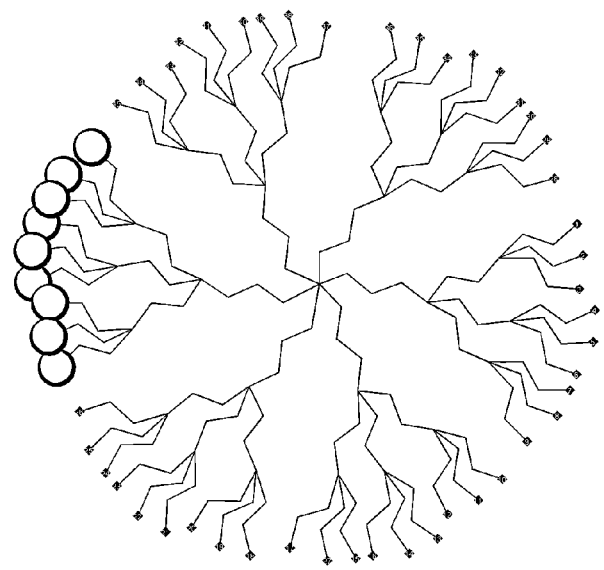
FIG. 2A is a dendrimer; 2B is a dendrimer dimer aggregate where two dendrimers are covalently joined.
Figure 2B:
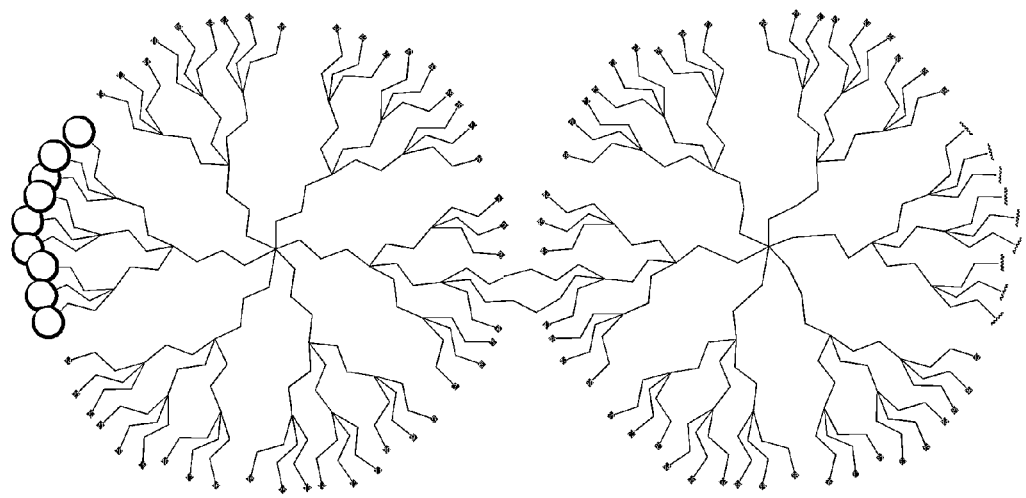
FIG. 2 illustrates known dendritic polymers with a few surface groups modified.

Certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

It is understood that the terminology used herein is for the purpose of describing particular embodiments only and is not intended to be limiting. As used in this specification, the singular forms "a", "an", and "the" include plural referents unless the content clearly indicates otherwise.

GLOSSARY

The following terms as used in this application are to be defined as stated below and for these terms, the singular includes the plural.

AEP means 1,(2-aminoethyl)piperazine

Alkyl means a saturated, straight-chain or branch-chain hydrocarbon, including when it is part of another moiety such as alkoxy, alkylthio, cycloalkyl, cycloalkoxy, heterocycloalkyl or similar moieties or a moiety substituted by an alkyl such as alkylaryl or heteroalkyl; examples are methyl, ethyl, iso-propyl, t-butyl, neopentyl, and others; the number of carbon atoms present in any one alkyl group is from about $C_1$-$C_{100}$, preferably from about $C_1$-$C_{50}$ and most preferred from about $C_1$-$C_{25}$ Alkenyl means a unsaturated, straight-chain or branch-chain hydrocarbon having at least one, but often more than one, C=C bond; including when part of a substitution on another moiety such as cycloalkenyl, arylalkenyl, vinylcycloalkyl, cycloalkoxyalkenyl; examples are ethenyl, 1-propenyl, 2-propenyl, 1-butenyl, 2-methyl-1-propenyl, and the like; the number of carbon atoms present in any one alkenyl group is from about $C_2$-$C_{100}$, preferably from about $C_2$-$C_{50}$ and most preferred from about $C_2$-$C_{25}$ Alkynyl means a unsaturated, straight-chain or branch-chain hydrocarbon having at least one, but often more than one, C≡C bond; including when part of a substitution on another moiety such as cycloalkynyl; arylalkynyl; cycloalkoxyalkynyl; examples are ethynyl, 1-propynyl, 2-propynyl, 1-butyryl, 2-methyl-1-propynyl, and the like; the number of carbon atoms present in any one alkynyl group is from about $C_2$-$C_{100}$, preferably from about $C_2$-$C_{50}$ and most preferred from about $C_2$-$C_{25}$ Aptamer means a specific synthetic DNA or RNA oligonucleotide that can bind to a particular target molecule, such as a protein or metabolite Aryl means any number of carbon atoms containing an aromatic moiety and can be from about $C_5$-$C_{100}$ and may be substituted with one or more alkyl (optionally substituted), alkenyl (optionally substituted), alkynyl (optionally substituted), halo (Cl, Br, F), hetero atoms in the ring (such as N, O, S, P, B), azides, and others (such as those in the present examples and taught in this specification)

BAA means bis(allyl)amine or diallylamine

Biological Fluid means any body fluid or body fluid derivative in which a desired analyte can be measured, for example, blood, interstitial fluid, plasma, dermal fluid, sweat, and tears BiPy means bipyridine (2,2'-dipyridyl)

BiPyDA means bipyridine-di(amino)

BiPyDADMe means 4,4'-bis(dimethylamino)-2,2'-bipyridine

BiPyDAE means bipyridine-di(aminoethane)

BiPyDBr means bipyridine-dibromo

BiPyDC9 means 4,4'-dinonyl-2,2'-bipyridyl (4,4'-dinonyl-2,2'-dipyridyl)

BiPyDCBOA3 means 2,2'-bipyridine-3,3'-dicarboxylic acid

BiPyDCBOA4 means 2,2'-bipyridine-4,4'-dicarboxaldehyde

BiPyDCBOA5 means 2,2'-bipyridine-5,5'-dicarboxylic acid

BiPyDCBOX means 2,2'-bipyridine-5,5'-dicarboxylic acid

BiPyDCBOX means 4,4'-dicarboxy-2,2'-bipyridine

BiPyDCHMDA means bipyridine-di(carboxy-hexamethylenediamine)

BiPyDC1 means 4,4'-dichloro-2,2'-bipyridine
BiPyDCPIPZ means bipyridine-di(carboxy-piperazine)
BiPyDCTMDA means bipyridine-di(carboxy-trimethylene-diamine)
BiPyDDEDAOP means bipyridine-di(diethyl-diamino-oxo-pentanoate
BiPyDHMDA means bipyridine-di(hexamethylenediamine)
BiPyDMe means 4,4'-dimethyl-2,2'-bipyridine (4,4'-dimethyl-2,2'-dipyridyl)
BiPyDOH means 2,2'-bipyridine-3,3'-diol
BiPyDOMe means 4,4'-dimethoxy-2,2'-bipyridine
BiPyDPH means 4,4'-diphenyl-2,2'-bipyridyl (4,4'-diphenyl-2,2'-dipyridyl)
BiPyDt-Bu means 4,4'-di-tert-butyl-2,2'-bipyridyl
BiPyDTMDA means bipyridine-di(trimethylenediamine)
BiPynO means 2,2'-bipyridyl-N-oxide
BiPynO1NO2 means 4'-nitro-2,2'-bipyridine-N-oxide
BiPynO2NO2 means 4,4'-dinitro-2,2'-bipyridine-N-oxide
BiPynOnO means 2,2'-bipyridine-N,N'-dioxide (2,2'-dipyridyl-N,N'-dioxide)
BNPC means bio-nano power cells as shown by Formula 2 (also called dendritic power cells)
BOC means tert-butoxycarbonyl
[BR] means a branch cell, which when more than 1 is present may be the same or different, and is a part of [DP] as described in US 2007-0298006
Counter Electrode means both a) counter electrodes and b) counter electrodes that also function as reference electrodes (i.e., counter/reference electrodes), unless otherwise indicated
DBA means dibenzylamine
DCM means dichloromethane
DDEDA means dodecylethylenediamine (1,12-diamin-ododecane)
DEA means diethylamine
DEIDA means diethyliminodiacetate
Dendritic Conjugate means a Dendritic Polymer having a carried material present
Dendritic Polymer or [DP] means any repeating dendritic structure polymer such as PAMAM dendrimers, PEHAM dendrimers, PEI dendrimers, dendrons, dendrigraft polymers, tectodendrimers, hyperbranched polymers or other similar dendritic structures as described in *Dendrimers and Other Dendritic Polymers*, eds. J. M. J. Fréchet, D. A. Tomalia, pub. John Wiley and Sons, 2001
DETA means diethylenetriamine
DI water means deionized water
DMF means dimethylformamide
DMI means dimethylitaconate (dimethyl 2-methylenesuccinate)
DMSO means dimethylsulfoxide
DNA or RNA or nucleic acids means synthetic or natural, single or double stranded DNA or RNA or PNA (phosphorous nucleic acid) or combinations thereof or aptamers, preferably from 4 to 9000 base pairs or from 500 D to 150 kD
DO3A means 1,4,7,10-tetraazacyclododecane-1,4,7,10-tris(acetic acid)
DOTA means 1,4,7,10-tetraazacyclododecane-1,4,7,10-tetra(acetic acid)
DTPA means diethylenetriaminepentaacetic acid
DTT means dithiothreitol
EA means ethylamine
EDA means ethylenediamine
EDTA means ethylenediaminetetraacetic acid
Electrochemical Sensor means a device configured to detect the presence of or measure the concentration or amount of an analyte in a sample via electrochemical oxidation or reduction reactions. These reactions typically can be transduced to an electrical signal that can be correlated to an amount or concentration of analyte.
Electrolysis means the electro-oxidation or electro-reduction of a compound either directly at an electrode or via one or more electron transfer agents (e.g., redox mediators or enzymes).
EPC means ethyl-N-piperazinecarboxylate
Et means ethyl
EtOH means ethanol
[EX] means extender, which if greater than 1 may be the same or a different moiety as part of [DP] as described in US Published Appln. 2007-0298006
Fe2BiPyDA means iron bis(BiPy)(di-amino)
$FeCl_2\text{-}4H_2O$ means iron(II) chloride tetrahydrate
FITC means fluorescein isothiocyanate
G means a dendrimer generation, which is indicated by the number of concentric branch cell shells surrounding the core (usually counted sequentially from the core)
GOX means glucose oxidase
g means gram(s)
h means hour(s)
Halo means fluoro, chloro, bromo, or iodo atom, ion or radical
HCl mean hydrochloric acid
HEDA means (2-hydroxyethyl)ethylenediamine
HMDA means hexamethylenediamine (amino-hexylamine)
[IF] means interior functionality of a [DP] as described in US 2007-0298006
IMAE means 2-imidazolidyl-1-aminoethane
IR means infrared spectroscopy
$K_2OsCl_6$ means potassium hexachloroosmate(IV)
KOH means potassium hydroxide; used as 85% pellets from Aldrich, powdered before use
L means liter(s)
LOX means lactate oxidase
mA means milliamphere(s)
MEA means monoethanolamine
MeOH means methanol
mg means milligram(s)
mins. means minutes
MIPIEP means methylisopropyliminoethylpiperazine
mL means milliliter(s)
N-SIS means nanoscale sterically induced stoichiometry
Oligonucleotides means synthetic or natural, single or double stranded DNA or RNA or PNA (peptide nucleic acid) or combinations thereof or aptamers, preferably from 4 to 100 base pairs
Orthogonal Chemistry means the chemical transformations that may be performed either in parallel or in sequence on a multi-functional reagent or substrate without cross-reactions or interference by other components of the reactants
Os2BiPyDA means osmium bis(BiPy)(diamino)
Os2BiPyDAE means osmium bis(BiPy)(diaminoethane)
Os2BiPyDCHMDA means osmium bis(BiPy)(dicarboxy-hexamethylenediamine)
Os2BiPyDCPIPZ means osmium bis(BiPy)(dicarboxy-piperazine)
Os2BiPyDCTMDA means osmium bis(BiPy)(dicarboxy-trimethylenediamine)
Os2BiPyDEDAOP means osmium bis(BiPy)(diethyl-diamino-oxopentanoate)
Os2BiPyDCHMDA means osmium bis(BiPy)(dicarboxy-hexamethylenediamine)
Os2BiPyDCTMDA means osmium bis(BiPy)(dicarboxy-trimethylenediamine)
Os3BiPyDA means osmium tris(BiPy)(diamino)

Os3BiPyDAE means osmium tris(BiPy)(diaminoethane)
Os3BiPyDCHMDA means osmium tris(BiPy)(dicarboxy-hexamethylenediamine)
Os3BiPyDCPIPZ means osmium tris(BiPy)(dicarboxy-piperazine)
Os3BiPyDCTMDA means osmium tris(BiPy)(dicarboxy-trimethylenediamine)
Os3BiPyDDEDAOP means osmium tris(BiPy)(diethyl-diamino-oxopentanoate)
Os3BiPyDCHMDA means osmium tris(BiPy)(dicarboxy-hexamethylenediamine)
Os3BiPyDCTMDA means osmium tris(BiPy)(dicarboxy-trimethylenediamine)
PAMAM means poly(amidoamine), including linear and branched polymers or dendrimers with primary amine terminal groups
[PB] means polymer backbone and can be any linear polymer that has 1 or more groups that can react with [SF], [DP] or [RS]
PCR means polymerase chain reaction
PEGDE means poly(ethylene glycol (400) diglycidyl ether) (di-epoxide)
PEHAM means poly(etherhydroxylamine) dendrimer as described in US Published Patent Application 20070298006
PEI means poly(ethyleneimine)
Percent or % means by weight unless stated otherwise
PETAE means pentaerythritol tetraallyl ether
PETAZ means pentaerythritol tetraazide
PETGE means pentaerythritol tetraglycidyl ether
PETriAE means pentaerythritol triallyl ether
PETriGE means pentaerythritol triglycidyl ether
PGA means poly(glycidyl) aniline
PGE means poly(glycidyl)ether
PIPZ means piperazine or diethylenediamine
PPI means poly(propyleneimine)dendrimer
PVAH means polyvinylanhydride
PVI means poly(vinylimidazole)
PVIPVA means poly(vinylimidazole-polyvinylaniline
PVPBAc means polyvinylpyridine-butyl acetate
PVPCEA means polyvinylpyridine-(butyl acetate+ethylenediamine)
PVPCTREN means polyvinylpyridine-(butyl acetate+tris(2-aminoethyl)amine)
PVPy means polyvinylpyridine
PVPyBMAc means poly(4-vinylpyridine-co-butyl methacrylate)
PVPyPVA means poly(vinypyridine-polyvinylaniline
PyMIM means (methyl-pyridyl)imidazole
PyMIMHAm means 1-(6-aminohexyl)-2-(6-methyl-2-pyridyl) imidazole
PyMIMHPHI means 2-(6-methyl-2-pyridyl)-1-(6-(phthalimido) hexyl)imidazole
Reactive Group means functional group of a first molecule that is capable of reacting with another compound to couple at least a portion of that other compound to the first molecule. Reactive groups include, but are not limited to, carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzotriazolyl, or aryl substituted by electron-withdrawing groups such as sulfo, nitro, cyano, or halo groups; or carboxylic acids activated by carbodiimides.
Redox Mediator means an electron transfer agent for carrying electrons between an analyte or an analyte-reduced or analyte-oxidized enzyme and an electrode, either directly, or via one or more additional electron transfer agents.
Reference Electrode means both a) reference electrodes and b) reference electrodes that also function as counter electrodes (i.e., counter/reference electrodes), unless otherwise indicated.
[RS] means reactive site functionality on [L] and if greater than 1 may be the same or different moiety
RT means ambient temperature or room temperature, about 20-25° C.
Ru2BiPyDA means ruthenium bis(BiPy)(diamino)
Ru3BiPyDA means ruthenium tris(BiPy)(diamino)
$RuCl_3$ means ruthenium(III) chloride
SCE means standard calomel electrode
[SF] means surface functionality on a [DP] as described in US 2007-0298006 or on a [PB]
SIS means sterically induced stoichiometry
Substituted Group means (e.g., substituted Alkyl, Alkenyl, or Alkynyl group) includes at least one substituent selected from the following: halogen, alkoxy, mercapto, aryl, alkoxycarbonyl, alkylaminocarbonyl, dialkylaminocarbonyl, OH, $NH_2$, alkylamino, dialkylamino, trialkylammonium alkanoylamino, arylcarboxamido, hydrazino, alkylthio, alkenyl, and other reactive groups.
TBAB means tetrabutyl ammonium bromide
TEA means triethylamine
TEDA means triethylenediamine
TETA means triethylenetetraamine
THF means tetrahydrofuran
TMC means transition metal complex as shown by Formula 1
TMPTA means trimethylolpropane triacrylate
TMPTGE means trimethylolpropane triglycidyl ether
TREN means tris(2-aminoethyl)amine
TRIS means tris(hydroxymethyl)aminomethane
Tween means polyoxyethylene (20) sorbitan mono-oleate
UF means ultrafiltration

SOME PURPOSES OF THIS INVENTION

Although nature excels at the production of electrical energy using compounds available in biological systems, scientific technologies have been much less successful, in part, because of biological fouling of the active catalyst surfaces significantly reduces performance. Since efficient generation of electrical power from compounds in biological systems is desired, development of bio-nano power cell (BNPC) systems that are resistant to biological fouling and still efficiently generate electrical power from compounds found in biological systems are needed.

Bio-nano power cells (BNPC) made with TMC and these nano-scale Dendritic Polymers generate electrical power from compounds in biological systems, have surface functionalities that may undergo further reactions, and have void spaces that may entrap and carry materials for sensed delivery. Thus these systems have many advantages over either system known separately.

Also TMC can be reacted with each other through their ligands to form an agglomerate that can be used as nanowires which may be attached to a polymer backbone or coated with a Dendritic Polymer.

Chemical Structure

Generally, the present invention relates to transition metal complexes [TMC] as modified from Formula A above as shown below.

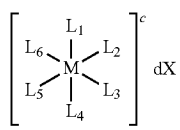

Formula 1 wherein $L_1$, $L_2$, $L_3$, $L_4$, $L_5$, $L_6$, collectively [L], can be the same or different ligand that is bound or associated with the metal [M]. At least one, and often all [L] have at their end terminus as a reactive site [RS] that enables their reaction with one another (e.g., to form dimers or aggregates), or to be cross-linked on their surface, or bound to a polymer backbone [PB] or a Dendritic Polymer. These ligands [L] can be any organic or inorganic moiety that can associate with [M]. A covalent or a strong bond is preferred as the [M] should remain associated with the [L] and not easily disassociate. c is an integer selected from −1 to −5, 0 or +1 to +5 indicating a negative, neutral or positive charge. X represents a counter ion and d is an integer from 1 to 5 representing the number of counter ions. Formula 1 is charge neutral.

Crosslinking

Electron transport involves an exchange of electrons between segments of the redox polymers (e.g., one or more [TMC] coupled to a [PB], as described in Formula 2) in a crosslinked film disposed on an electrode. The transition metal complex [TMC] can be bound to the polymer backbone [PB] though covalent, coordinative or ionic bonds, where covalent and coordinative binding are preferred. Electron exchange occurs, for example, through the collision of different segments of the crosslinked redox polymer. Electrons transported through the redox polymer can originate from, for example, electro-oxidation or electro-reduction of an enzymatic substrate, such as, for example, the oxidation of glucose by glucose oxidase.

The degree of crosslinking of the redox polymer can influence the transport of electrons or ions and thereby the rates of the electrochemical reactions. Excessive crosslinking of the polymer can reduce the mobility of the segments of the redox polymer. A reduction in segment mobility can slow the diffusion of electrons or ions through the redox polymer film. A reduction in the diffusivity of electrons, for example, can require a concomitant reduction in the thickness of the film on the electrode where electrons or electron vacancies are collected or delivered. The degree of crosslinking in a redox polymer film can thus affect the transport of electrons from, for example, an enzyme to the transition metal redox centers of the redox polymer such as, for example, $Os^{2+/3+}$ metal redox centers; between redox centers of the redox polymer; and from these transition metal redox centers to the electrode.

Inadequate crosslinking of a redox polymer can result in excessive swelling of the redox polymer film and to the leaching of the components of the redox polymer film. Excessive swelling can also result in the migration of the swollen polymer into the analyzed solution, in the softening of the redox polymer film, in the films susceptibility to removal by shear, or any combination of these effects.

Crosslinking can decrease the leaching of film components and can improve the mechanical stability of the film under shear stress. For example, as disclosed in Binyamin, G. and Heller, A; *Stabilization of Wired Glucose Oxidase Anodes Rotating at 1000 rpm at 37° C.; J. of the Electrochemical Soc.*, 146(8), 2965-2967 (1999), herein incorporated by reference, replacing a difunctional crosslinker, such as polyethylene glycol diglycidyl ether, with a trifunctional crosslinker such as N,N-diglycidyl-4-glycidyloxyaniline, for example, can reduce leaching and shear problems associated with inadequate crosslinking. Examples of other bifunctional, trifunctional and tetrafunctional crosslinkers are the [EX], [BR] used for the [DP] growth, with the [EX] moieties and long chain diamines preferred.

Alternatively, the number of crosslinking sites can be increased by reducing the number of [TMC] attached to the [PB], thus making more polymer pendant groups available for crosslinking One important advantage of at least some of the redox polymers is the increased mobility of the pendant transition metal complexes, resulting from the flexibility of the pendant groups. As a result, in at least some embodiments, fewer transition metal complexes per polymer backbone are needed to achieve a desired level of diffusivity of electrons and current density of analyte electro-oxidation or electro-reduction.

Addition of the Dendritic Polymers [DP] yields a more uniform rod-like structure (for example dendritic rods or dendrigrafts) with sufficient biocompatibility so that a separate membrane layer or other layer is not required. While greater structure ordering may reduce flexibility and transport of electrons or ions and thereby the rates of electrochemical reactions, the Dendritic Polymers and their surface groups improve biocompatibility so much that some electron transport reduction is acceptable. This molecule can be further polymerized to form larger molecules, aggregates and sheets.

Although these TMC can react together to form nanoscale masses of TMC that have likely utility as nanowires, such TMC are also desired to be "coated" by covalent reaction to Dendritic Polymers and/or bound to a polymer backbone. Thus in one embodiment of this invention TMC+Dendritic Polymer=bio-nano power cell (BNPC). Both of these components have been described earlier in the specification and are modifications of known entities. However, for the present invention these two components are joined by covalent bonds and modified for making the BNPC having the present utilities.

These BNPC have a TMC of Formula 1 as their core that provide the electron transfer mechanism for the BNPC and then are enveloped by a Dendritic Polymer to protect the core and provide the required solubility, biocompatibility, and/or structural properties for the BNPC. The BNPC moieties of this invention are shown by the following formula:

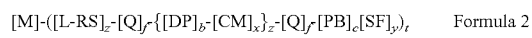

Formula 2 wherein:

[M] is an iron, cobalt, ruthenium, osmium, or vanadium metal ion;

[L-RS] means a ligand or groups of ligands, including monodentate, bidentate, and tridentate ligands (as shown by Formula 1 above) that have a Reactive Site [RS];

z is independently 0 or from 1 to 6;

[Q] means a linker moiety having at least 2 reactive sites and if more that 1 [Q] is present, they may be the same or different moieties;

f is independently 0 or from 1 to the number of [RS];

[DP] means Dendritic Polymer and has all the characteristics of such Dendritic Polymers as discussed herein having the ability to react with [RS] and the number of generations, G, of [DP], counting as concentric branch cell shells outward from the core [TMC] and usually counting sequentially from the core, where G=from 0 to the de Gennes dense packing of the surface or N-SIS effects; preferably the surface groups on the [DP] are biocompatible;

b is independently 0 or from 1 to at least the number of [L-RS] present;

[CM] means carried material;

x means 0 or an integer from 1 to 4000;

[PB] means polymer backbone;

c is independently 0 or from 1 to 6;

[SF] means the surface functionality groups that can either react with or associate with an enzyme, analyte, cross-linking group, [CM], or be inert;

y means from 1 to the total number of possible surface groups available, and if greater than 1 may be the same or different moiety; and t is from 1 to 6, provided that when t is less than 6, the other available sites on [M] may be [L], H, F, Cl, Br, I, CN, SCN, OH, $H_2O$, $NH_3$, alkylamine, dialkylamine, tri-alkylamine, alkoxy, heterocyclic compounds or polymer backbones that do not have reactive sites; and provided that for at least one entity where t is 1 or more, all z are at least 1 and b is 1.

To describe the present invention of Formula 2 further and clarify its components, the preparation of useful ligands, transition metal complex (TMC) cores, and Dendritic Polymers, and how they are used to make the BNPC of this invention the following further discussion is provided. Although Formula 2 is shown in a linear order, the various terms can appear in any order so long as they are bound to at least one other moiety in Formula 2 in manner required above. Also in another aspect of Formula 2 at least one [L] by its reactive site [RS] may be covalently bonded to at least one other TMC ligand (see FIG. 4) or to a [DP] (see FIG. 3) or between two [L] reactive sites [RS] and a [DP] or [PB] (see FIG. 8).

While a stepwise synthetic pathway description is presented in some detail below, it is possible for those skilled in the art to identify alternate synthetic pathways to yield similar effective BNPC. These alternate synthetic pathways fall within the scope of this invention since they yield the same or very similar BNPCs.

Transition metal complexes (TMC), shown by Formula 1 above, that are useful as Redox Mediators consist of the following:

[M] is a transition metal and is typically iron, cobalt, ruthenium, osmium, or vanadium metal ion;

$[L_g]$ that form TMC cores, g is from 2-6 ligands via coordinative bonds as illustrated below:

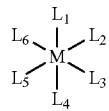

Formula 1

The six ligands of $[L_g]$, $L_1$, $L_2$, $L_3$, $L_4$, $L_5$, and $L_6$ in Formula 1 are, in any combination, monodentate, bidentate, tridentate, or tetradentate ligands, as described by a)-h) below:

a) six independent monodentate ligands, $L_1$, $L_2$, $L_3$, $L_4$, $L_5$, and $L_6$, which can be the same or different, in combination, as illustrated by Formula 1 above;

b) $L_1$ and $L_2$ in combination are a bidentate ligand, $L_3$, $L_4$, $L_5$ and $L_6$ are the same or different mono-dentate ligands, in combination, as illustrated by Formula 1-A below:

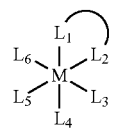

Formula 1-A c) $L_1$ and $L_2$ in combination are a bidentate ligand, $L_3$ and $L_4$ in combination are a bidentate ligand, and $L_5$ and $L_6$ are the same or different mono-dentate ligands, in combination, as illustrated by Formula 1-B below:

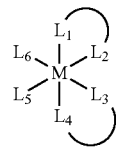

Formula 1-B d) $L_1$ and $L_2$ in combination, $L_3$ and $L_4$ in combination, and $L_5$ and $L_6$ in combination, form three independent bidentate ligands which can be the same or different, in combination, as illustrated by Formula 1-C below:

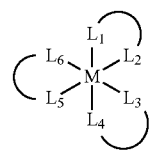

Formula 1-C e) $L_1$ is a monodentate ligand, $L_2$, $L_3$ and $L_4$ in combination form a tridentate ligand, and $L_5$ and $L_6$ in combination form a bidentate ligand, in combination, as illustrated by Formula 1-D below:

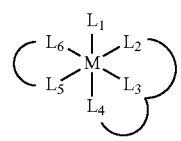

Formula 1-D f) $L_1$, $L_5$ and $L_6$ in combination form a tridentate ligand and $L_2$, $L_3$ and $L_4$ in combination form a tridentate ligand, in combination, as illustrated by Formula 1-E below:

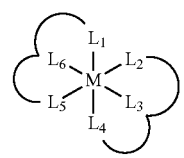

Formula 1-E g) $L_1$, $L_2$, $L_3$ and $L_4$ in combination form a tetradentate ligand, and $L_5$ and $L_6$ are the same or different mono-dentate ligands, in combination, as illustrated by Formula 1-F below:

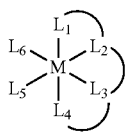

Formula 1-F h) $L_1$, $L_2$, $L_3$ and $L_4$ in combination form a tetradentate ligand, and $L_5$ and $L_6$ in combination form a bidentate ligand, in combination, as illustrated by Formula 1-G below:

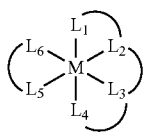

Formula 1-G

Each of these Formulae 1-A through 1-G are encompassed within the structure shown by Formula 1 above.

Monodentate Ligands

Some suitable monodentate ligands of Formula 1 include, but are not limited to, F, Cl, Br, I, CN, SCN, OH, $H_2O$, $NH_3$, alkylamine, dialkylamine, trialkylamine, alkoxy or heterocyclic compounds. The alkyl or aryl portions of any of the ligands are optionally substituted by F, Cl, Br, I, alkylamino, dialkylamino, trialkylammonium (except on aryl portions), alkoxy, alkylthio, aryl, or a Reactive Group. Any alkyl portions of the monodentate ligands generally contain 1 to 12 carbons. More typically, the alkyl portions contain 1 to 6 carbons.

In other embodiments, the monodentate ligands are heterocyclic compounds containing at least one nitrogen, oxygen, or sulfur atom. Examples of suitable heterocyclic monodentate ligands include imidazole, pyrazole, oxazole, thiazole, pyridine, pyrazine and derivatives thereof. One suitable heterocyclic monodentate ligand is substituted or unsubstituted imidazole for Formula 3 below:

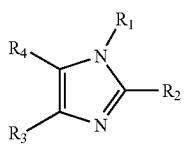

Formula 3 wherein: $R_1$ is generally a substituted or unsubstituted alkyl, alkenyl, or aryl group. Typically, $R_1$ is a substituted or unsubstituted $C_1$-$C_{12}$ alkyl or alkenyl.

$R_1$, $R_2$ and $R_3$ are independently H, F, Cl, Br, I, $NO_2$, CN, $CO_2H$, $SO_3H$, $NHNH_2$, SH, aryl, alkoxycarbonyl, alkylaminocarbonyl, dialkylaminocarbonyl, OH, alkoxy, $NH_2$, alkylamino, dialkylamino, alkanoylamino, arylcarboxamido, hydrazino, alkylhydrazino, hydroxylamino, alkoxyamino, alkylthio, alkenyl, aryl, or alkyl.

Alternatively, $R_3$ and $R_4$, in combination, form a fused 5 or 6-membered ring that is saturated or unsaturated.

The substitution of inner coordination sphere chloride anions by imidazoles does not typically cause a large shift in the redox potential in the oxidizing direction, differing in this respect from substitution by pyridines, which typically results in a large shift in the redox potential in the oxidizing direction.

Another suitable heterocyclic monodentate ligand is substituted or unsubstituted pyridine having the following general Formula 4 below:

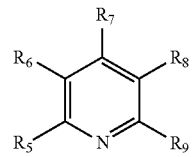

Formula 4 wherein: $R_5$, $R_6$, $R_7$, $R_8$ and $R_9$, are independently H, F, Cl, Br, I, $NO_2$, CN, $CO_2H$, alkoxycarbonyl, alkylaminocarbonyl, dialkylaminocarbonyl, OH, alkoxy, $NH_2$, alkylamino, dialkylamino, alkanoylamino, arylcarboxamido, hydrazino, alkylhydrazino, hydroxylamino, alkoxyamino, alkylthio, alkenyl, aryl, or alkyl. The alkyl or aryl portions of any of the substituents are optionally substituted by F, Cl, Br, I, alkylamino, dialkylamino, trialkylammonium (except for aryl portions), alkoxy, alkylthio, aryl, or a Reactive Group. Generally, $R_5$, $R_6$, $R_7$, $R_8$ and $R_9$ are H, methyl, $C_1$-$C_2$ alkoxy, $C_1$-$C_2$ alkylamino, $C_2$-$C_4$ dialkylamino, or a $C_1$-$C_6$ lower alkyl substituted with a Reactive Group.

Bidentate Ligands

Examples of suitable bidentate ligands of Formula 1 include, but are not limited to, amino acids (D, L or both), oxalic acid, acetylacetone, diaminoalkanes, ortho-diaminoarenes, 2,2-biimidazole, 2,2-bioxazole, 2,2-bithiazole, 2-(2-pyridyl)imidazole, and 2,2-bipyridine and derivatives thereof. Particularly suitable bidentate ligands for Redox Mediators include substituted and unsubstituted 2,2-biimidazole, 2-(2-pyridyl)imidazole and 2,2-bipyridine. The substituted 2,2 biimidazole and 2-(2-pyridyl)imidazole ligands can have the same substitution patterns described above for the other 2,2-biimidazole and 242-pyridyl)imidazole ligand.

One example of a bidendate ligand is a 2,2-biimidazole having the following Formula 5 below:

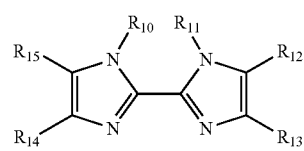

Formula 5 wherein: $R_{10}$, $R_{11}$, $R_{12}$, $R_{13}$, $R_{14}$, and $R_{15}$ are substituents attached to carbon atoms of the 2,2-biimidazole and are independently H, F, Cl, Br, I, $NO_2$, CN, $CO_2H$, $SO_3H$, alkoxycarbonyl, alkylaminocarbonyl, dialkylaminocarbonyl, OH, alkoxy, $NH_2$, alkylamino, dialkylamino, diaminoalkanes, alkanoylamino, arylcarboxamido, hydrazino, alkylhydrazino, hydroxylamino, alkoxyamino, alkylthio, alkenyl, aryl, or alkyl.

Alternatively, $R_{14}$ and $R_{15}$ in combination or $R_{12}$ and $R_{13}$ in combination, independently form a saturated or unsaturated 5- or 6-membered ring. An example of this ring is a 2,2-bibenzoimidazole derivative.

Typically, the alkyl and alkoxy portions are $C_1$-$C_{12}$. The alkyl or aryl portions of any of the substituents are optionally substituted by F, Cl, Br, I, alkylamino, dialkylamino, diaminoalkanes, trialkylammonium (except on aryl portions), alkoxy, alkylthio, aryl, or a reactive group. Generally, $R_{10}$, $R_{11}$, $R_{12}$, $R_{13}$, $R_{14}$, and $R_{15}$ are H, $CO_2H$, $SO_3H$, alkoxycarbonyl, alkylaminocarbonyl, dialkylaminocarbonyl, OH, alkoxy, $NH_2$, alkylamino, dialkylamino, diaminoalkanes, alkanoylamino, arylcarboxamido, hydrazino, alkylhydrazino, hydroxylamino, alkoxyamino, alkylthio, alkenyl, aryl, or alkyl. Typically, $R_{10}$, $R_{11}$, $R_{12}$, $R_{13}$, $R_{14}$, and $R_{15}$ are H, methyl, $CO_2H$, $SO_3H$, alkoxycarbonyl, alkylaminocarbonyl, dialkylaminocarbonyl, OH, or $NH_2$, to provide reactive site functionality [RS] for subsequent branching reactions.

Another example of a bidendate ligand is a 2-(2-pyridyl) imidazole having the following Formula 6:

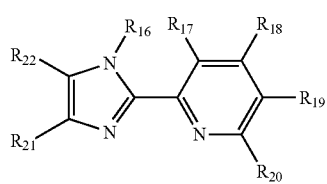

Formula 6 wherein: $R_{16}$ is a substituted or unsubstituted aryl, alkenyl, or alkyl. Generally, $R_{16}$ is a substituted or unsubstituted $C_1$-$C_{12}$ alkyl. $R_{16}$ is typically methyl or a $C_1$-$C_{12}$ alkyl that is optionally substituted with a Reactive Group.

$R_{17}$, $R_{18}$, $R_{19}$, $R_{20}$, $R_{21}$, and $R_{22}$ are independently H, F, Cl, Br, I, $NO_2$, CN, $CO_2H$, $SO_3H$, $NHNH_2$, SH, alkoxylcarbonyl, alkylaminocarbonyl, dialkylaminocarbonyl, OH, alkoxy, $NH_2$, alkylamino, dialkylamino, diaminoalkanes, alkanoylamino, arylcarboxamido, hydrazino, alkylhydrazino, hydroxylamino, alkoxylamino, alkylthio, alkenyl, aryl, or alkyl.

Alternatively, $R_{18}$ and $R_{19}$ in combination or $R_{21}$ and $R_{22}$ in combination can form a saturated or unsaturated 5- or 6-membered ring.

Typically, the alkyl and alkoxy portions are $C_1$-$C_{12}$. The alkyl or aryl portions of any of the substituents are optionally substituted by H, F, Cl, Br, I, $CO_2H$, $SO_3H$, alkoxycarbonyl, alkylaminocarbonyl, dialkylaminocarbonyl, OH, or $NH_2$ or a Reactive Group. Generally, $R_{17}$, $R_{18}$, $R_{19}$, $R_{20}$, $R_{21}$ and $R_{22}$ are independently H or unsubstituted alkyl groups. Typically, $R_{17}$, $R_{18}$, $R_{19}$, $R_{20}$, $R_{21}$ and $R_{22}$ are H, methyl, $CO_2H$, $SO_3H$, alkoxycarbonyl, alkylaminocarbonyl, dialkylaminocarbonyl, OH, or $NH_2$, to provide reactive site functionality [RS] for subsequent branching reactions.

Another example of a bidendate ligand is 2,2-bipyridine that has the following Formula 7;

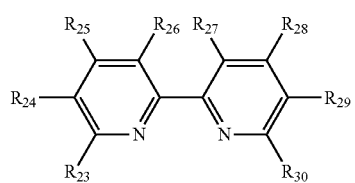

Formula 7 wherein: $R_{23}$, $R_{24}$, $R_{25}$, $R_{26}$, $R_{27}$, $R_{28}$, $R_{29}$ and $R_{30}$ are independently H, F, Cl, Br, I, $NO_2$, CN, $CO_2H$, $SO_3H$, $NHNH_2$, SH, aryl, alkoxycarbonyl, alkylaminocarbonyl, dialkylaminocarbonyl, OH, alkoxy, $NH_2$, alkylamino, dialkylamino, diaminoalkanes, alkanoylamino, arylcarboxamido, hydrazino, alkylhydrazino, hydroxylamino, alkoxylamino, alkylthio, alkenyl, or alkyl. Typically, $R_{23}$, $R_{24}$, $R_{25}$, $R_{26}$, $R_{27}$, $R_{28}$, $R_{29}$ and $R_{30}$ are H, methyl, $CO_2H$, $SO_3H$, alkoxycarbonyl, alkylaminocarbonyl, dialkylaminocarbonyl, OH, or $NH_2$, to provide reactive site functionality [RS] for subsequent branching reactions.

Specific examples of suitable combinations of $R_{23}$, $R_{24}$, $R_{25}$, $R_{26}$, $R_{27}$, $R_{28}$, $R_{29}$ and $R_{30}$ include $R_{23}$ and $R_{30}$ as H or methyl; $R_{24}$ and $R_{29}$ as the same and H or methyl; and $R_{26}$ and $R_{27}$ as the same and H or methyl.

An alternative combination is where one or more adjacent pairs of substituents $R_{23}$ and $R_{24}$, on the one hand, and $R_{29}$ and $R_{30}$, on the other hand, independently form a saturated or unsaturated 5- or 6-membered ring. Another combination includes $R_{26}$ and $R_{27}$ forming a saturated or unsaturated five or six membered ring.

Another combination includes $R_{23}$, $R_{24}$, $R_{25}$, $R_{26}$, $R_{27}$, $R_{28}$, $R_{29}$ and $R_{30}$ as the same and $R_{25}$ and $R_{28}$ as independently H, alkoxy, $NH_2$, alkylamino, dialkylamino, diaminoalkanes, alkylthio, alkenyl, or alkyl. The alkyl or aryl portions of any of the substituents are optionally substituted by F, Cl, Br, I, alkylamino, dialkylamino, diaminoalkanes, trialkylammonium (except on aryl portions), alkoxy, alkylthio, aryl, or a Reactive Group. As an example, $R_{18}$ and $R_{21}$ can be the same or different and typically are H, methyl, $CO_2H$, $SO_3H$, alkoxycarbonyl, alkylaminocarbonyl, dialkylaminocarbonyl, OH, or $NH_2$, to provide reactive site functionality [RS] for subsequent branching reactions.

Tridentate Ligands

Examples of suitable tridentate ligands include, but are not limited to, diethylenetriamine, 2,2,2"-terpyridine, 2,6-bis(N-pyrazolyl)pyridine, and derivatives of these compounds. 2,2, 2"-terpyridine and 2,6-bis(N-pyrazolyl)pyridine have the following general Formulae 8 and 9, respectively:

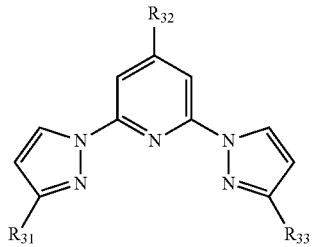

Formula 8 wherein: $R_{31}$, $R_{32}$ and $R_{33}$ are independently H or substituted or unsubstituted $C_1$-$C_{12}$ alkyl. Typically, $R_{31}$, $R_{32}$ and $R_{33}$ are H, methyl, $CO_2H$, $SO_3H$, alkoxycarbonyl, alkylaminocarbonyl, dialkylaminocarbonyl, OH, or $NH_2$, to provide reactive site functionality [RS] for subsequent branching reactions. Other substituents at these or other positions of the compound of Formulas 8 can be added.

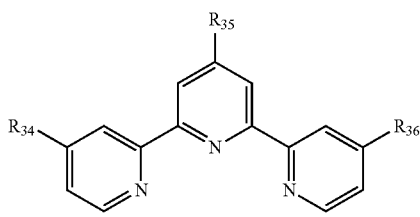

Formula 9 wherein: $R_{34}$, $R_{35}$ and $R_{36}$ are independently H, F, Cl, Br, I, $NO_2$, CN, $CO_2H$, $SO_3H$, $NHNH_2$, SH, alkoxycarbonyl, alkylaminocarbonyl, dialkylaminocarbonyl, OH, alkoxy, $NH_2$, alkylamino, dialkylamino, diaminoalkanes, alkanoylamino, arylcarboxamido, hydrazino, alkylhydrazino, hydroxylamino, alkoxylamino, alkylthio, alkenyl, aryl, or alkyl. The alkyl or aryl portions of any of the substituents are optionally substituted by F, Cl, Br, I, alkylamino, dialkylamino, diaminoalkanes, trialkylammonium (except on aryl portions), alkoxy, alkylthio, aryl, or a Reactive Group. Typically, $R_{34}$, $R_{35}$ and $R_{36}$ are H, methyl, $CO_2H$, $SO_3H$, alkoxycarbonyl, alkylaminocarbonyl, dialkylaminocarbonyl, OH, or $NH_2$, to provide reactive site functionality [RS] for subsequent branching reactions.

Examples of suitable tridentate ligands include, but are not limited to, triethylenetriamine, ethylenediaminediacetic acid, tetraaza macrocycles and similar compounds as well as derivatives thereof.

Ligands [L] and Reactive Site Functionality [RS]

Reactive site functionality [RS] moieties must be attached to at least one [L] to enable branching, crosslinking and other reactions to occur with Dendritic Polymers, Polymer Backbones or other surface functionalities [SF].

Focal Point Functionality [FF] of Dendrons

The focal point functionality [FF] moieties serve to enable a dendron to be used as a reactive site at its focal point that is further reacted, including but not limited to joining two or more dendrons together or reacting with a TMC through [L-RS] or in place of [L-RS], another branching agent [BR], or extender [EX] and [BR]. The maximum [FF] moieties possible are $N_o-1$ of the TMC (in place of [L] but at least one [L] must be present) but also on the number of available reactive [L-RS]. When all [L-RS] reactive entities are not reacted, then [RS] is present and observed. If all [L-RS] have been reacted with a dendron, then a Dendritic Polymer is formed where the core is TMC and the dendrons completely covalently surround it in the usual dendritic manner. Preferably a is from 1 to the valence of the metal [M], especially from 1 to 6 [RS] moieties.

Figure 3:
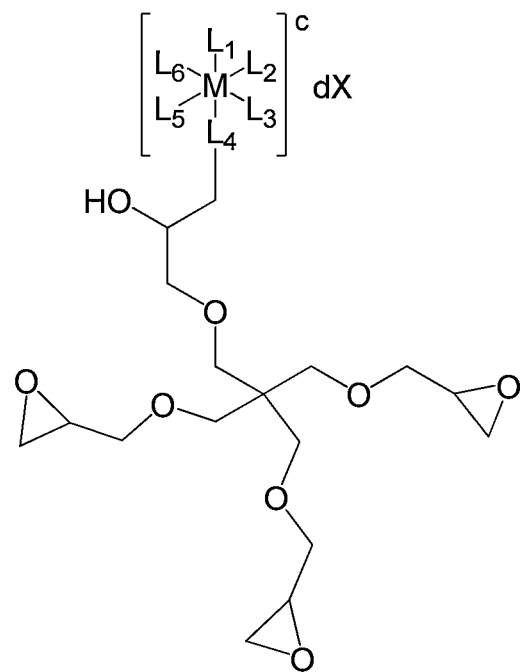
FIG. 3 illustrates a BNPC with a TMC core and 6 [L] where 1 [L] has been reacted with a starting material for a Dendritic Polymer.
Figure 4:
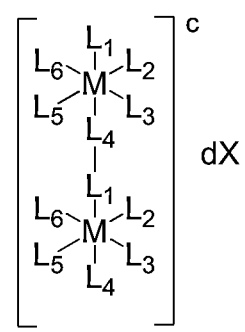
FIG. 4 illustrates a TMC dimer.
Figure 5:
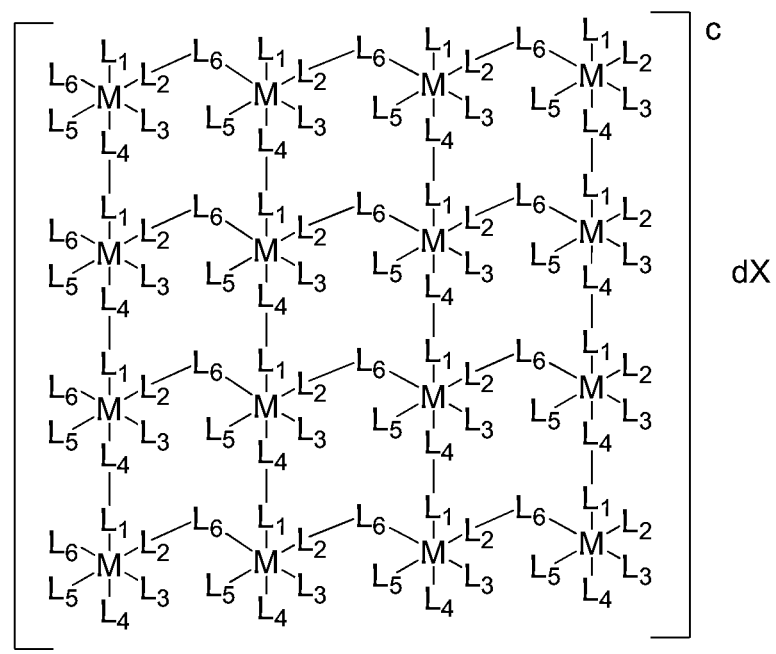
FIG. 5 illustrates a TMC network.

Preferred [RS] moieties to react with a dendron are hydrogen, thiols, amines, carboxylic acids, esters, ethers, cyclic ethers (e.g., crown ethers, cryptands), porphyrins, hydroxyl, maleimides, alkyls, alkenyls, alkynyls, alkyl halides, arylalkyl halides, phosphinos, phosphines, boranes, alcohols, aldehydes, acrylates, cyclic anhydrides, aziridines, pyridines, nitriles, itaconates, cyclic thiolactones, thioranes, azetidines, cyclic lactones, macrocyclics (e.g., DOTA, DO3A), chelating ligands (e.g., DTPA) isocyanates, isothiocyanates, oligonucleotides, amino acids, peptides, cyclopeptides, proteins, antibodies, or fragments, aptamers, imidazoles, azides, mercaptoamines, silanes, oxazolines, oxirane, oxetane, oxazines, imines, tosylates, metals, biotin, streptavidin, avidin, protecting groups (e.g., BOC or ketone solvent protected), siloxanes or its derivatives, or substituted derivatives or combinations thereof, or groups suitable for click chemistry (e.g., polyazido or polyalkyne functionality). The number of carbons present in each of these hydrocarbon moieties, when present, is from at least 1 to 25; halo means chloro, bromo, fluoro, or iodo; hetero means S, N, O, Si, B, or P. Preferred groups are mercapto, amino, carboxyl and carboxyl esters, oxazoline, isothiocyanates, isocyanates, hydroxyl, epoxy, orthoester, acrylates, methacrylates, styrenyl, and vinylbenzylic moieties. The ability of the [FF] group(s) on the dendron to react further can be estimated by N-SIS. FIG. 3 illustrates a BNPC with a TMC core and 6 [L] where 1 [L] has been reacted with a starting material for a Dendritic Polymer.

Bio-Nano Power Cells [BNPC]

The BNPC of the present invention is formed by the reaction of TMC and Dendritic Polymers as shown in Formula 2.

TMC is the Core [C] of the BNPC

A transition metal complex core [TMC-C] includes a simple transition metal complex core [TMC]-[C], a multiple transition metal complex core [m-TMC-C], a scaffolding transition metal complex core [s-TMC-C], a super transition metal complex core [sp-TMC-C] and a carried material transition metal complex core [CM-TMC-C]. These cores may be electrophilic (E), nucleophilic (N) or other (O) moiety as described hereafter. The core [C] must be capable of further reaction. Additionally, one or more, but less than all, of the core functionalities $N_o$ may be temporarily or permanently capped with a non-reactive group (e.g., t-BOC, esters, acetals, ketals, etc.).

A simple transition metal complex core [TMC]-[C] is virtually any core having at least two reactive ends can be used. When the Dendritic Polymer is a PEHAM then, when there are only two such reactive ends, a branch cell [BR] group is reacted at some point during the formation of the BNPC and either an interior functionality [IF] or extender [EX] or both are also present in the final BNPC.

A multiple transition metal complex core [m-TMC-C] is virtually any core with at least two reactive ends can be used, provided that when there are only two such reactive ends, two or more [M] and [L] complexes, a [BR] group is reacted at some point during the formation of the BNPC and either a [IF] or [EX] or both are also present in the final BNPC. Multiple transition metal complex cores may have the same or different enzyme receptors as [SF] such that, in some iterations, an anode and a cathode are contained within the same core.

A scaffolding transition metal complex core [s-TMC-C] is one where the simple core has other moieties or entities attached which then serve as the platform for the Dendritic Polymer growth to the first generation. Examples of [s-TMC-C] include, but are not limited to, capped materials, such as TMPTA capped with PIPZ, PETGE, TMPTGE, TPEGE, or TPMTGE, each capped with one or more aminoethylpiperazine, azides, propargyl functionalities, piperazine, di-imminodiacetic acids, or epoxide surface PEHAMS or mixtures thereof. One of the most useful scaffolding cores is where a TMC is attached to a reactive end containing polymer, via direct covalent connection or by connecting group reactions. The reactive end of either the TMC or the polymer can be used for dendritic branching reactions or other reactions to protect the core.

A super transition metal complex core [sp-TMC-C] is where a TMC serves as the core functionality and other dendritic structures may be attached or grown from its surface. Some examples of super cores are: [TMC-C] as the core with PAMAM grown on or attached to its surface; [TMC-C] as the core with PEHAM grown on or attached to its surface; [TMC-C] as the core with PEHAM and PAMAM grown on or attached to its surface; [m-TMC-C] as the core with PEHAM and PAMAM grown on or attached to its surface; [m-TMC-C] as the core with PAMAM grown on or attached to its surface; [m-TMC-C] as the core and PEHAM is grown on or attached to its surface; [s-TMC-C] as the core with PEHAM and PAMAM grown on or attached to its surface; [s-TMC-C] as the core with PAMAM grown on or attached to its surface; or [s-TMC-C] as the core and PEHAM is grown on or attached to its surface. After these various cores have the other Dendritic Polymers grown on or attached to them, they are a super core.

A [sp-TMC-C] is also where a TMC serves as the core functionality and other dendritic structures are attached or grown from its surface (e.g., at [L-RS]). Carried materials [CM] such as zero valent metal particles (e.g., Au, Ag, Cu, Pd, Pt), gold nanoparticles, gold nanorods, colloids, latex particles, metal oxides, micelles, vesicles, liposomes, buckyballs, carbon nanotubes (single and multi wall), carbon fibers, silica or bulk metal surfaces, or other structures, are attached to or grown from the carried material transition metal complex core [CM-TMC-C] surface.

TMC cores of any of the above types are referred to as [TMC-C] and have at least one nucleophilic (Nu) or one electrophilic (E) moiety; or a polyvalent core bonded to at least two ordered dendritic branches (O); or a core atom or molecule that may be any monovalent or monofunctional moiety or any polyvalent or polyfunctional moiety, preferably a polyfunctional moiety having 2-2300 valence bonds of functional sites available for bonding with dendritic branches. Thus either the [M] or the [L] must have a reactive group that is able to further react and bond with a Dendritic Polymer.

Nucleophilic core examples present on the TMC include ammonia, water, hydrogen sulfide, phosphine, poly(alkylenediamines) such as EDA, HMDA, dodecyl diamines, polyalkylene polyamines such as DETA, TETA, tetraethylenepentaamine, pentaethylenehexamine, poly(propyleneimine), linear and branched poly(ethyleneimine) and poly(amidoamines), primary amines such as methylamine, hydroxyethylamine, octadecylamine, poly(methylenediamines), macrocyclic/cryptand polyamines, poly(aminoalkylarenes), tris (aminoalkyl)amines, methylisopropylidine, alkylene bis(2-halo-ethylamines), arylmethyl halides (e.g., benzylic halides), hyperbranched (e.g., polylysine), poly(propyleneimine), tris-2-(aminoethylamine), heterocyclic amines, star/combbranched polyamines, piperazine and its derivatives (e.g., aminoalkyl piperazines), and other various amines. Other nucleophilic cores are polyvinyl alcohols, polyvinyl amines, ethylene glycol, polyalkylene polyols, polyalkylene polymercaptans, thiophenols and phenols. Any of these cores may be as capped cores [e.g., tert-butoxycarbonyl (BOC)] where at least one $N_o$ valence is uncapped.

Examples of electrophilic cores present on the TMC include those where the core is converted to an (E) with Brönsted/Lewis acids or alkylation/acylation agents and is cyclic ethers (e.g., epoxides), oxiranes, cyclic sulfides (epichlorosulfide), aziridines, azetidines, siloxanes, oxetanes, oxazolines, oxazines, carbamates, caprolactones, carboxyanhydrides, thiolactones, sultones, β-lactams, α,β-ethylenically unsaturated carboxylic esters such as methyl acrylate, ethyl acrylate, ($C_2$-$C_{18}$ alkyl)methacrylate esters, acrylonitrile, methyl itaconate, dimethyl fumarates, maleic anhydride, and amides such as acrylamide or any of these cores as capped cores where at least one $N_o$ valence is uncapped.

There are also polyfunctional initiator cores (core compound) for (O) as (C) that can be present in the TMC that are compounds capable of generating a polyvalent core or free-radical receptor groups (e.g., olefinics), or 1,3-dipolar cycloaddition moieties (e.g., polyalkynes and polyazides). Also included are star/combbranched polyamines.

The difference between known cores for Dendritic Polymers and the present cores are that the present cores must have a TMC at a component of the core. Other entities can be present with the TMC provided that the desired utility is not adversely affected. Thus, cores known from Dendritic Polymers as described in U.S. Pat. Nos. 4,507,466; 4,558,120; and 4,631,337 and many other literature and patent citations, may be used with the TMC. Preferred moieties of these cores are triacrylate, tetraacrylates, triaziridine, tetraaziridine, triazide, tetraazide, trithiorane, tetrathiorane, trioxazoline, tetraoxazoline, triepoxide, tetraepoxide, diglycidyl aniline, aminoalkylol such as aminoethanol, alkylenediamine such as ethylenediamine, triphenylmethane, neopentyl alcohols, triglycidylether, triarylmethane, tetraarylmethane, tetraglycidylether, bis(glycidoxyphenyl)alkane, methylene bis(diglycidylaniline), tetraepisulfide, trisglycidylisocyanurate, tris (2,3-epoxypropyl)-isocyanurate.

Some examples of suitable TMC are illustrated using Formulae 10 and 11 below:

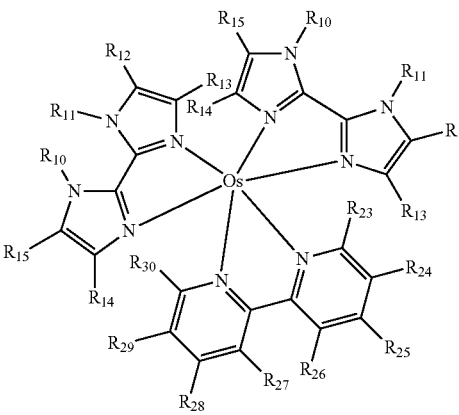

Formula 10 wherein: the metal osmium is complexed to two substituted 2,2-biimidazole ligands and one substituted or unsubstituted 2,2-bipyridine ligand.

$R_{10}$, $R_{11}$, $R_{12}$, $R_{13}$, $R_{14}$, $R_{15}$, $R_{23}$, $R_{24}$, $R_{25}$, $R_{26}$, $R_{27}$, $R_{28}$, $R_{29}$, $R_{30}$, c, d, and X are defined the same as described above.

In one embodiment, $R_{10}$ and $R_{11}$ are methyl; $R_{12}$, $R_{13}$, $R_{14}$, $R_{15}$, $R_{23}$, $R_{24}$, $R_{26}$, $R_{27}$, $R_{29}$ and $R_{30}$ are H; $R_{25}$ and $R_{28}$ are independently H, methyl, $C_1$-$C_{12}$ alkylamino, $C_2$-$C_{24}$ dialkylamino, carboxylic acid, activated ester, or amine. The alkyl or aryl portions of any of the substituents are optionally substituted by F, Cl, Br, I, alkylamino, dialkylamino, diaminoalkanes, trialkylammonium (except on aryl portions), alkoxy, alkylthio, aryl, or a reactive group. For example, $R_{25}$ and $R_{28}$ are a $C_1$-$C_{12}$ alkylamino or $C_2$-$C_{24}$ dialkylamino, diaminoalkanes, the alkyl portion(s) of which are substituted with a Reactive Group, such as a carboxylic acid, activated ester, or amine. Typically, the alkylamino group has 1 to 6 carbon atoms and the dialkylamino group has 2 to 8 carbon atoms.

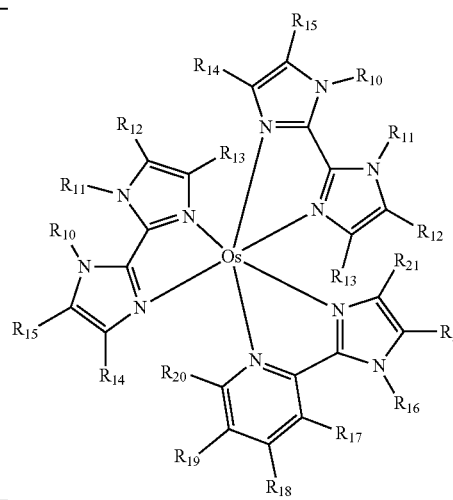

Formula 11 wherein: the metal osmium is complexed to two substituted 2,2-biimidazole ligands and one substituted or unsubstituted 2-(2-pyridyl)imidazole ligand. $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, c, d, and X are the same as described above.

In one embodiment, $R_{10}$ and $R_{11}$ are methyl; $R_{12}$, $R_{13}$, $R_{14}$, $R_{15}$, $R_{20}$, $R_{21}$, and $R_{22}$ are independently H or methyl; $R_{17}$ and $R_{19}$ are the same and are H; $R_{16}$, and $R_{18}$ are independently H, methyl, alkylamino, $C_2$-$C_{24}$ dialkylamino, carboxylic acid, activated ester, or amine. The alkyl or aryl portions of any of the substituents are optionally substituted by F, Cl, Br, I, alkylamino, dialkylamino, diaminoalkanes, trialkylammonium (except on aryl portions), alkoxy, alkylthio, aryl, or a reactive group.

The TMC of Formula 1 also include TMC that form dimers and larger networks of TMC by directed coordination by one or more of ligands [L], $L_1$, $L_2$, $L_3$, $L_4$, $L_5$, and $L_6$, or through coupling reactions through one or more of ligands [L], $L_1$, $L_2$, $L_3$, $L_4$, $L_5$, and $L_6$. The figures show only one depiction of the dimer (FIG. 3) and larger networks (FIG. 4); in practice, the metals [M] and the ligands [L] can be the same or different.

Figure 6:
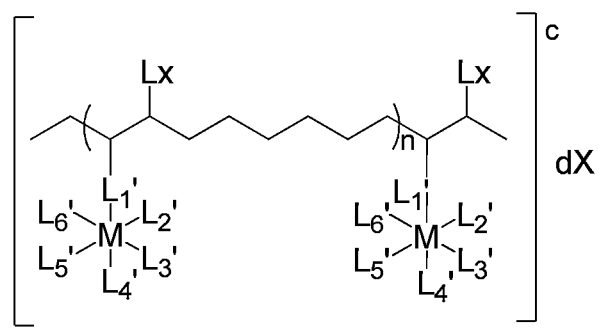
FIG. 6 illustrates "wired enzyme" biosensors coupled to a polymeric backbone through one or more of ligands [L].

The TMC of Formula 1 also include TMC that are coupled to a polymeric backbone through one or more of ligands [L], $L_1$, $L_2$, $L_3$, $L_4$, $L_5$, and $L_6$ as depicted by FIG. 6.

Additional examples of suitable TMC are described in U.S. Pat. No. 6,605,200, incorporated herein by reference. In some disclosed embodiments, the polymeric backbone has functional groups that act as ligands [L] of the TMC. Such polymeric backbones include, for example, poly(N-vinylpyridine) and poly(N-vinylimidazole) in which the pyridine and imidazole groups, respectively, can act as monodentate ligands [L] of the TMC. In other embodiments, the TMC can be the reaction product between a reactive group on a precursor polymer and a reactive group on a ligand of a precursor transition metal complex (such as a complex of Formula 1 above where one of L, $L_1$, $L_2$, $L_3$ and $L_4$ includes a Reactive Group). Suitable precursor polymers include, for example, poly(acrylic acid), styrene/maleic anhydride copolymer, methylvinylether/maleic anhydride copolymer (GANTREX polymer), poly(vinylbenzylchloride), poly(allylamine), polylysine, carboxy-poly(vinylpyridine), and poly(sodium 4-styrene sulfonate).

Alternatively, the TMC can have Reactive Group(s) for immobilization or conjugation of the complexes to other substrates or carriers, examples of which include, but are not limited to, macromolecules (e.g., enzymes) and surfaces (e.g., electrode surfaces).

For reactive attachment to polymers, substrates, or other carriers, the transition metal complex precursor includes at least one reactive group [RS] that reacts with a reactive group on the polymer, substrate, or carrier. Typically, covalent bonds are formed between the two reactive groups to generate a linkage. Examples of such linkages are provided in Table 1, below. Generally, one of the reactive groups is an electrophile (E) and the other reactive group is a nucleophile (N). These groups are well known in the art.

TABLE 1

Examples of Reactive Group Linkages

| First Reactive Group | Second Reactive Group | Resulting Linkage |
|---|---|---|
| Activated ester* | Amine | Carboxamide |
| Acrylamide | Thiol | Thioether |
| Acyl azide | Amine | Carboxamide |
| Acyl halide | Amine | Carboxamide |
| Carboxylic acid | Amine | Carboxamide |
| Aldehyde or ketone | Hydrazine | Hydrazone |
| Aldehyde or ketone | Hydroxyamine | Oxime |
| Alkyl halide | Amine | Alkylamine |
| Alkyl halide | Carboxylic acid | Carboxylic ester |
| Alkyl halide | Imidazole | Imidazolium |
| Alkyl halide | Pyridine | Pyridinium |
| Alkyl halide | Alcohol/phenol | Ether |
| Alkyl halide | Thiol | Thioether |
| Alkyl sulfonate | Thiol | Thioether |
| Alkyl sulfonate | Pyridine | Pyridinium |
| Alkyl sulfonate | Imidazole | Imidazolium |
| Anhydride | Alcohol/phenol | Ester |
| Anhydride | Amine | Carboxamide |
| Aziridine | Thiol | Thioether |
| Aziridine | Amine | Alkylamine |
| Aziridine | Pyridine | Pyridinium |
| Epoxide | Thiol | Thioether |
| Epoxide | Amine | Alkylamine |
| Epoxide | Pyridine | Pyridinium |
| Halotriazine | Amine | Aminotriazine |
| Halotriazine | Alcohol | Triazinyl ether |
| Imido ester | Amine | Amidine |
| Isocyanate | Amine | Urea |
| Isocyanate | Alcohol | Urethane |
| Isothiocyanate | Amine | Thiourea |
| Maleimide | Thiol | Thioether |
| Sulfonyl halide | Amine | Sulfonamide |

*Activated esters, as understood in the art, generally include esters of succinimidyl, benzotriazolyl, or aryl substituted by electron-withdrawing groups such as sulfo, nitro, cyano, or halo; or carboxylic acids activated by carbodiimides.

BNPC is [TMC-C]+Dendritic Polymer

BNPC of the present invention may have one or more of the following characteristics: redox potentials in a particular range, the ability to exchange electrons rapidly with electrodes, the ability to rapidly transfer electrons to or rapidly accept electrons from an enzyme to accelerate the kinetics of electro-oxidation or electro-reduction of an analyte in the presence of an enzyme or another analyte-specific redox catalyst. For example, a redox mediator may accelerate the electro-oxidation of glucose in the presence of glucose oxidase or PQQ-glucose dehydrogenase, a process that can be useful for the selective assay of glucose in the presence of other electrochemically oxidizable species. Compounds having Formula 2 are examples of BNPC of the present invention.

BNPC of the present invention can be soluble in water or other aqueous solutions, or in organic solvents. In general, the BNPC can be made soluble in either aqueous or organic solvents by having an appropriate counter ion or ions, X. For example, TMC complexed with small counter anions, such as $F^-$, $Cl^-$, and $Br^-$, tend to be water soluble. On the other hand, TMC with bulky counter anions, such as $I^-$, $BF_4^-$ and $PF_6^-$, tend to be soluble in organic solvents. Preferably, the solubility of TMC and BNPC of the present invention is greater than about 0.1 M (moles/liter) at 25° C. for a desired solvent.

The TMC discussed above are useful as Redox Mediators in electrochemical sensors for the detection of analytes in bio-fluids. The use of TMC as Redox Mediators is described, for example, in U.S. Pat. Nos. 5,262,035; 5,262,305; 5,320,725; 5,365,786; 5,378,628; 5,393,903; 5,593,852; 5,665,222; 5,972,199; 6,134,461; 6,143,164; 6,175,752; and 6,338,790; all of which are herein incorporated by reference. The TMC described herein can typically be used in place of those discussed in the patents listed above. The TMC that include a polymeric backbone and are Redox Mediators can also be referred to as "redox polymers".

Thus the TMC used in the present BNPC of Formula 2 have been modified from those TMC of Formula A as known in the prior art for this invention. The BNPC is an improved system for the use of TMC.

In general, the Redox Mediator is disposed on or in proximity to (e.g., in a solution surrounding) a working electrode. The Redox Mediator transfers electrons between the working electrode and an analyte. In some preferred embodiments, an enzyme is also included to facilitate the transfer. For example, the Redox Mediator transfers electrons between the working electrode and glucose (typically via an enzyme) in an enzyme-catalyzed reaction of glucose. Redox polymers are particularly useful for forming non-leachable coatings on the working electrode. These can be formed, for example, by crosslinking the redox polymer on the working electrode, or by crosslinking the redox polymer and the enzyme on the working electrode. One of the advantages of the present BNPC is that the Dendritic Polymer aids the retention of the TMC on the working electrode without crosslinking TMC or BNPC can enable accurate, reproducible and quick or continuous assays. TMC Redox Mediators accept electrons from, or transfer electrons to, enzymes or analytes at a high rate and also exchange electrons rapidly with an electrode. Typically, the rate of self exchange, the process in which a reduced Redox Mediator transfers an electron to an oxidized Redox Mediator, is rapid. At a defined Redox Mediator concentration, this provides for more rapid transport of electrons between the enzyme (or analyte) and electrode, and thereby shortens the response time of the sensor. Additionally, the novel TMC Redox Mediators are typically stable under ambient light and at the temperatures encountered in use, storage and transportation. Preferably, the transition metal complex redox mediators do not undergo chemical change, other than oxidation and reduction, in the period of use or under the conditions of storage, though the redox mediators can be designed to be activated by reacting, for example, with water or the analyte.

The TMC can be used as a Redox Mediator in combination with a redox enzyme to electro-oxidize or electro-reduce the analyte or a compound derived of the analyte, for example by hydrolysis of the analyte. The redox potentials of the Redox Mediators are generally more positive (i.e. more oxidizing) than the redox potentials of the redox enzymes when the analyte is electro-oxidized and more negative when the analyte is electro-reduced. For example, the redox potentials of the preferred TMC Redox Mediators used for electro-oxidizing glucose with glucose oxidase or PQQ-glucose dehydrogenase as enzyme is between about −200 mV and +200 mV versus a Ag/AgCl reference electrode, and the most preferred mediators have redox potentials between about −100 mV and about +100 mV versus a Ag/AgCl reference electrode.

Transition Metal Complex Core Covalently Attached to a Polymer Backbone; [TMC-C]+[PB].

Figure 17:
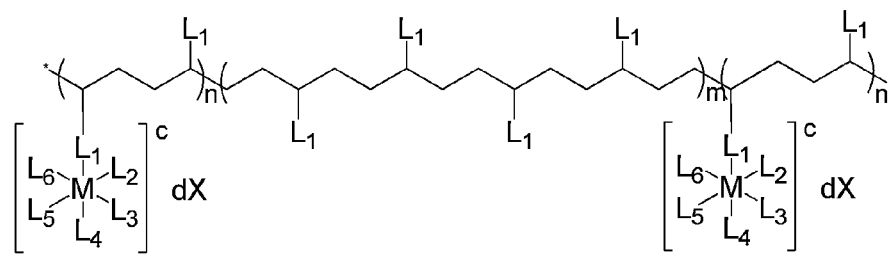
FIG. 17 illustrates a [TMC-C] bound to a [PB] where n=1 to 50 repeat units and m=1 to 100 repeat units.
Figure 18:
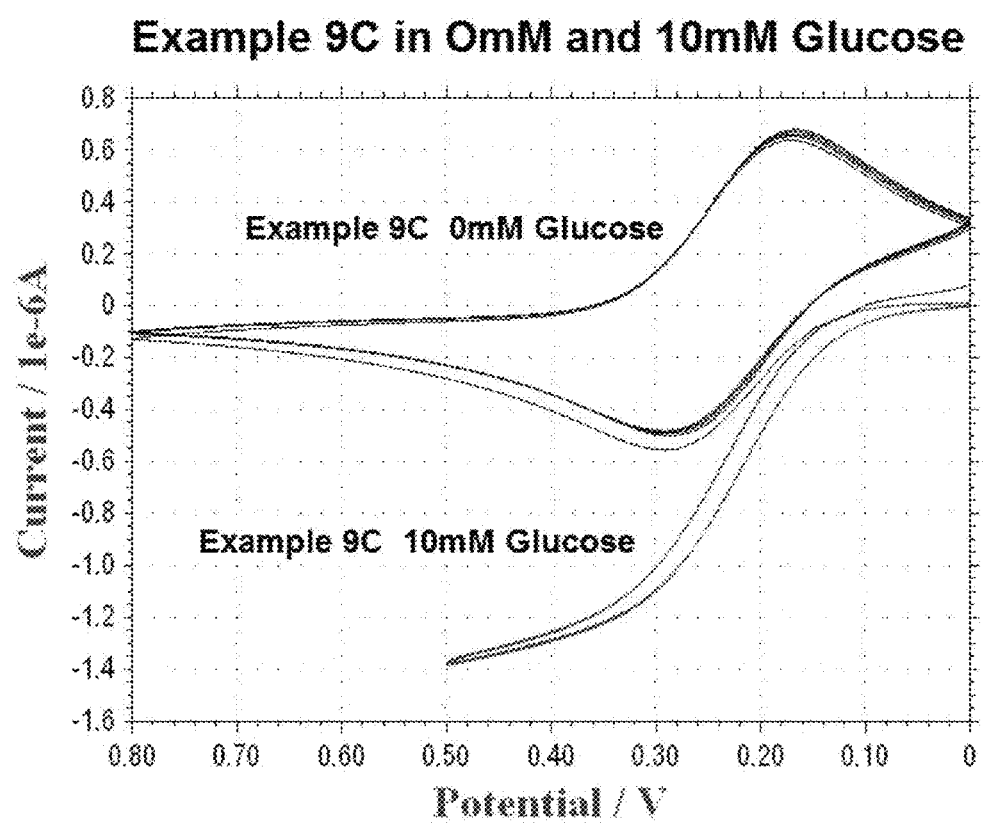
FIG. 18 illustrates BNPC cyclic voltametry results.

When the [TMC-C] of any of the possible types discussed herein are attached to a [PB] this is usually by a covalent bond to ensure that these components do not separate. Often a linker is used to obtain the spatial distance desired to allow the reactivity for N-SIS. See FIG. 17.

Dendritic Polymer [DP] Branching [BR]

Dendritic Polymers [DP] are well known as indicated by the above cited patents and references. In this invention the Dendritic Polymer is used to grow to nano-scale the TMC (of any of the types discussed above) using various surface reactive groups to covalently bind the Dendritic Polymer to the TMC.

A brief review if this dendritic branching is provided. Any nucleophilic (N), electrophilic (E) or other (O) reagent that is capable of reacting with the core [TMC-C], an extender [EX], with another branch cell or branch cell reagent [BR] or terminal functional group [TF]. Additionally, the [BR] reagent may be formed in situ from a precursor of a [BR]. These [BR] moieties must be able to undergo such a reaction and result in a covalent presentation of a multiplicity or amplification of reactive groups that [BR] of the lower generation product to grow the dendrimer to the next generation. (See, for example, U.S. Pat. No. 4,737,550.) The [BR] may react with a co-reactant to form a core adduct and further reacted with a second co-reactant. The co-reactants can be [TMC-C] as a core, [FF], [BR] or [EX]. Also the [BR] can be selected to react and form bonds with the [TMC-C] or terminal functionalities [TF] groups of the prior lower generation dendrimer which is now being further reacted to grow the next higher generation. Thus, any multifunctional [TMC-C] may also serve as a [BR]. When [BR] occurs in more than one generation, it may be the same or different [BR] moiety.

Examples of co-reactants for bonding with the electrophilic cores include nucleophilic moieties such as uncapped or partially protected polyamines both branched and linear, primary and secondary, DETA, IMAE, DEA, DBA, TETA, tetraethylenepentaamine, PEI, methylamine, BAA, hydroxyethylamine, octadecylamine, DEIDA, poly(methylenediamines) such as HMDA, polyaminoalkylarenes, tris(aminoalkyl)amines such as TREN, TRIS, linear and branched PEI, linear and branched PAMAM, heterocyclic amines such as imidazolines, piperidines, aminoalkyl PIPZ, PEA, PETGE, and various other amines such as hydroxyethylaminoethylamine, HEDA, mercaptoalkylamines, mercaptoethylamine, iminodialkynes, iminodiakenes, substituted PIPZ, amino derivatives of polyvinylbenzyl chloride and other benzylic amines such as tris(1,3,5-aminomethyl)benzene. Other suitable nucleophilic reactants include polyols such as pentaerythritol, ethylene glycol, polyalkylene polyols such as polyethylene glycol, polypropylene glycol, 1,2-dimercaptoethane and polyalkylene polymercaptans; thiophenols and phenols. Also suitable nucleophilic reactants are acetylenic polyepoxides, hydroxyalkyl azides, alkyl azides, tri- and tetra-aziridines, tri- and tetra-oxazolines, thiol alkyls, thiol [FF] dendrons, allyl groups, acrylates, methacrylates. Any of the above moieties may have olefinic functionality or capped moieties. Preferred are the triacrylate, tetraacrylates, triepoxide, tetraepoxide, diallyl amine, diethanol amine, diethyliminodiacetate, bis(2-haloalkyl)amine, tris(hydroxymethylamine), protected DETA, or methyl acrylate may be used, including in situ. Also preferred are one or more of cyclic ethers (epoxides), oxiranes, sulfides (epichlorosulfide), aziridines, azetidines, siloxanes, oxetanes, oxazolines, oxazines, carbamates, caprolactones, carboxyanhydrides, thiolactones, β-lactams, or derivatives thereof. More preferred are triacrylate, tetraacrylates, triepoxide, tetraepoxide, triazides, tetraazides, BAA, DEA, DEIDA, PETGE, PETriGE, PETriAE, HEDA, PEA, TREN, TRIS, dimethyliminodiacetate, protected DETA (with ketonic solvents), or methyl acrylate, including in situ.

Alternatively, a nucleophilic moiety can be reacted with an electrophilic reactant to form a core adduct [TMC+adduct] which is then reacted with a suitable second coreactant to form the dendrimer.

When [BR] is an other (O) moiety then some suitable reagents are those that may undergo free radical additions or participate in 1,3-cyclo-addition reactions, that is "click" chemistry that include but are not limited to acetylenic polyepoxides, hydroxyalkyl azides, alkyl azides, triazoles, thiol alkyls, thio [FF] dendrons, allyl groups, acrylates, methacrylates, or olefinic functionality.

When the [BR] moiety is part of a ring-opening reaction such [BR] may be cyclic ethers (epoxides), oxiranes, sulfides (epichlorosulfide), aziridines, azetidines, siloxanes, oxetanes, oxazolines, oxazines, carbamates, caprolactones, carboxyanhydrides, thiolactones, and betalactams. When this reaction occurs, in addition to the branching function, the [BR] may also form an [IF] in situ as a result of unreacted groups left on the [BR].

Preferred [BR] moieties are triacrylate, tetraacrylates, triepoxide, tetraepoxide, diallyl amine (BAA), diethanol amine (DEA), diethyliminodiacetate (DEIDA), tris(hydroxymethylamine), PETGE, HEDA, PEA, TREN, TRIS, dimethyliminodiacetate, and protected DETA (with ketonic solvents). Additionally, methyl acrylate may be used, as an electrophilic reagent to generate [BR] in situ by addition to amines or thiols.

In this manner the [TMC-C] are reacted with [BR] and/or [EX] to form a dendritic layer around the core and grow outward to the desired [G] with [SF] terminal surface functionality groups.

Dendritic Polymer with Interior Functionality [IF]

Interior functionality [IF] is a unique feature of the PEHAM dendrimers created by the reaction of appropriate branch cell reagents leading to the [BR] that are growing from generation to generation, G. The interior reactive sites, (i.e. hydroxyl, sulfhydryl, amine, phosphine, alkylsilane, silane, boranes, carboxyl, carboxyl ester, chloro, bromo, alkene, alkyne, or alkyl- or aryl-amide, etc.) result from the ring-opening reactions. This provides an interior covalent chemistry handle which may be further reacted, while maintaining the important internal functionality suitable for association with a further group, chelation or encapsulation. [IF] also provide unique attachment sites for adjusting the hydro-phobic/hydrophilic features of the interior of the Dendritic Polymer, for introduction of polymerization initiators or sites, or for attachment of or association with therapeutic entities as pro-drugs. Preferred [IF] moieties are hydroxyl, thiol, an alkylene ester and amine.

Dendritic Polymer Extender [EX]

Extenders [EX] may be present in the interior of the dendrimer. They provide a means to lengthen the distance and thereby increase the space between the core [TMC-C] and subsequent generations, G, of the dendrimer and preferably must have two or more reactive sites, unless the [EX] is in the last G when it can have one reactive site and effectively terminates further G growth or caps the Dendritic Polymer for [TF] or only partially caps it. These enhancements in interior space volume increase the capacity for the dendrimer to encapsulate carrier materials [CM] further described below. These [EX] may occur prior to or after the [BR] moiety or both prior to and after the [BR] moiety. These [EX] may also have an [IF] moiety present. These [EX] have at least two reactive sites and optionally may contain an [IF] or may form [IF] in situ. It is possible to consecutively react [EX] before any other reaction in any G; and in that case [EX] may be the same or different.

Preferred extenders [EX] are poly(amino acids) such as polylysine, other poly(amino acids), lysine, other amino acids, oligoethyleneglycols, diethylenetetraamine and higher amine analogs, oligoalkylenamines protected as 5-membered imidazolidyl derivatives [see Araki et al., 21(7), 1995-2001 (1988)], fatty acids with di- or greater heterogeneous or homogenous functionality, unsaturated aliphatic and aromatic difunctional or polyfunctional moieties, EA, morpholine, dicarboxylic acids, EPC, 1,2,3-triazoles, IMAE, aryl dimercaptans, dimercaptoalkanes, DMI, diazides, diacetylenes, pyrrolidone, pyrrolidone esters, aminoalkyl imidazolines, imidazolines, poly(alkyleneimidazolidines), mercaptoalkylamines, hydroxyalkylamines, and heterogeneous unsaturated aliphatic and aromatic difunctional or polyfunctional moieties (e.g., imidazolidyl moieties).

Additional preferred [EX] are diaminoalkanes, diphenols, dithiophenols, aromatic poly(carboxylic acids), mercaptoamines, mercaptoethanol, allylamines, PEA, PIPZ, polyP-IPZs, AEP, EPC, cyclic pyrrolidine derivatives, EDA, DEIDA, and hyperbranched dendritic polymers such as those derived from polylysine, poly(esteramide), hyperbranched dendritic polymers such as those derived from polylysine, poly(esteramide), poly(amidoamine), poly(ethyleneimine) or poly(propyleneimine) moieties. More preferred are PEA, DMI, methyl acrylate, EPC, 1,2,3-triazoles, IMAE, PIPZ, aminoalkyl piperazines, poly-(alkylenepiperazines), diamines possessing disulfide moieties, MIPIEP, bis(piperazinoalkyl)disulfides, and piperazine derivatives.

Dendritic Polymer Surface Functionality [SF]

Terminal functional groups [SF] are moieties that are sufficiently reactive to undergo addition or substitution reactions, or ring-opening, or any functionally active moiety that can be used to propagate the dendritic branch to the next generation including but not limited to free radical and 1,3-dipolar cyclo-addition reactive moieties. Some but not all [SF] moieties may react to form the next generation, G, dendrimer and the [SF] groups may be the same or different. The [SF] can be polymer initiation groups. When the [SF] moiety is the last G, then that [SF] may be unreactive. The (y) term refers to the number of surface groups mathematically defined by the G.

Some examples of such terminal groups [SF] are, including but not limited to, amino groups [including primary and secondary, which may be capped, but has at least one uncapped amino group present (e.g., methylamino, ethylamino, hydroxyethylamino, hydrazino groups, benzylamino, glucosamine, an amino acid, mercaptoethylamino), tertiary amino (e.g., dimethylamino, diethylamino, bis(hydroxyethyl)amino), quaternary amino groups, trialkyl ammonium, bis (hydroxyethyl)amino, bis(2-haloethyl)amino, N-alkylated, N-arylated, N-acylated derivatives]; hydroxyl, mercpato, carboxyl, alkenyl, allyl, aryl, meth-alkyl, vinyl, amido, halo, urea, oxiranyl, aziridinyl, oxazolinyl, azalactone, lactam, lactone, imidazolinyl, sulfonato, phosphonato, boronato, organosilanes, isocyanato, isothiocyanate, hydroxy alkylazido, and a-haloacyl groups. The number of carbons present for these hydrocarbon groups is from 1 to 25. Terminal groups may be substituted with other groups using conventional procedures. [See, for example, U.S. Pat. Nos. 4,507,466; 4,558, 120; 4,631,337.]

Preferred surface groups [SF] are polyethyleneglycol, pyrrolidone, pyrrolidone esters, carboxypiperidines, piperidines, piperazines, substituted piperazines, aminoalkyl piperazines, hexylamides, aldehydes, azides, oxetanes, dyes (e.g., near infrared fluorchromes such as cyanine derivatives, FITC), colorimetric (e.g., Nile red), tris(hydroxymethyl)amidomethane, photochromic moieties (e.g., sydnones, phorphines), amidoethylethanolamines, carbomethoxypyrrolidinone, succinamic acid, amidoethanol, amino acids, protected amino acids, antibodies and fragments, proteins, peptides, cyclopeptides, cationic steroids, macrocyclic groups, azacrown ethers, antibiotics/antibacterials [e.g., aminoglycosides, amphenicols, ansamycins, β-lactams (such as penicillin, cephalosporins, cephamycins, oxacephems, carbapenems), tetracyclines, macrolides, lincosamides, 2,4-diaminopyrimidines, nitrofurans, quinolones, sulfonamides, sulfones], antineoplastics [e.g., alkyl sulfonates, aziridines, epoxides, ethyleneimines and methylmelamines, nitrogen mustards, nitroureas, purine analogs, androgens, antiadrenals, antiandrogens, antiestrogens, estrogens, LHRH analogs, progestogens and others], folic acid and analogs, epoxides, acrylates, methacrylates, amines, carboxylates, cationic, anionic, neutral, aromatic, glucosamine or other amino sugars, biotin, avidin, streptavidin, growth factors, hormones, aptamers, DOTA, DTPA, metal chelates, naphthyl sulfonates, alkyl sulfonates, aryl sulfonates, targeting groups (e.g., CD19, CD22, aptamers), hyaluronic acid, polyoxometalates, organic chromophores, polyvalent attached compounds, carbon nanotubes, fullerenes, nano-composites, all metal nanoparticles, all semiconductor nano-particles with all varieties of cores and shells, radioactive materials and their chelated analogues, fluorescent molecules (metal salts, organic compounds), electrically conductive molecules, light or electromagnetic energy absorbing or emitting molecules (such as UV, VIS (visible), IR and microwave), radioactive analogues of drugs or diagnostic agents, silanes, siloxanes, silsesquioxane, poly(aryl-alkyl) poly(iodides), quantum dots, nanocrystals (e.g., Au, Ag, Cu, etc.), polyfluorinated molecules, surfactants, dendrons, differentiated dendrons, dendrimers, methoxy ethoxy ethoxy, polyimides (e.g., maleimide), herbicides (e.g., trifluralin, 2-phosphonomethylamino acetic acid), polyazo compounds, polyphosphazine, polyfluorinated sulfonates, heteroatoms chains and branches, lipids, starches, simple sugars (e.g., mannose, dextrose), oligonucleotides, complex sugars, drugs, such as anti-cancer agents (e.g., doxorubicin, methotrexate, others), acetylsalicylic acid, salicylic acid, vitamins (e.g. vitamin E, C), cofactors (e.g. NADH), or antioxidants. [SF] can be further reacted with any carried material [CM] that can be associated with the [SF] entity and may be from one [CM] to the maximum possible z present on the surface, only limited by N-SIS. Additionally some [SF] can be further reacted with [BR] or [EX] to grow the surface more.

Also, preferred [SF] groups are PIPZ and its derivatives, alkyl PIPZ, aminoalkyl PIPZ, 1,2,3-triazoles, IMEA, acrylate, methacrylate, acrylamides, alkynes, hydroxyl, epoxide, oxazoline, alkyleneimines, lactones, azalactones, polyethylene oxides, amino, ethyl imines, carboxylates, alkyl, aziridine, azides, ethyl imines, alkyl esters, epoxides, alcohol groups, alkylthiols, thiols, thioranes, morpholines, amines, hydrazinyl, carboxyl, allyl, azidyl, alkenyl, alkynyl, hydroxylalkylamino, protected DETA, carboxyalkyl, pyrrolidone (and its esters), and succimidyl esters. Especially preferred are PIPZ, aminoalkyl PIPZ, alkyl PIPZ, PIPZ derivatives, and triazoles.

Dendritic Polymer Growth, G

Divergent dendritic growth can be precisely controlled to form ideal dendritic polymers which obey mathematical formulas, at least through the first several generations of growth. However, because the radii of dendrimer molecules increase in a linear manner as a function of generation during ideal divergent growth, whereas the surface cells amplify according to a geometric progression law, ideal dendritic growth does not extend indefinitely. There is a critical generation at which the reacting dendrimer surface does not have enough space to accommodate incorporation of all of the mathematically required new units. This stage in digression from ideal dendritic growth is referred to as the de Gennes dense-packed stage. At this stage, the surface becomes so crowded with terminal functional groups that, although the terminal groups are chemically reactive, they are sterically prohibited from participating further in ideal dendritic growth. In other words, the de Gennes dense-packed stage is reached in divergent dendrimer synthesis when the average free volume available to the reactive terminal group decreases below the molecular volume required for the transition state of the desired reaction to extend the dendritic growth to the next generation. Nevertheless, the appearance of the de Gennes dense-packed stage in divergent synthesis does not preclude further dendritic growth beyond this point. It has been demonstrated by mass spectrographic studies that further increase in the molecular weight can occur beyond the de Gennes dense-packed stage. However, this occurs in a non-ideal fashion that no longer adheres to values predicted by dendritic mathematics.

Products resulting from continuation of dendritic growth beyond the dense-packed stage are "imperfect" in structure, because some of the surface groups in the precursor generation are sterically precluded from undergoing further reaction. The number of functional groups on a dendrimer which has been grown past the de Gennes dense-packed stage will not correspond to the ideal, mathematically predicted value for that generation. This discontinuity is interpreted as a signature for the de Gennes dense-packed stage.

Radioactive Isotopes

The moieties [TMC-C], [BR], [IF], [RS] and [EX] can contain atoms that are radioactive isotopes when desired. For example, $^3H$ or $^{14}C$ can be used to trace the location of the BNPC in a biopathway or location of by-product or metabolite of the BNPC. Thus prepared, the BNPC of Formula 2 can be reacted with a wide variety of compounds to produce polyfunctional compounds with unique characteristics. For example, a BNPC having terminal amine moieties may be reacted with unsaturated nitriles to yield a polynitrile, or with an α,β-ethylenically unsaturated amide to form a polyamide, a, β-ethylenically unsaturated ester to form an ester terminated BNPC, an oxirane to form a polyol, ethylenically unsaturated sulfide to form a thiol terminated BNPC. A BNPC having terminal hydroxyl moieties may be reacted with a carboxylic acid to form an ester terminated BNPC, with an alcohol or alkylhalide to form an ether terminated BNPC, with isocyanate to form a urethane terminated BNPC, with thionyl chloride to a chloride terminated BNPC, and with tosylate to form a tosyl-terminated BNPC.

TMC or BNPC Enzyme Receptors [SF]

Proper selection of the [RS] groups of ligands [L] can greatly enhance the electron transfer properties of the TMC. TMC that generate negative voltages are particularly useful for anodes, while TMC that generate positive voltages are particularly useful for cathodes. Further coupling a negative voltage TMC with a reducing enzyme such as glucose oxidase (GOX) or lactate oxidase (LOX) can further enhance the anode's negative voltage, while coupling a positive voltage TMC with an oxidizing enzyme such as bilirubin oxidase (BOD) can further enhance the cathode's positive voltage.

Redox potentials of the preferred TMC Redox Mediators used for electro-oxidizing glucose with glucose oxidase or PQQ-glucose dehydrogenase as enzyme is between about −200 mV and +200 mV versus a Ag/AgCl reference electrode, and the most preferred mediators have redox potentials between about −100 mV and about +100 mV versus a Ag/AgCl reference electrode.

BNPC Targeting Receptors

Other receptors can be attached to the [SF] moieties of the BNPC to promote attraction of the BNPC to specific target sites. Once the BNPC has been attracted to the target site, its active enzyme receptors (above) can generate power to deliver [CM] to the target site. In some cases, the generation of localized power to the target site will have therapeutic properties, without the need to deliver [CM].

BNPC as Power Cells

The major components that make BNPC useful for the present invention are the TMC that transfer electrons and power generation and the Dendritic Polymer structure that protects the TMC for biocompatibility and [CM] delivery, Formula 2 above.

Figure 7:
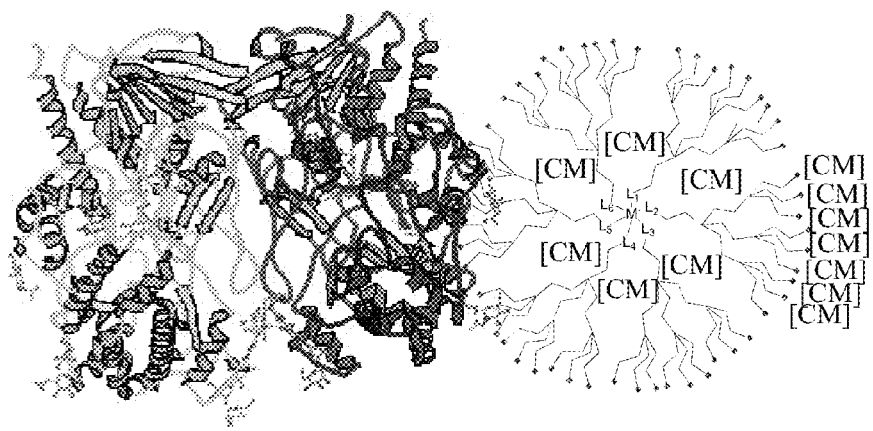
FIG. 7 illustrates a targeting receptor moiety that is quite large, even larger than the BNPC.

As illustrated by FIG. 7, some of the targeting receptor moieties can be quite large, even larger than the [TMC-C] and Dendritic Polymer of the BNPC.

Figure 8:
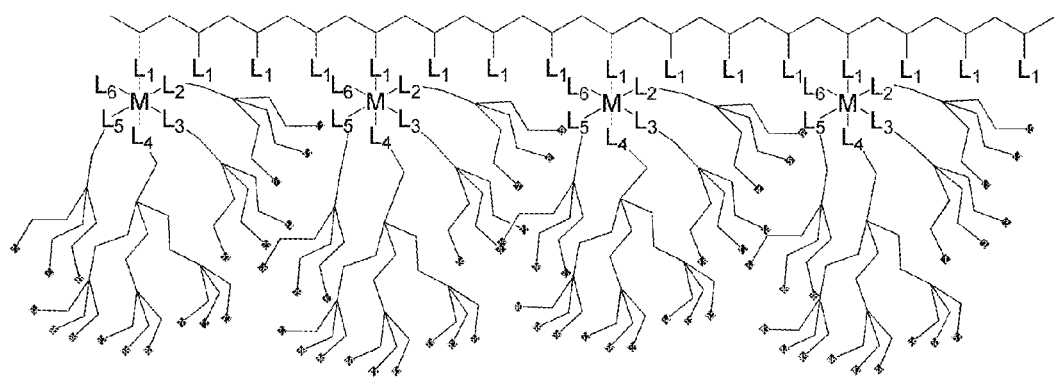
FIG. 8 illustrates a BNPC wherein the [TMC-C] has one of its ligands [L] as a polymer.

In the FIG. 8, only the first layer of Dendritic Polymer is shown; additional layers can be added and the epoxide moieties can be functionalized to improve solubility and biocompatibility. The small circles are meant to depict enzymes or other targeting groups. These moieties are not to scale as enzymes are generally larger than the BNPC entity.

An example of the TMC wherein one of the ligands [L] is a polymer is shown in the BNPC of FIG. 8. This molecule can be further polymerized to form larger molecules. In FIG. 8, only the first layer of Dendritic Polymer is shown; additional layers can be added and the epoxide moieties can be functionalized to improve solubility and biocompatibility.

BNPC-Electron Transport

Electron transport involves an exchange of electrons between segments/components of the BNPC (e.g., one or more [TMC-C] coupled to a Dendritic Polymeric as a backbone, as described above) in a film disposed on an electrode. The BNPC can be bound to the Dendritic Polymer backbone though covalent, coordinative or ionic bonds, where covalent and coordinative binding are preferred. Electron exchange occurs, for example, through the collision of different segments of the Dendritic Polymer and the [TMC-C]. Electrons transported through the Dendritic Polymer can originate from, for example, electro-oxidation or electro-reduction of an enzymatic substrate, such as, for example, the oxidation of glucose by glucose oxidase. Thus the [CM] is an enzyme in a BNPC-[CM] entity.

Preferred anode enzymes for the electro-oxidation of the anode reductant include, for example, PQQ glucose dehydrogenase, glucose oxidase, galactose oxidase, PQQ fructose dehydrogenase, quinohemoprotein alcohol dehydrogenase, pyranose oxidase, oligosaccharide dehydrogenase, and lactate oxidase.

Preferred cathode enzymes for the electro-reduction of the cathode oxidant include, for example, tyrosinase, horseradish peroxidase, soybean peroxidase, other peroxidases, laccases, RuBisCo, and/or cytochrome C peroxidases.

The choice of Dendritic Polymer can influence the transport of electrons or ions and thereby the rates of the electrochemical reactions. A reduction in segment mobility can slow the diffusion of electrons or ions through the Dendritic Polymer film. A reduction in the diffusivity of electrons, for example, can require a concomitant reduction in the thickness of the film on the electrode, where electrons or electron vacancies are collected or delivered. For example, $Os^{2+/3+}$ metal [TMC-C] with a dendrigraft or PEHAM as the Dendritic Polymer facilitates the transport of electrons to the electrode. Because the [TMC] can be interior in the Dendritic Polymer this BNPC can reduce leaching and shear problems of the film on the electrode. Because a dendrigraft can carry many [TMC] moieties, it makes more [TMC] groups available for use and the number can be regulated.

Figure 9:
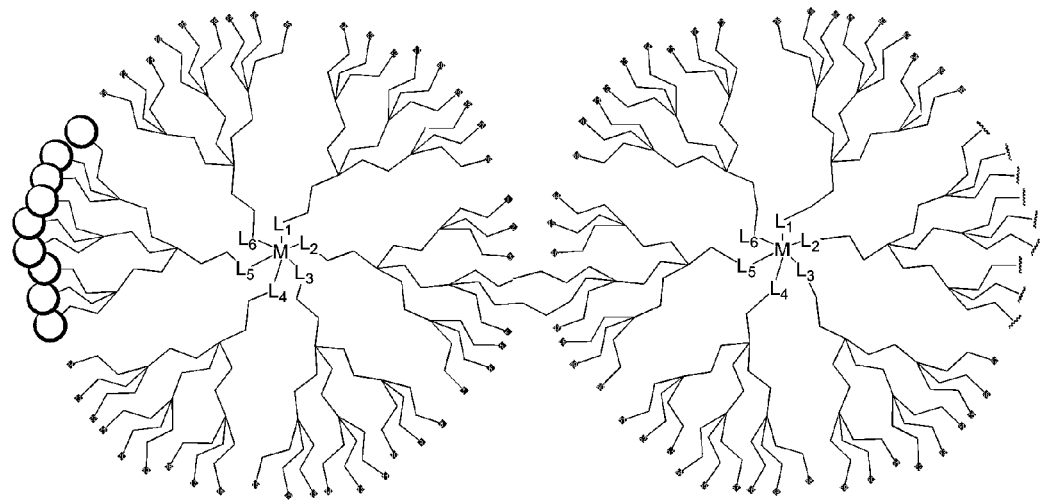
FIG. 9 illustrates a BNPC Dimer Aggregate–2 BNPC covalently joined.
Figure 10:
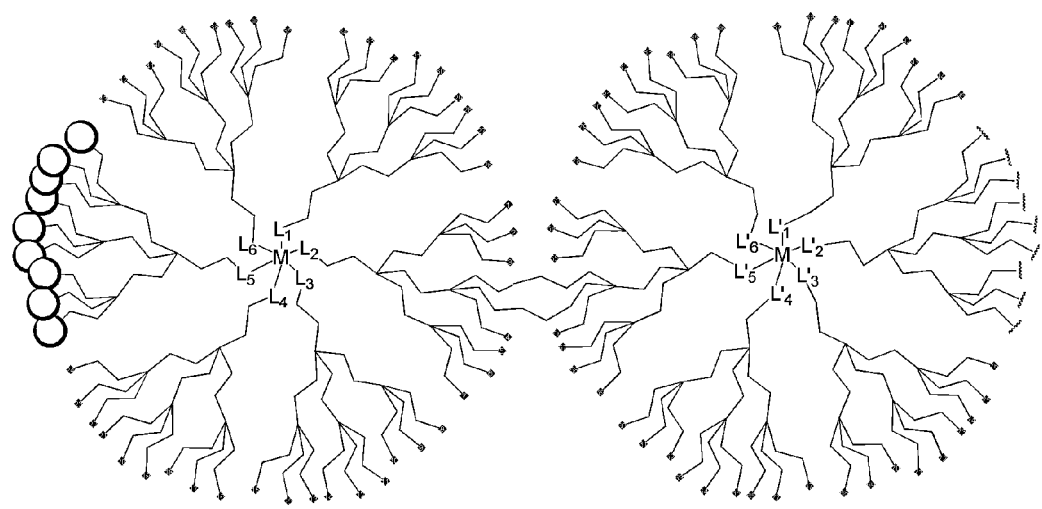
FIG. 10 illustrates a BNPC Anode-Cathode Aggregate and would have different enzymes or different ligands present on different parts of the molecule.
Figure 11:
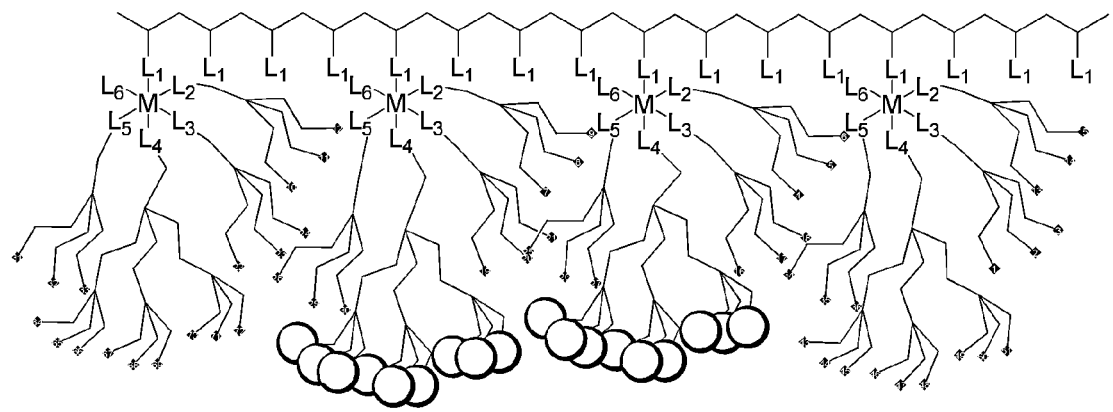
FIG. 11 illustrates a BNPC Polymeric Aggregate.

Use of the Dendritic Polymers yields a more uniform rod-like structure (e.g., sphere-like structures in a row, rods, or dendrigrafts) with sufficient biocompatibility so that a separate membrane layer or other layer is not required. This molecule can be further polymerized to form larger molecules. Various BNPC can be used for this purpose such as a BNPC Dimer Aggregate (FIG. 9), a BNPC Anode-Cathode Aggregate (FIG. 10), and a BNPC Polymeric Aggregate (FIG. 11). These molecules can be polymerized into larger molecules that have unique geometric shapes, such as sheets, aggregates, larger spheres, rods, etc. that are at least nano-scale.

BNPC for Carried Material [CM] Delivery

Figure 12:
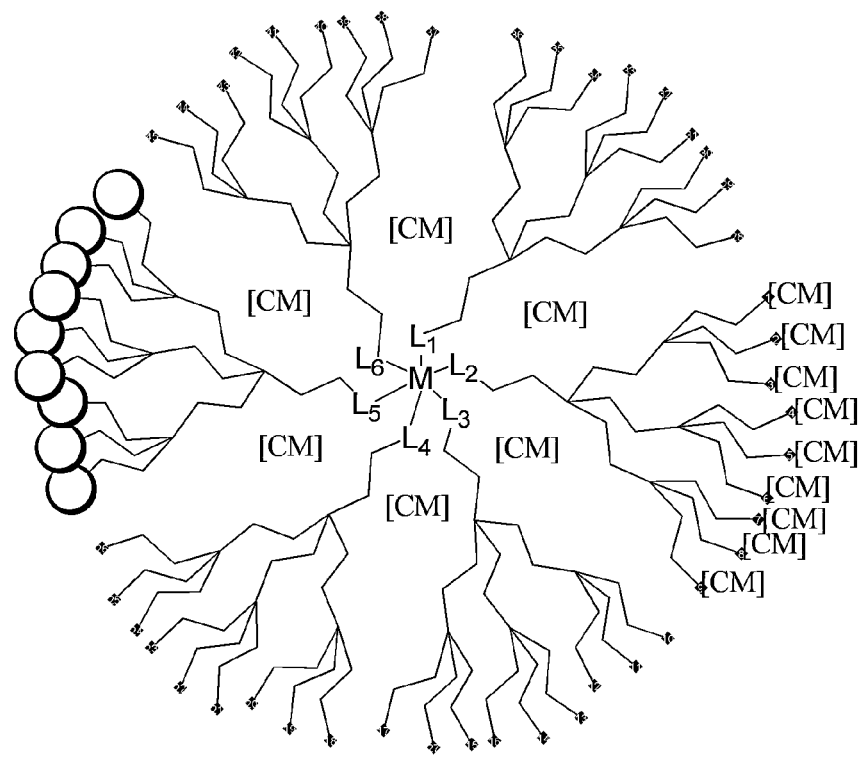
FIG. 12 illustrates a BNPC Conjugate or BNPC+[CM] or [TMC-C]+Dendritic Polymer+[CM].
Figure 13:
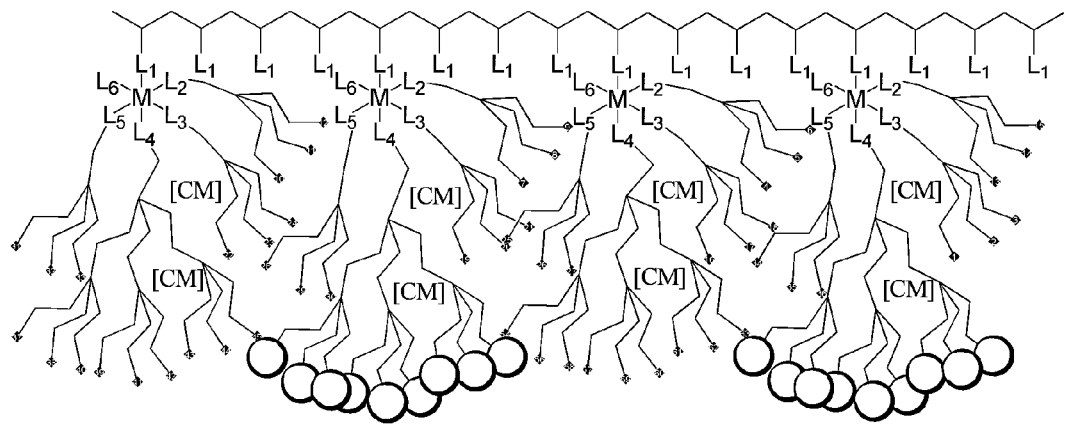
FIG. 13 illustrates a BNPC Polymeric Conjugate or BNPC+[CM]+Polymer Backbone (dendrigraft).
Figure 14:
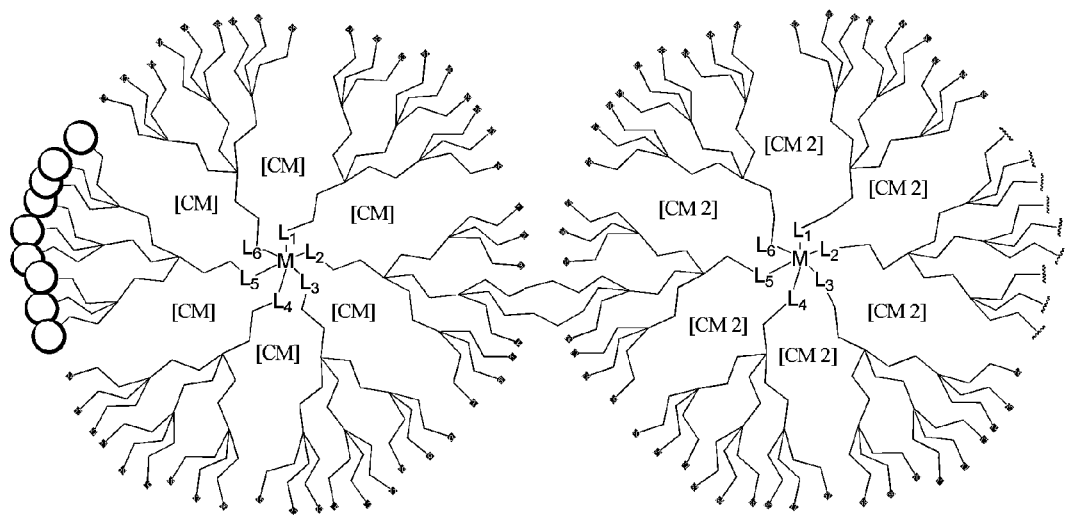
FIG. 14 illustrates a BNPC Dimer Aggregate Conjugate or 2 BNPC+[CM].
Figure 15:
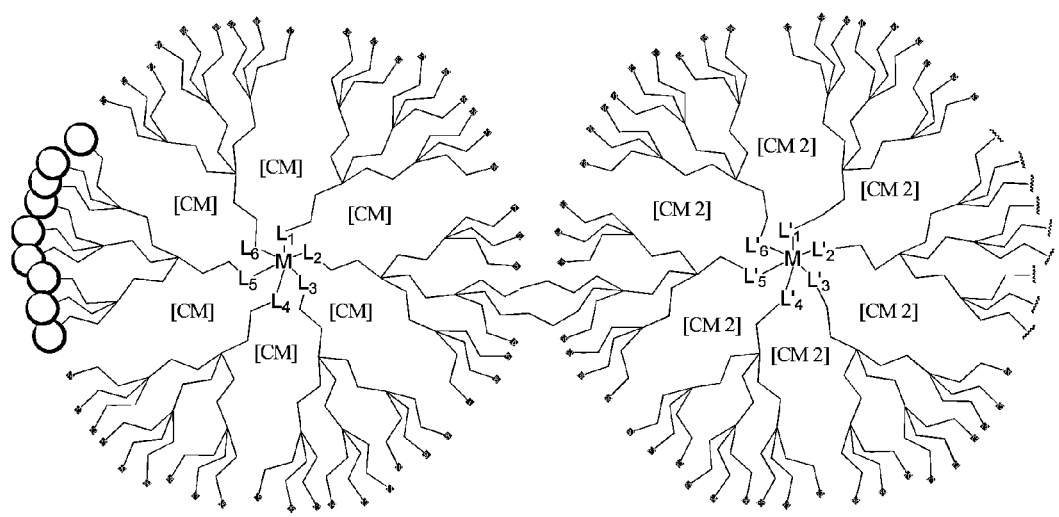
FIG. 15 illustrates a BNPC Anode-Cathode Aggregate Conjugate and would have different enzymes or different ligands present on different parts of the molecule.
Figure 16:
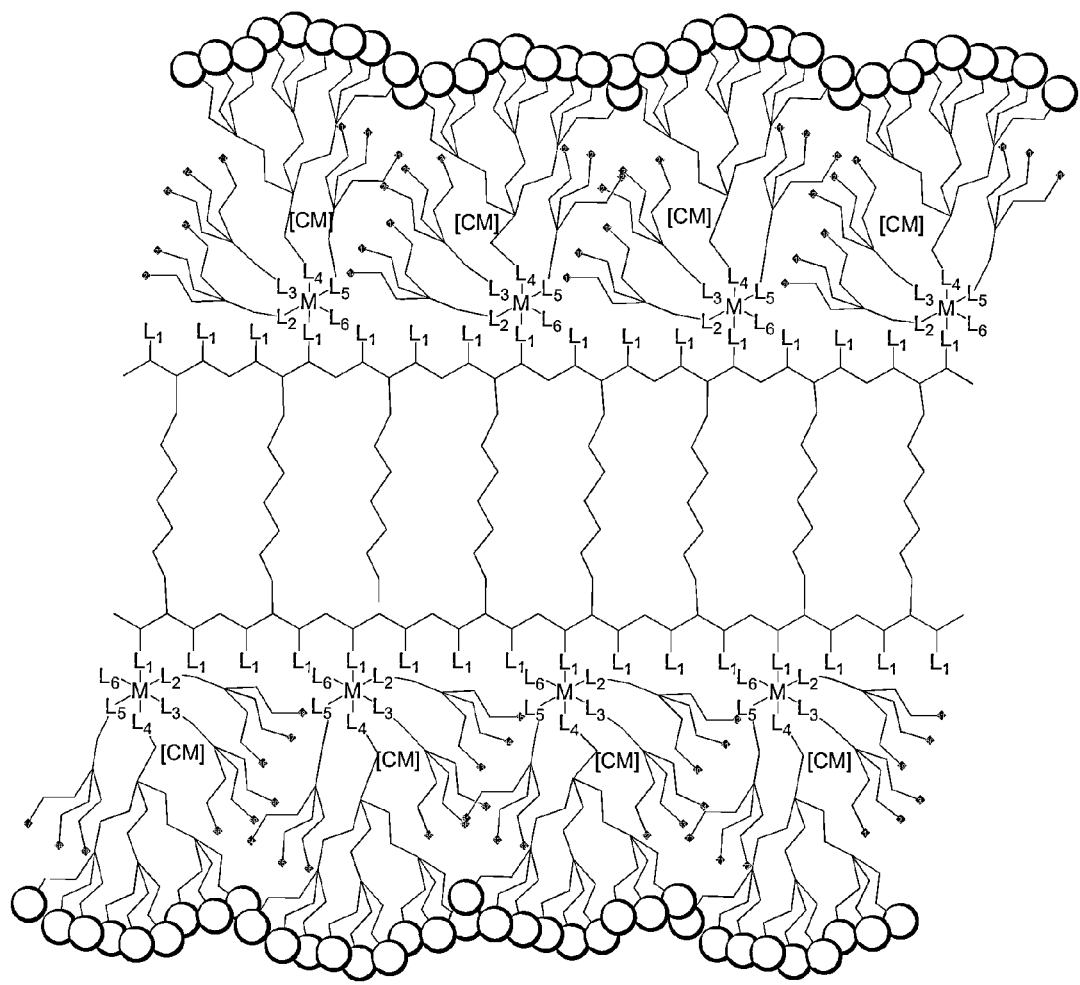
FIG. 16 illustrates a BNPC Polymeric Aggregate Conjugate or 2 BNPC+[CM]+Polymer Backbone (dendrigraft).

For carried material [CM] delivery applications, [CM] can be attached and/or encapsulated by this drug delivery molecule. The BNPC can be activated by the targeting receptor moieties to facilitate "on-demand" [CM] delivery. Thus the electrical power that flows from [TMC] upon stimulus from the biosystem, such as the presence of an analyte or enzyme will trigger the delivery of the [CM] from the BNPC. This offers a unique delivery system that releases the [CM] only when needed—"on demand". The BNPC system is illustrated by BNPC Conjugate (FIG. 12), BNPC Polymeric Conjugate (FIG. 13), BNPC Dimer Aggregate Conjugate (FIG. 14), BNPC Anode-Cathode Aggregate Conjugate (FIG. 15), and BNPC Polymeric Aggregate Conjugate (FIG. 16).

BNPC Power Generation

The combination of TMC and Dendritic Polymers yields BNPC nanoparticles that can generate an electrical charge when activated by a targeting group. TMC, that transfer electrons to generate power, generally have redox potentials in a particular range, exchange electrons rapidly, and transfer electrons to or accept electrons from an enzyme or other analyte-specific redox catalyst. Glucose oxidase (GOX), lactate oxidase (LOX) or bilirubin oxidase (BOD) are particularly useful to accelerate the kinetics of electro-reduction or electro-oxidation.

BNPC with simple and multiple [TMC-C] are particularly useful for localized power generation. Localized power generation is useful for therapeutic, carried material [CM] delivery and other applications.

BNPC with multiple, scaffolding, or super [TMC-C] are particularly useful for distributed power generation. Distributed power generation is useful for biosensor, biofuel cell, carried material [CM] delivery and other applications.

BNPC for Localized Power Generation: [TMC-C], [m-TMC-C]

These BNPC are useful for therapeutic applications and with carried material [CM] delivery for in vivo localized use.

BNPC are very useful for transporting carried materials [CM] such as therapeutics to targeted sites; when the transition metal complex core is activated by an enzyme receptor, the energized BNPC releases the therapeutic "on-demand". This property is particularly useful for scavenging metastatic cancer cells so that cancer therapeutics can be delivered only at the targeted site, thus reducing the need for systemic cancer treatments. The wide variety of targeting receptors, enzyme receptors and carried materials make BNPC's localized power distribution properties useful for a broad range of applications.

BNPC are also useful generating therapeutic levels of energy at targeted sites; when the transition metal complex core is activated by an enzyme receptor, the BNPC molecule becomes energized, providing therapeutic properties.

BNPC for Distributed Power Generation: [m-TMC-C], [s-TMC-C], [sp-TMC-C]

BNPC Biosensors:

The BNPC discussed above are useful as Redox Mediators in electrochemical sensors for the detection of analytes in bio-fluids. The BNPC that include a polymeric backbone and are Redox Mediators can also be referred to as "Redox Polymeric Power Cells". Redox Mediators may accelerate the electro-oxidation of glucose in the presence of glucose oxidase or PQQ-glucose dehydrogenase; a process that can be useful for the selective assay of glucose in the presence of other electrochemically oxidizable species. Compounds having the Formula 1 are examples of TMC of the present invention. In general, the Redox Mediator is disposed on or in proximity to (e.g., in a solution surrounding) a working electrode. The Redox Mediator transfers electrons between the working electrode and an analyte. In some additional embodiments, an enzyme is also included to facilitate the transfer. For example, the Redox Mediator transfers electrons between the working electrode and glucose (typically via an enzyme) in an enzyme-catalyzed reaction of glucose. Redox polymers are particularly useful for forming non-leachable coatings on the working electrode. These can be formed, for example, by crosslinking the redox polymer on the working electrode, or by crosslinking the redox polymer and the enzyme on the working electrode.

BNPC can enable accurate, reproducible and quick or continuous assays. TMC Redox Mediators accept electrons from, or transfer electrons to, enzymes or analytes at a high rate and also exchange electrons rapidly with an electrode. Typically, the rate of self exchange, the process in which a reduced Redox Mediator transfers an electron to an oxidized Redox Mediator, is rapid. At a defined Redox Mediator concentration, this provides for more rapid transport of electrons between the enzyme (or analyte) and electrode, and thereby shortens the response time of the sensor. Additionally, the novel TMC Redox Mediators are typically stable under ambient light and at the temperatures encountered in use, storage and transportation. Preferably, the TMC Redox Mediators do not undergo chemical change, other than oxidation and reduction, in the period of use or under the conditions of storage, though the Redox Mediators can be designed to be activated by reacting, for example, with water or the analyte.

The TMC can be used as a Redox Mediator in combination with a redox enzyme to electro-oxidize or electro-reduce the analyte or a compound derived of the analyte, for example by hydrolysis of the analyte. The redox potentials of the Redox Mediators are generally more positive (i.e. more oxidizing) than the redox potentials of the redox enzymes when the analyte is electro-oxidized and more negative when the analyte is electro-reduced. For example, the redox potentials of the preferred TMC Redox Mediators used for electro-oxidizing glucose with glucose oxidase or PQQ-glucose dehydrogenase as enzyme is between about −200 mV and +200 mV versus a Ag/AgCl reference electrode, and the most preferred mediators have redox potentials between about −100 mV and about +100 mV versus a Ag/AgCl reference electrode.

BNPC for Biofuel Cells:

Producing electrical power from energy sources available in biological systems has long been desired. As availability of traditional energy systems diminish, compounds and systems that efficiently convert energy rich compounds found in biological systems offer seemingly unlimited potential for energy production. Transition metal complexes described above can also be used for the preparation of biological fuel cells (e.g., U.S. Pat. Nos. 6,294,281; 6,531,239; 7,018,735; 7,238,442 and US Published Patent Appls. 20070248850 and 20080044721). Anode enzymes (e.g., oxidase or dehydrogenase) and cathode enzymes (e.g., laccase, ascorbate oxidase, creuloplamine or bilirubin oxidase) have been used to demonstrate that efficient biofuel systems can be produced by transition metal complexes in laboratory scale systems. Larger commercial systems require improved biocompatibility and design versatility that BNPC can provide much better than previous systems. Building the biocompatibility and aggregation ability into the building block molecules makes BNPC particularly useful for preparing biofuel cells. These BNPC biofuel cells are particularly useful for alternative energy generation, powering implanted medical devices and delivering carried materials.

BNPC Excipient:

An excipient in this invention is defined as a material that interacts with the pharmaceutical active material [CM] and enhances its solubility in the desired solvent. In addition, the presence of the excipient might alter the pharmacological profile of the respective drug, reduce its toxicity or its retention time within the body, although these activities are not its main purpose. Any known excipients can be used with the BNPC for the use intended.

Drug [CM] Associated with Dendritic Polymers of the BNPC:

As used herein "associated with" means that the carried material(s) [CM] can be physically encapsulated or entrapped within the interior of the Dendritic Polymer, dispersed partially or fully throughout the Dendritic Polymer, or attached or linked to the Dendritic Polymer or any combination thereof, whereby the attachment or linkage is by means of covalent bonding, hydrogen bonding, adsorption, absorption, metallic bonding, van der Walls forces or ionic bonding, or any combination thereof. The association of the carried material(s) [CM] and the Dendritic Polymer may optionally employ connectors and/or spacers or chelating agents to facilitate the preparation or use of these conjugates. Suitable connecting groups are groups which link a targeting director (i.e., T) to the Dendritic Polymer (i.e., dendrimer) without significantly impairing the effectiveness of the director or the effectiveness of any other carried material(s) (i.e., [CM]) present in the combined BNPC-[CM] ("conjugate"). These connecting groups may be cleavable or non-cleavable and are typically used in order to avoid steric hindrance between the target director and the Dendritic Polymer, preferably the connecting groups are stable (i.e., non-cleavable) unless the site of delivery would have a cleavable linker present (e.g., an acid-cleavable linker at the cell surface). Since the size, shape and functional group density of these dendrimers can be rigorously controlled, there are many ways in which the [CM] can be associated with the Dendritic Polymer. For example, (a) there can be covalent, coulombic, hydrophobic, or chelation type association between the [CM](s) and entities, typically functional groups, located at or near the surface of the Dendritic Polymer; (b) there can be covalent, coulombic, hydrophobic, or chelation type association between the [CM](s) and moieties located within the interior of the Dendritic Polymer; (c) the Dendritic Polymer can be prepared to have an interior which is predominantly hollow allowing for physical entrapment of the [CM] within the interior (void volume), wherein the release of the [CM] can optionally be controlled by congesting the surface of the Dendritic Polymer with diffusion controlling moieties, (d) where the Dendritic Polymer has internal functionality groups [IF] in a PEHAM dendrimer present which can also associate with the [CM], or (e) various combinations of the aforementioned phenomena can be employed.

Definition of Carried Material [CM] Associated with Dendritic Polymer of BNPC:

The carried material [CM] that is encapsulated or associated with these Dendritic Polymers may be a very large group of possible moieties that meet the desired purpose. Such materials include, but are not limited to, pharmaceutical materials for in vivo or in vitro or ex vivo use as diagnostic or therapeutic treatment of animals or plants or microorganisms, viruses and any living system, which material can be associated with these Dendritic Polymers without appreciably disturbing the physical integrity of the BNPC.

In a preferred embodiment, the carried materials, herein represented by [CM], are pharmaceutical materials. Such [CM] which are suitable for use in the present BNPC-[CM]

conjugates include any materials for in vivo or in vitro use for diagnostic or therapeutic treatment of mammals which can be associated with the Dendritic Polymer without appreciably disturbing the physical integrity of the BNPC, for example: drugs, such as antibiotics, analgesics, hypertensives, cardiotonics, steroids and the like, such as acetaminophen, acyclovir, alkeran, amikacin, ampicillin, aspirin, bisantrene, bleomycin, neocardiostatin, chloroambucil, chloramphenicol, cytarabine, daunomycin, doxorubicin, cisplatin, carboplatin, fluorouracil, taxol, gemcitabine, gentamycin, ibuprofen, kanamycin, meprobamate, methotrexate, novantrone, nystatin, oncovin, phenobarbital, polymyxin, probucol, procarbabizine, rifampin, streptomycin, spectinomycin, symmetrel, thioguanine, tobramycin, trimethoprim, and valbanl; toxins, such as diphtheria toxin, gelonin, exotoxin A, abrin, modeccin, ricin, or toxic fragments thereof; metal ions, such as the alkali and alkaline-earth metals; radionuclides, such as those generated from actinides or lanthanides or other similar transition elements or from other elements, such as $^{47}$Sc, $^{67}$Cu, $^{67}$Ga, $^{82}$Rb, $^{89}$Sr, $^{88}$Y, $^{90}$Y, $^{99m}$Tc, $^{105}$Rh, $^{109}$Pd, $^{111}$In, $^{115m}$In, $^{125}$I, $^{131}$I, $^{140}$Ba, $^{140}$La, $^{149}$Pm, $^{153}$Sm, $^{159}$Gd, $^{166}$Ho, $^{175}$Yb, $^{177}$Lu, $^{186}$Re, $^{188}$Re, $^{194}$Ir, and $^{199}$Au, preferably $^{88}$Y, $^{90}$Y, $^{99m}$Tc, $^{125}$I, $^{131}$I, $^{153}$Sm, $^{166}$Ho, $^{177}$Lu, $^{186}$Re, $^{67}$Ga, $^{111}$In, and $^{140}$La; signal generators, which includes anything that results in a detectable and measurable perturbation of the system due to its presence, such as fluorescing entities, phosphorescence entities and radiation; signal reflectors, such as paramagnetic entities, for example, Fe, Gd, or Mn; chelated metal, such as any of the metals given above, whether or not they are radioactive, when associated with a chelant; signal absorbers, such as near infrared, contrast agents (such as imaging agents and MRI agents) and electron beam opacifiers, for example, Fe, Gd or Mn; antibodies, including monoclonal or polyclonal antibodies and anti-idiotype antibodies; antibody fragments; aptamers; hormones; biological response modifiers such as interleukins, interferons, viruses and viral fragments; diagnostic opacifiers; and fluorescent moieties. Carried pharmaceutical materials include scavenging agents such as chelants, antigens, antibodies, aptamers, or any moieties capable of selectively scavenging therapeutic or diagnostic agents.

In another embodiment, the carried materials, herein represented by [CM], are agricultural materials. Such materials which are suitable for use in these BNPC-[CM] conjugates include any materials for in vivo or in vitro treatment, diagnosis, or application to plants or non-mammals (including microorganisms) which can be associated with the Dendritic Polymer without appreciably disturbing the physical integrity of the BNPC. For example, the [CM] can be toxins, such as diphtheria toxin, gelonin, exotoxin A, abrin, modeccin, ricin, or toxic fragments thereof; metal ions, such as the alkali and alkaline earth metals; radionuclides, such as those generated from actinides or lanthanides or other similar transition elements or from other elements, such as $^{47}$Sc, $^{67}$Cu, $^{67}$Ga, $^{82}$Rb, $^{89}$Sr, $^{88}$Y, $^{90}$Y, $^{99m}$Tc, $^{105}$Rh, $^{109}$Pd, $^{111}$In, $^{115m}$In, $^{125}$I, $^{131}$I, $^{140}$Ba, $^{140}$La, $^{149}$Pm, $^{153}$Sm, $^{159}$Gd, $^{166}$Ho, $^{175}$Yb, $^{177}$Lu, $^{186}$Re, $^{188}$Re, $^{194}$Ir, and $^{199}$Au; signal generators, which includes anything that results in a detectable and measurable perturbation of the system due to its presence, such as fluorescing entities, phosphorescence entities and radiation; signal reflectors, such as paramagnetic entities, for example, Fe, Gd, or Mn; signal absorbers, such contrast agents and as electron beam opacifiers, for example, Fe, Gd, or Mn; hormones; biological response modifiers, such as interleukins, interferons, viruses and viral fragments; pesticides, including antimicrobials, algaecides, arithelmetics, acaricides, II insecticides, attractants, repellants, herbicides and/or fungicides, such as acephate, acifluorfen, alachlor, atrazine, benomyl, bentazon, captan, carbofuran, chloropicrin, chlorpyrifos, chlorsulfuron cyanazine, cyhexatin, cypermithrin, 2,4-dichlorophenoxyacetic acid, dalapon, dicamba, diclofop methyl, diflubenzuron, dinoseb, endothall, ferbam, fluazifop, glyphosate, haloxyfop, malathion, naptalam; pendimethalin, permethrin, picloram, propachlor, propanil, sethoxydin, temephos, terbufos, trifluralin, triforine, zineb, and the like. Carried agricultural materials include scavenging agents such as chelants, chelated metal (whether or not they are radioactive) or any moieties capable of selectively scavenging therapeutic or diagnostic agents.

In another embodiment, the carried material, herein represented by [CM], are immuno-potentiating agents. Such materials which are suitable for use in these BNPC-[CM] conjugates include any antigen, hapten, organic moiety or organic or inorganic compounds which will raise an immuno-response which can be associated with the Dendritic Polymers without appreciably disturbing the physical integrity of the BNPC. For example, the [CM] can be synthetic peptides used for production of vaccines against malaria (U.S. Pat. No. 4,735,799), cholera (U.S. Pat. No. 4,751,064) and urinary tract infections (U.S. Pat. No. 4,740,585), bacterial polysaccharides for producing antibacterial vaccines (U.S. Pat. No. 4,695,624) and viral proteins or viral particles for production of antiviral vaccines for the prevention of diseases such as AIDS and hepatitis.

The use of these BNPC-[CM] conjugates as carriers for immuno-potentiating agents avoids the disadvantages of ambiguity in capacity and structure associated with conventionally known classical polymer architecture or synthetic polymer conjugates used to give a macromolecular structure to the adjuvant carrier. Use of these BNPC-[CM] as carriers for immuno-potentiating agents, allows for control of the size, shape and surface composition of the conjugate. These options allow optimization of antigen presentation to an organism, thus resulting in antibodies having greater selectivity and higher affinity than the use of conventional adjuvants. It may also be desirable to connect multiple antigenic peptides or groups to the Dendritic Polymers, such as attachment of both T- and B-cell epitopes. Such a design would lead to improved vaccines.

It may also be desirable to conjugate pesticides or pollutants capable of eliciting an immune response, such as those containing carbamate, triazine or organophosphate constituents, to a dendrimer. Antibodies produced to the desired pesticide or pollutant can be purified by standard procedures, immobilized on a suitable support and be used for subsequent detection of the pesticide or pollutant in the environment or in an organism.

In a further embodiment, the carried materials, herein represented by [CM], which are suitable for use in these BNPC-[CM] conjugates include any materials other than agricultural or pharmaceutical materials which can be associated with these Dendritic Polymers without appreciably disturbing the physical integrity of the BNPC, for example: metal ions, such as the alkali and alkaline-earth metals; signal generators, which includes anything that results in a detectable and measurable perturbation of the system due to its presence, such as fluorescing entities, phosphorescence entities, infrared, near infrared, and radiation; signal reflectors, such as paramagnetic entities, for example, Fe, Gd, or Mn; signal absorbers, such as contrast agents and an electron beam opacifiers, for example, Fe, Gd, or Mn; pheromone moieties; fragrance moieties; dye moieties; and the like. [CM] include scavenging agents such as chelants or any moieties capable of selectively scavenging a variety of agents.

Preferably the carried materials [CM] are bioactive agents. As used herein, "bioactive" refers to an active entity such as a molecule, atom, ion and/or other entity which is capable of detecting, identifying, inhibiting, treating, catalyzing, controlling, killing, enhancing or modifying a targeted entity such as a protein, glycoprotein, lipoprotein, lipid, a targeted disease site or targeted cell, a targeted organ, a targeted organism [for example, a microorganism, plant or animal (including mammals such as humans)] or other targeted moiety. Also included as bioactive agents are genetic materials (of any kind, whether oligonucleotides, fragments, or synthetic sequences) that have broad applicability in the fields of gene therapy, siRNA, diagnostics, analysis, modification, activation, anti-sense, silencing, diagnosis of traits and sequences, and the like. These conjugates include effecting cell transfection and bioavailability of genetic material comprising a complex of a dendritic polymer and genetic material and making this complex available to the cells to be transfected.

These conjugates may be used in a variety of in vivo, ex vivo or in vitro diagnostic or therapeutic applications. Some examples are the treatment of diseases such as cancer, autoimmune disease, genetic defects, central nervous system disorders, infectious diseases and cardiac disorders, diagnostic uses such as radioimmunossays, electron microscopy, PCR, enzyme linked immunoadsorbent assays, nuclear magnetic resonance spectroscopy, contrast imaging, immunoscintography, and delivering pesticides, such as herbicides, fungicides, repellants, attractants, antimicrobials or other toxins. Non-genetic materials are also included such as interleukins, interferons, tumor necrosis factor, granulocyte colony stimulating factor, and other protein or fragments of any of these, antiviral agents.

These conjugates may be formulated into a tablet using binders known to those skilled in the art. Such dosage forms are described in *Remington's Pharmaceutical Sciences*, 18$^{th}$ ed. 1990, pub. Mack Publishing Company, Easton, Pa. Suitable tablets include compressed tablets, sugar-coated tablets, film-coated tablets, enteric-coated tablets, multiple compressed tablets, controlled-release tablets, and the like. Ampoules, ointments, gels, suspensions, emulsions, injections (intramuscular, intravenous, intraperitoneal) may also be used as a suitable formulation. Customary pharmaceutically-acceptable salts, adjuvants, diluents and excipients may be used in these formulations. For agricultural uses these conjugates may be formulated with the usual suitable vehicles and agriculturally acceptable carrier or diluent, such as emulsifiable concentrates, solutions, and suspensions.

Preparation of Solubility Enhancing Formulations Containing PEHAM Dendritic Polymers PEHAM Dendritic Polymers, as described in WO/2006/065266 PCT, as a part of BNPC, can be utilized as excipients for the enhancement of water solubility of poorly water soluble (hydrophobic) drugs or enhancement of oil solubility of poorly oil soluble (hydrophilic) drugs. Drugs can be associated with dendrimers by adsorption onto the surface or encapsulation into the dendrimer interior or a mixture of both. These interactions a driven by electrostatic attraction, hydrogen bonding between dendrimer and drug and hydrophobic or hydrophilic interactions or mixtures of these interactions, to name a few forces.

Drugs can be associated with dendrimers through chemical bounding to the surface [SF] or internal functionalities [IF] of PEHAM dendritic polymers in a [BNPC]-[CM] or both. This bonding can be done directly between PEHAM dendrimers and drug molecules or via a linker that can have a hydrolysable bond to the drug, i.e., acid or base or enzyme or temperature or light (e.g., IR light, which can penetrate tissue) labile. Drug bonding can cover all active functionalities available on PEHAM surface/interior or only a fraction of these functionalities.

Through appropriate chemical reaction it is possible to chemically bind a drug A only or mainly to the outside and a drug B only or mainly to the interior, this way creating a combination therapy or drug cocktail.

A chemical entity with strong interaction to the drug and [DP] can be associated with the dendrimer through physical means prior to drug adsorption or encapsulation or together with the drug. The entity will act as a co-excipient or co-encapsulant and enhance drug adsorption or encapsulation efficiency. A chemical entity with strong interaction to the drug and dendrimer can be chemically attached to [IF] prior to drug adsorption or encapsulation.

[BNPC]-PEHAM-[CM] formulations can be stored and provided as a powder mixture and re-dissolved prior to application. [BNPC]-PEHAM-[CM] formulations can be prepared as a solid mixture and pressed into tablets. [BNPC]-PEHAM-[CM] formulations can be prepared by concentration of mixed solutions and stored and provided as a suspension or paste filled into a capsule.

[BNPC]-PEHAM-[CM] formulations can be administered by an oral route, ampoule, intravenous injection, intramuscular injection, transdermal application, intranasal application, intraperitoneal administration, subcutaneous injection, ocular application, as wipes, sprays, gauze or other means for use at a surgical incision, near scar formation sites, or site of a tumor growth or removal or near or within a tumor.

[BNPC]-PEHAM-[CM] formulations can provide a more desirable pharmacological profile of the respective drug.

Typical Reaction Conditions

Methods of Making the Dendritic Polymers of Formula 2 are accomplished by known methods as described for Dendritic Polymers discussed above in the referenced patents and *Dendrimers and Other Dendritic Polymers*, eds. J. M. J. Fréchet, D. A. Tomalia, pub. John Wiley and Sons, 2001, which for the preparation of [DP] is hereby incorporated by reference. Of special interest are the [DP] for PEHAMs in US Published Appln. 2007-0298006, which hereby incorporated by reference for the teachings of making these PEHAM [DP].

N-SIS appears to affect the reactivity of a [TMC-C] with a [BR] or [EX] or [FF] of a dendron with a [RS] due to the relative sizes and the dimensions of the reactants concerned. If the [BR] is larger than the [TMC-C], then fewer [BR] can physically find space to allow chemical bonding and there results a large definable N-SIS effect. On the other hand, if the [TMC-C] is substantially larger than the [BR], then a smaller N-SIS effect results and more [BR] will be able to bond with the [TMC-C] due to enhanced space around the core, thus lessening SIS effects. To mitigate the effects of N-SIS, the present invention uses [EX]. Such [EX] allow more physical room between the [TMC-C] and the [BR] so the N-SIS effect is lessened.

Divergent dendritic growth can be precisely controlled to form ideal Dendritic Polymers which obey mathematical formulas, at least through the first several generations of growth. However, because the radii of dendrimer molecules increase in a linear manner as a function of generation during ideal divergent growth, whereas the surface cells amplify according to a geometric progression law, ideal dendritic growth does not extend indefinitely. There is a critical generation at which the reacting dendrimer surface does not have enough space to accommodate incorporation of all of the mathematically required new units. This stage in digression from ideal dendritic growth is referred to as the de Gennes dense-packed stage. At this stage, the surface becomes so crowded with surface functional groups [SF] that, although the surface groups are chemically reactive, they are sterically prohibited from participating further in ideal dendritic growth. In other words, the de Gennes dense-packed stage is reached in divergent dendrimer synthesis when the average free volume available to the reactive surface group decreases below the molecular volume required for the transition state of the desired reaction to extend the dendritic growth to the next generation. Nevertheless, the appearance of the de Gennes dense-packed stage in divergent synthesis does not preclude further dendritic growth beyond this point. It has been demonstrated by mass spectrographic studies that further increase in the molecular weight can occur beyond the de Gennes dense-packed stage. However, this occurs in a non-ideal fashion that no longer adheres to values predicted by dendritic mathematics.

Several major reaction types to make [DP] are known including: (1) nucleophilic addition reactions, (2) nucleophilic ring-opening reactions, (3) 1,3-cyclo-addition reaction types involving azides and acetylenes, and (4) free radical additions of thio to olefins. The addition reaction examples include but are not limited to Michael's addition reactions where acrylates are reacted with amines. The ring-opening reactions examples include but are not limited to ring-opening reactions where amines react with epoxy, thiorane, aziridine or oxazoline functional groups. In all of these cases the amines, acrylates, epoxies, thioranes, aziridines or oxazoline groups can be functional parts of the core [TMC-C], including simple core, multiple core, scaffolding core, or supercore, extender [EX], branch cell reagent [BR] or surface functional group [SF]. Reaction conditions for these two classes of reactions, addition reactions and ring-opening reactions, can be described by the range of conditions established in the literature for addition to a carbon-carbon double bond [See for example, R. T. Morrison, R. N. Boyd, *Organic Chemistry*, Chapter 6, pub. Allyn and Bacon, Inc, New York, N.Y., (1966) or general nucleophilic ring-opening reactions also at Chapter 6; and numerous other sources].

For the addition of a branch cell [BR], extender [EX], or functional group [RS] to a [TMC-C] or current generation product, the mole ratio of the molecule to be added to the moles of reactive functional groups on the [TMC-C] or current generation product is an important parameter. For example, in the addition of an extender group to a core, the mole ratio of [EX]/[TMC-C] is defined as the moles of extender molecules [EX] to the moles of reactive functional groups [RS] on the [TMC-C] or current generation structure (i.e. $N_o$). Similarly for addition of a branch cell [BR] to a [TMC-C] or current generation structure (BR)/[TMC-C] is defined as the moles of branch cell molecules [BR] to the moles of reactive functional groups [RS] on the [TMC-C] or current generation structure (i.e. $N_o$). Depending on the structure desired, the level of addition of branch cells or extenders to a [TMC-C] or current generational product can be controlled by the mole ratio added or by sterically induced stoichiometry (N-SIS). Preferred is using a excess of the molecules of the group being added, such as the extender or branch cell reagent to the functional groups on the [TMC-C] if full surface coverage is desired.

Order of addition can be addition of the [TMC-C] or current generation product to the branch cell or extender, or addition of the branch cell or extender to the [TMC-C] or current generation product. Preferred is addition of the [TMC-C] or current generation product to the extender or branch cell reagent.

Reaction times would vary depending on the reaction conditions, solvent, temperature, activity of the reagents and other factors, but can be generally classified by the breadth of reaction conditions sufficient to achieve nucleophilic ring-opening reactions of a strained epoxy, aziridine or other ring functional group. Reaction times can range from 1 minute to several days with longer reaction times needed for reaction of sterically bulky groups or reactions to crowded surfaces, such as addition of surface groups to higher generation [DP].

Reaction temperatures can be in the range typical for strained ring-opening addition reactions. The temperature range is limited by the thermal stability of the reagents in the reactions and the time of reaction.

Any organic solvents or water suitable for ring-opening addition reactions include typical solvents for nucleophilic ring-opening reactions. Any solvent mixture sufficient to dissolve the reagents to concentrations suitable to allow reaction can be used. Preferred solvents are polar, protic solvents. Also useful are mixtures of solvents containing both polar and nonpolar solvents, and protic and aprotic solvents or combinations thereof. Solvents can be a nonprotic solvent with sufficient catalytic quantities of protic solvent to allow reaction. The concentration of the reagents in the solvent can range significantly. In some cases the excess reagents for the reaction may be used as the solvent. Solvent mixtures can be predominantly nonprotic solvents with sufficient catalytic quantities of protic solvent to catalyze the reaction. This provides for conditions which allow the dissolution and reaction of less polar or non-polar [TMC-C], extenders [EX] or branch cell [BR] reagents. For example, difference in the reactivity of poly(glycidyl)ethers and poly(glycidyl)aniline with various nucleophilic branch cell reagents required investigation of various solvents and temperatures. For reactions which require higher temperatures, less volatile solvents may be required.

Catalysts can be added to facilitate the addition, 1,3-cyclo-addition or ring-opening reactions. Suitable catalysts include any commonly used catalysis for ring-opening reactions. Typical catalysts are Lewis acids and Lewis acid salts such as $LiBF_4$, $BF_3$, zinc salts or other catalysts in this category. Suitable catalysts for 1,3-cyclo-addition reactions also include copper and zinc salts.

Methods of isolation and purification of the products for both of these classes of reactions include typical methods of isolation for carbon-carbon double bond addition reactions and strain ring-opening addition reactions. Additionally, known methods of isolation of typical [DP] are used. Preferred are ultrafiltration, dialysis, column separations using silica gels or Sephadex™, precipitation, solvent separation or distillation. The method of isolation may vary with the size and generation of the product. As the polymer particle grows in size, more preferred methods of [DP] separation include ultrafiltration and dialysis. In some cases the differential solubility between the reacted and unreacted species can be used to assist in separation and isolation of the products. For example, the solubility differences between the epoxides, which are fairly non-polar, and the ring-opened polyols, which are more polar, can be utilized in the separation process.

Utility

These BNPC (i.e., bio-nano power cell aggregates) may be used as mentioned below and described further in this specification. It is believed that, based on knowledge of these BNPC may display all of these mentioned uses and many others. BNPC can be used for many applications in many markets, including:

Energy and electronics market:
  fuel cells (e.g., membranes, catalysts),
  energy storage (hydrogen, solid state lighting, thermal management for devices, light emitting diodes, displays, electronic inks, interlayer dielectric, photoresist, molecular electronics, telecom devices (waveguides), photonics, photographic materials, and stealth enhancement of materials),
  electrical devices, such as a pacemaker, a nerve growth stimulator,
  nerve stimulators for relief of chronic pain,
  stimulators for regrowth of bone or other tissue,
  drug-release valves or microvalves,
  fluid-flow control valve, such as a valve in a duct or in the urinary tract.
  electricity production from plants, trees, plant residues, or the like.
Environmental market:
  chemical sensors,
  biosensors,
  electronic nose (array-based sensors),
  lab-on-a-chip,
  nanoencoding of materials for environmental tracking and source identification,
  amplification technology for environmental sensors,
  biocidal materials,
  environmental sensing,
  remediation,
  clean water (e.g., ion exchange),
  clean air (e.g., super absorbers), and
  catalysts,
Personal/household market:
  environmental upgrading of fuels,
  coatings and surface modifiers (such as to provide scratch resistance, an antimicrobial surface, color changing, texture modifier, dirt resistant, water resistant),
  cleansers and lotions,
  cosmetics, pigments and dyes,
  UV absorbers,
  carriers of nutritionals,
  surfactants, and
  functional additives without adding color.
Chemicals and manufacturing market:
  improved binders,
  chemical catalysis,
  chemical separation materials,
  filtration systems,
  petrochemical processing (nanocatalysts), and
  toxic leak sensors.
Pharmaceutical and agricultural market:
  carried material present in their interior void spaces,
Human and animal medical and health markets:
  in-vivo diagnostic imaging (e.g., targeted control with increased contrast),
  diagnostic sensing (e.g., signal booster simultaneous targeting),
  drug delivery (e.g., enhanced oral, venous, dermal, nasal, etc.),
  drug discovery (e.g., miniaturization, bioarrays),
  in-vitro and ex-vivo diagnostics and therapies,
  protein resistant coatings for medical devices (e.g., in-vivo and ex-vivo),
  anti-biofouling coatings and surface for devices,
  transdermal delivery,
  chemotherapies for oncology,
  remote and in-vivo devices,
  polyvalent pharmaceutical applications,
  near infrared absorbers,
  non-invasive imaging and sensing,
  targeted therapies,
  magnetic bioreactors (e.g., cell growth and harvesting),
  drug releasing stents,
  surface coatings, and
  controlled release (e.g., therapeutics, nutritionals, etc.).
Food and agriculture market:
  highly selective control sensors, sensory amplification materials (e.g., taste, smell, sound, sight, and feel),
  targeted, non-toxic biodegradable pesticides, herbicides, time-released fertilizers and pesticides,
  packaging materials (e.g., microbe resistant plastics), freshness, contamination, and/or tamper sensors, and delivery of drugs to plants and animals.

BNPC-[CM] conjugates can be used for many applications in many carried materials markets, including:
  pharmaceuticals, such as antibiotics, analgesics, hypertensives, cardiotonics, steroids and the like, such as acetaminophen, acyclovir, alkeran, amikacin, ampicillin, aspirin, bisantrene, bleomycin, neocardiostatin, chloroambucil, chloramphenicol, cytarabine, daunomycin, doxorubicin, cisplatin, carboplatin, fluorouracil, taxol, gemcitabine, gentamycin, ibuprofen, kanamycin, meprobamate, methotrexate, novantrone, nystatin, oncovin, phenobarbital, polymyxin, probucol, procarbabizine, rifampin, streptomycin, spectinomycin, symmetrel, thioguanine, tobramycin, trimethoprim, and valbanl;
- toxins, such as diphtheria toxin, gelonin, exotoxin A, abrin, modeccin, ricin, or toxic fragments thereof;
- metal ions, such as the alkali and alkaline-earth metals; radionuclides, such as those generated from actinides or lanthanides or other similar transition elements or from other elements, such as $^{47}$Sc, $^{67}$Cu, $^{67}$Ga, $^{82}$Rb, $^{89}$Sr, $^{88}$Y, $^{90}$Y, $^{99m}$Tc, $^{105}$Rh, $^{109}$Pd, $^{111}$In, $^{115m}$In, $^{125}$I, $^{131}$, $^{140}$Ba, $^{140}$La, $^{149}$Pm, $^{153}$Sm, $^{159}$Gd, $^{166}$Ho, $^{175}$Yb, $^{177}$Lu, $^{186}$Re, $^{185}$Re, $^{194}$Ir, and $^{199}$Au, preferably $^{88}$Y, $^{153}$Sm, $^{177}$Lu, $^{186}$Re, $^{67}$Ga, $^{111}$In, $^{115m}$In, $^{140}$La;
- signal generators, which includes anything that results in a detectable and measurable perturbation of the system due to its presence, such as fluorescing entities, phosphorescence entities and radiation;
- signal reflectors, such as paramagnetic entities, for example, Fe, Gd, or Mn; chelated metal, such as any of the metals given above, whether or not they are radioactive, when associated with a chelant;
- signal absorbers, such as near infrared, contrast agents (such as imaging agents and MRI agents) and electron beam opacifiers, for example, Fe, Gd or Mn;
- antibodies, including monoclonal or polyclonal antibodies and anti-idiotype antibodies; antibody fragments; aptamers; hormones; biological response modifiers such as interleukins, interferons, viruses and viral fragments; diagnostic opacifiers; and fluorescent moieties.
- Carried pharmaceutical materials include scavenging agents such as chelants, antigens, antibodies, aptamers, or any moieties capable of selectively scavenging therapeutic or diagnostic agents.
- agricultural materials, in vivo or in vitro treatment, diagnosis, or application to plants or non-mammals (including microorganisms) such as toxins, such as diphtheria toxin, gelonin, exotoxin A, abrin, modeccin, ricin, or toxic fragments thereof;
- metal ions, the alkali and alkaline earth metals
- radionuclides, such as those generated from actinides or lanthanides or other similar transition elements or from other elements, such as toxins, such as diphtheria toxin, gelonin, exotoxin A, such as $^{47}Sc$, $^{67}Cu$, $^{67}Ga$, $^{82}Rb$, $^{89}Sr$, $^{88}Y$, $^{99}Y$, $^{99m}Tc$, $^{195}Rh$, $^{109}Pd$, $^{111}In$, $^{115m}In$, $^{121}I$, $^{131}I$, $^{140}Ba$, $^{140}La$, $^{149}Pm$, $^{153}Sm$, $^{159}Gd$, $^{166}Ho$, $^{175}Yb$, $^{177}Lu$, $^{186}Re$, $^{185}Re$, $^{194}Ir$, and $^{199}Au$;

signal generators, which includes anything that results in a detectable and measurable perturbation of the system due to its presence, such as fluorescing entities, phosphorescence entities and radiation;

signal reflectors, such as paramagnetic entities, for example, Fe, Gd, or Mn; signal absorbers, such contrast agents and as electron beam opacifiers, for example, Fe, Gd, or Mn; hormones; biological response modifiers, such as interleukins, interferons, viruses and viral fragments;

pesticides, including antimicrobials, algaecides, arithelmetics, acaricides, II insecticides, attractants, repellants, herbicides and/or fungicides, such as acephate, acifluorfen, alachlor, atrazine, benomyl, bentazon, captan, carbofuran, chloropicrin, chlorpyrifos, chlorsulfuron cyanazine, cyhexatin, cypermithrin, 2,4-dichlorophenoxyacetic acid, dalapon, dicamba, diclofop methyl, diflubenzuron, dinoseb, endothall, ferbam, fluazifop, glyphosate, haloxyfop, malathion, naptalam; pendimethalin, permethrin, picloram, propachlor, propanil, sethoxydin, temephos, terbufos, trifluralin, triforine, zineb, and the like.

Carried agricultural materials include scavenging agents such as chelants, chelated metal (whether or not they are radioactive) or any moieties capable of selectively scavenging therapeutic or diagnostic agents.

immuno-potentiating agents, including any antigen, hapten, organic moiety or organic or inorganic compounds which will raise an immuno-response. For example, the carried materials can be synthetic peptides used for production of vaccines against malaria (U.S. Pat. No. 4,735, 799), cholera (U.S. Pat. No. 4,751,064) and urinary tract infections (U.S. Pat. No. 4,740,585), bacterial polysaccharides for producing antibacterial vaccines (U.S. Pat. No. 4,695,624) and viral proteins or viral particles for production of antiviral vaccines for the prevention of diseases such as AIDS and hepatitis.

pesticides or pollutants capable of eliciting an immune response, such as those containing carbamate, triazine or organophosphate constituents any materials other than agricultural or pharmaceutical materials which can be associated with a BNPC without appreciably disturbing the physical integrity of the BNPC, for example: metal ions, such as the alkali and alkaline-earth metals; signal generators, which includes anything that results in a detectable and measurable perturbation of the system due to its presence, such as fluorescing entities, phosphorescence entities, infrared, near infrared, and radiation; signal reflectors, such as paramagnetic entities, for example, Fe, Gd, or Mn; signal absorbers, such as contrast agents and an electron beam opacifiers, for example, Fe, Gd, or Mn; pheromone moieties;

fragrance moieties;

dye moieties; and the like.

Carried materials include scavenging agents such as chelants or any moieties capable of selectively scavenging a variety of agents.

bioactive agents, such as a molecule, atom, ion and/or other entity which is capable of detecting, identifying, inhibiting, treating, catalyzing, controlling, killing, enhancing or modifying a targeted entity such as a protein, glycoprotein, lipoprotein, lipid, a targeted disease site or targeted cell, a targeted organ, a targeted organism [for example, a microorganism, plant or animal (including mammals such as humans)] or other targeted moiety. Also included as bioactive agents are genetic materials (of any kind, whether oligonucleotides, fragments, or synthetic sequences) that have broad applicability in the fields of gene therapy, siRNA, diagnostics, analysis, modification, activation, anti-sense, silencing, diagnosis of traits and sequences, and the like. These conjugates include effecting cell transfection and bioavailability of genetic material comprising a complex of a BNPC and genetic material and making this complex available to the cells to be transfected.

in vivo, ex vivo or in vitro diagnostic or therapeutic applications, such as cancer, autoimmune disease, genetic defects, central nervous system disorders, infectious diseases and cardiac disorders, diagnostic uses such as radioimmunoassays, electron microscopy, PCR, enzyme linked immunoadsorbent assays, nuclear magnetic resonance spectroscopy, contrast imaging, immunoscintography, and delivering pesticides, such as herbicides, fungicides, repellants, attractants, antimicrobials or other toxins. Non-genetic materials are also included such as interleukins, interferons, tumor necrosis factor, granulocyte colony stimulating factor, and other protein or fragments of any of these, antiviral agents.

While not wishing to be bound by theory, it is believed that the advantageous results of the present invention are obtained because of the combination of the components of Formula 2.

The present invention will be further clarified by a consideration of the following examples, which are intended to be purely exemplary of the present invention and serve to illustrate the preparation of compounds of Formula 2.

Examples

While not wishing to be bound by theory, it is believed that the advantageous results of the present invention are obtained because of the combination of the components of Formula 2.

Examples

In the following examples, the various reactions conditions are believed true and exemplify the preparation of BNPC of Formula 2. Enzymes pictured in the examples illustrate that enzymes and other materials can associate with BNPCs to make useful products. The lettered examples are the preparation of starting materials and the numbered examples are of BNCP moieties of Formula 2.

STARTING MATERIAL EXAMPLES

Example A

Synthesis of pentaerythritol tetraglycidyl ether (PETGE)

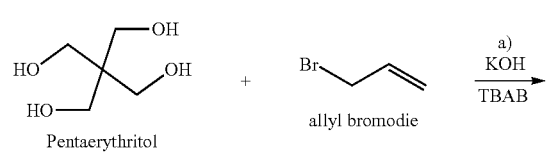

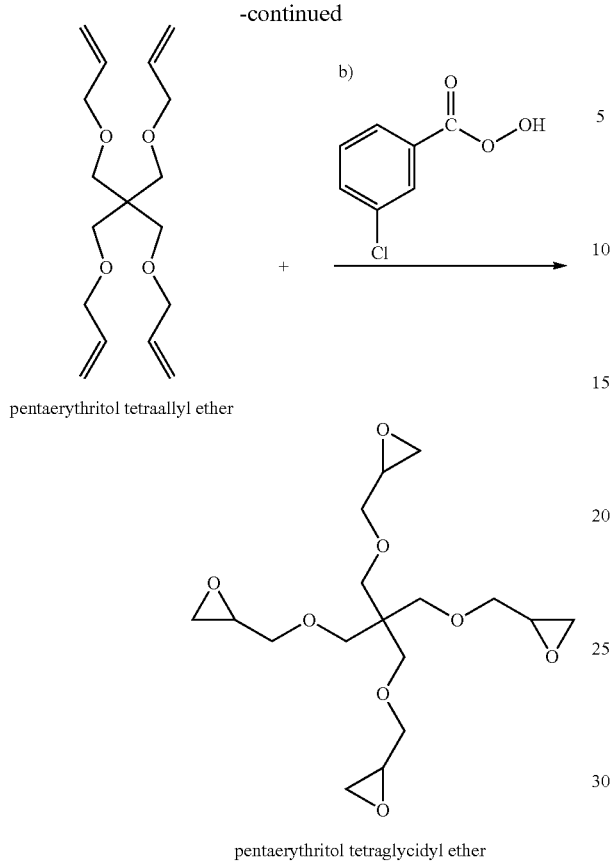

pentaerythritol tetraallyl ether pentaerythritol tetraglycidyl ether

According to the procedure described in US Published Patent Application 20070298006:

a) Pentaerythritol (15.03 g, 110 mmol) (Sigma-Aldrich) and 250 mL of THF were mixed in a 1-L 3-neck round bottom flask with condensor. KOH (85.93 g 1.35 mol 3.0 equiv. per OH), and tetrabutyl ammonium bromide (TBAB) (0.460 g, 1.23 mol) (Sigma-Aldrich) were added via powder funnel, followed by addition of allyl bromide, (106.6 g, 1.35 mol, 3.0 equiv. per OH) via a 250-mL addition funnel over 10 mins. The reaction was then immediately placed into an oil bath at 70° C. for 24 hours. The reaction was monitored by TLC (110:1 hexanes:ethyl acetate), showing the product spot at $R_f$=0.4 and no spots for tri-, di-, or mono-allylsubstituted pentaerythritol. The reaction mixture was vacuum-filtered through a 150-mL coarse glass-fritted Büchner funnel. The organic layer was diluted with diethyl ether (2×150 mL). The organic layer was washed with 5% $K_2CO_3$ (5×300 mL) and dried over $MgSO_4$. Volatiles were removed by a rotary evaporator (40° C. bath temperature) to yield the pentaerythritol tetraallyl ether, (28.88 g; 88% yield); and has the following spectra:

IR (Neat): $v_{max}$ 3080, 2867, 1646, 1478, 1422, 1350, 1264, 1137, 992, 922 cm$^{-1}$, and $^{13}$C NMR: (75 MHz, CDCl$_3$): δ 45.33, 69.25, 72.15, 115.95, 135.16; and $^1$H NMR: (300 MHz, CDCl$_3$): δ 3.39 (4H, s), 3.84 (4H, q, J=2.3 Hz), 5.04 (2H, q, J=13.8 Hz), 5.80 (1H, septuplet, J=7.78 Hz).

ESI: $C_{17}H_{24}O_4$ Calc. 296. found Mol Wt. 296.

b) PETAE (9.87 g, 33.0 mmol) and 150 mL of chloroform were added to a 1-L 3-neck flask equipped with mechanical stirring. Then m-CPBA (70%) (37.53 g, 153 mmol, 1.14 equiv. per alkene) (Sigma-Aldrich) was added over 10 minutes via an addition funnel. The reaction flask became warm within 30 mins. of the peracid addition. The reaction was stirred for 72 hours at 22° C., then diluted with 300 mL DCM and transferred to a 1-L separatory funnel. The organic layer was washed with 3% $Na_2S_2O_5$ (3×300 mL) and 3% $NaHCO_3$ (3×300 mL). The organic layer was dried with $Na_2SO_4$, filtered and volatile materials were removed by a rotary evaporator (40° C. bath temperature). TLC (7:3 toluene:acetone) on silica showed one spot at $R_f$=0.48. Further drying of the product overnight at high vacuum yielded PETGE as a clear colorless viscous liquid (7.66 g; 91% yield); and has the following spectra:

IR (Neat): $V_{max}$ 3055, 2876, 1724, 1480, 1340, 1258, 1163, 1018, 908, 845, 799, 760 cm$^{-1}$; and 13NMR (75 MHz, CDCl$_3$): δ 43.96, 45.54 50.62, 69.80, 71.90; and $^1$H NMR: (300 MHz, CDCl$_3$): δ 2.55 (1H, q, J=2.05 Hz), 2.72 (1H, t, J=2.33 Hz), 3.09 (1H, q, J=3.06 Hz) 3.32 (1H, q, J=4.43 Hz), 3.45 (2H, d, J=1.65 Hz), 3.64 (1H, q, J=3.675 Hz); and ESI: $C_{17}H_{28}O_8$ Calc. 360. found Mol Wt. 360.

Example B

Synthesis of Trimethylolpropane triglycidyl ether (TMPTGE)

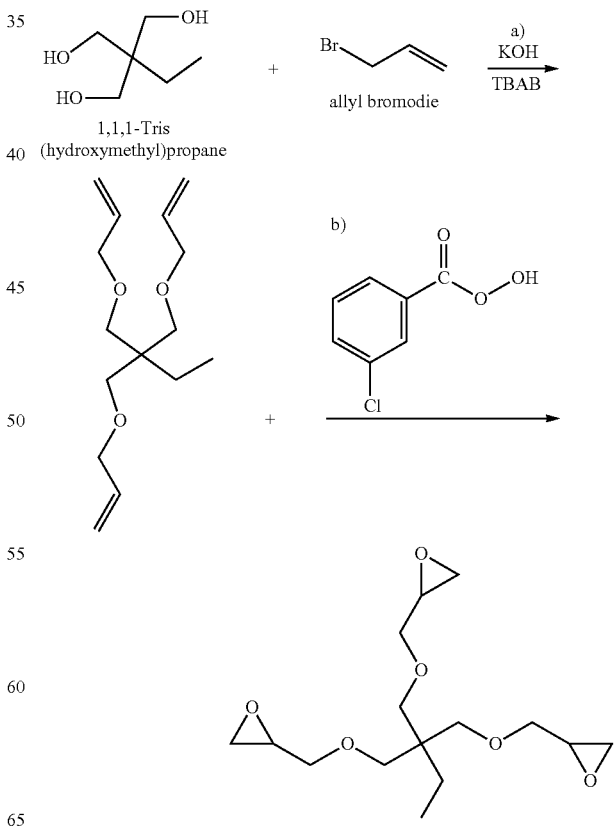

According to the following procedure:

1,1,1-Tris(hydroxymethyl)propane (trimethylolpropane) (13.20 g, 110 mmol) (Sigma-Aldrich) and 250 mL of THF were mixed in a 500-mL 3-neck round bottom flask with condensor. KOH (64.5 g 1.01 mol 3.0 equiv. per OH), and tetrabutyl ammonium bromide (TBAB) (0.345 g, 0.923 mol) (Sigma-Aldrich) were added via powder funnel, followed by addition of allyl bromide, (80.0 g, 0.923 mol, 3.0 equiv. per OH) via a 125-mL addition funnel over 10 mins. The reaction was then immediately placed into an oil bath at 70° C. for 24 hours. The reaction was monitored by TLC (110:1 hexanes:ethyl acetate), showing the product spot at $R_f$=0.4 and no spots for tri-, di-, or mono-allylsubstituted 1,1,1-Tris(hydroxymethyl)propane. The reaction mixture was vacuum-filtered through a 150-mL coarse glass-fritted Büchner funnel. The organic layer was diluted with diethyl ether (2×250 mL). The organic layer was washed with 5% $K_2CO_3$ (5×300 mL) and dried over $MgSO_4$. Volatiles were removed by a rotary evaporator (40° C. bath temperature) to yield the trimethylolpropane allyl ether (TMPTAE), (11.95 g; 90% yield); and has the following spectra:

ESI: $C_{15}H_{26}O_3$ Calc. 254. found Mol Wt. 254 a) A 250-mL round bottom flask was charged with TMPTAE (3.84 g, 15.0 mmol and 75 mL chloroform (Sigma-Aldrich). To this solution was added under mechanical stirring m-CPBA (13.26 g, 54.0 mmol) (Sigma-Aldrich) in portions at RT. The mixture was stirred for 3 days, then first washed with 3% aqueous sodium metabisulfite ($Na_2S_2O_5$) solution (3×150 mL) (Sigma-Aldrich), followed by 3% aqueous sodium hydrogen carbonate ($NaHCO_3$) solution (3×150 mL). The organic layer was dried over sodium sulfate, concentrated by rotary evaporation to give pale yellow colored liquid, trimethylolpropane glycidyl ether (TMPTGE) (4.11 g, 89.8% yield). Its spectra are as follows:

ESI: $C_{15}H_{26}O_6$ Calc. 302. found Mol Wt. 302

Example C

Polyvinylimidazole

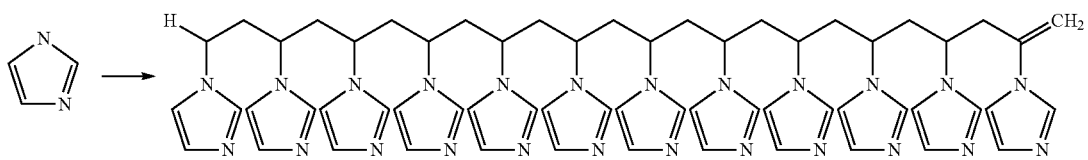 [SMILES: c1c[nH]cn1 ; C=C(CC(CC(CC(CC(CC(CC(CC(CC(CC(CC(CCn1ccnc1)n1ccnc1)n1ccnc1)n1ccnc1)n1ccnc1)n1ccnc1)n1ccnc1)n1ccnc1)n1ccnc1)n1ccnc1)n1ccnc1)n1ccnc1]

PVI was prepared by the method of Chapiro, et al., Eur. Polym. J., 24: 1019-1028 (1988), using AIBN as initiator. Vinylimidazole (15 mL, 166 mmol) was added to a 250 mL round-bottomed flask, which contained 150 mL of toluene. After it was degassed by nitrogen gas for 5 minutes, AIBN (Azobisisobutyronitrile) (150 mg, 0.913 mmol) was added, and then degassed for another 1 minute. The reaction was heated for two hours by an external oil bath which temperature was set up at 120° C. When reaction finished, the precipitated white polymer was collected by vacuum filtration and dried under reduced pressure. (PVI: 10.53 g, yield: 67.5%) and its spectra are:

$^1$H NMR (300 MHz, $D_2O$): δ: 1.98 (2H, b), 4.82 (0.5H, d), 5.28 (0.5H, d), 6.92 (1H, s), 7.22 (1H, s), 7.70 (1H, s).

$^{13}$C NMR (75 MHz, $D_2O$): δ: 136.98, 129.14, 117.15, 52.41, 40.66.

Example D 4,4'-dipiperazine-2,2'-bipyridine

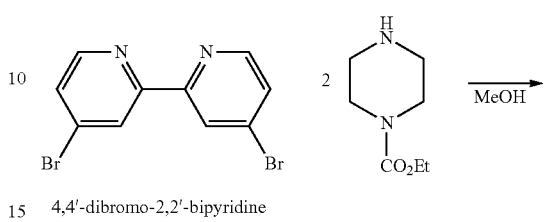

4,4'-dibromo-2,2'-bipyridine

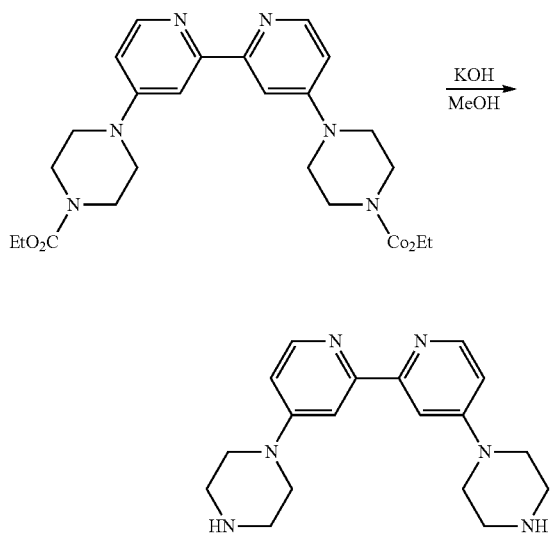

a) To a mixture of 4,4'-dibromo-2,2'-bipyridine (0.5 g) (1.6 mmol) (Carbosynth) and triethylamine (0.5 g) (5.0 mmol) in 40 mL methanol in a 100 mL round bottom flask, ethyl 1-piperazinecarboxylate (0.63 g) (4 mmol) was added and heated under $N_2$ at 140° C. in an oil bath for 4-5 h. Excess tris(2-aminoethyl)-amine was removed by high vacuum distillation at 90-120° C.

b) A 10 mL of potassium hydroxide solution (0.57 g of KOH dissolved in 10 mL $H_2O$) and 10 mL of methanol were added to flask, and then refluxed for 24 hours. The pH of reaction crude was adjusted to 8 by HCl, and then dried by rotary evaporator. A 15 mL of methanol was added to dissolve product, and insoluble materials were removed by filtration. The product was purified by a silica gel column, eluting with 5% $NH_4OH$ in isopropyl alcohol. Yield: 65% and its spectra are:

ESI: $C_{18}H_{24}N_6$ Calc. 324. found Mol Wt. 324

Example E

2,2'-bipyridine-4,4'-dicarboxylic acid chloride

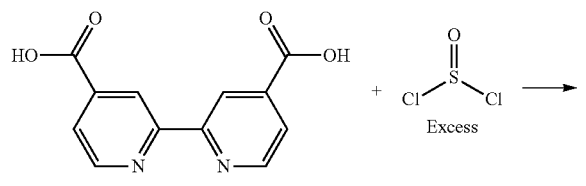

4,4'-Dicarboxy-2,2'-bipyridine 2,2'-bipyridine-4,4'-dicarbonyl dichloride 4,4'-dicarboxy-2,2'-bipyridine (0.25 g, 1.02 mmol) (Carbosynth) was added a 50 mL round-bottomed flask, followed by 20 mL (excess) thionyl chloride, and then the reaction was refluxed for 24 h. 2,2'-bipyridine-4,4'-dicarboxylic acid chloride was yielded after the crude was rotovated to remove solvent. It was dissolved in a 10 mL of methylene chloride to make up 2,2'-bipyridine-4,4'-dicarboxylic acid chloride/methylene chloride solution for next step reaction. It was not analyzed before use due its high reactivity.

Example F

4,4'-dicarboxypiperazine-2,2'-bipyridine

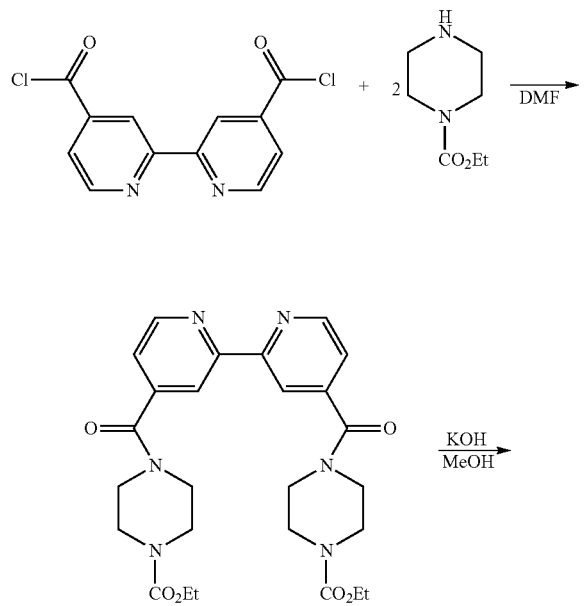

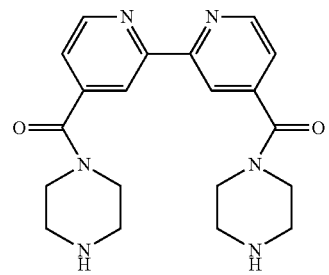

a) Ethyl piperazine-1-carboxylate (0.49 g, 3.08 mmol) and triethylamine (0.414 g, 4.1 mmol) were added to a 50 mL round-bottomed flask, followed by 15 mL methylene chloride. It was cooled to −20° C. in dry ice/acetone, and 2,2'-bipyridine-4,4'-dicarboxylic acid chloride/methylene chloride solution was dripped in it. It was allowed to warm to room temperature slowly and then refluxed for 1 hour to finish the reaction.

b) A 10 mL of potassium hydroxide solution (0.57 g of KOH dissolved in 10 mL $H_2O$) and 10 mL of methanol were added to flask, and then refluxed for 24 hours. The pH of reaction crude was adjusted to 8 by HCl, and then dried by rotary evaporator. A 15 mL of methanol was added to dissolve product, and insoluble materials were removed by filtration. The crude was washed by water (5*20 mL), dried over $Na_2SO_4$ and then dripped into diethyl ether (400 mL) to crystallize product, the 2,2'-bipyridine-4,4'-diylbis(piperazin-1-ylmethanone (0.40 g, yield: 74%) and its spectra are:

ESI: $C_{20}H_{24}N_6O_2$ Calc. 380. found Mol Wt. 380.

Example G

Methylisopropyliminoethylpiperazine (MIPIEP) and methyl isobutyl Protected 1-(2-aminoethyl)piperazine (PEA) [Linkers]

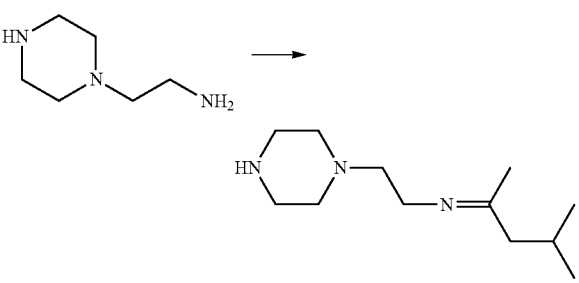

In a round bottom flask equipped with a Dean-Stark trap and condenser, a mixture of AEP (0.0625 mol) in 4-methyl-2-pentanone is heated to reflux under an argon atmosphere. The theoretical amount of water is distilled out as an azeotrope and the reaction is cooled to RT. The reaction mixture is placed into a 25-mL round bottom flask and PETGE in MeOH is added. The mixture is heated to 60° C. overnight, then the solvent is removed under vacuum. The residue is treated with 2-propanol and water. The mixture is heated to 50° C. for 2.5 h, then the solvent is removed to give the product methylisopropyliminoethylpiperazine (MIPIEP).

Example H

Methyl isobutyl Protected diethylenetriamine (DETA) [Linkers]

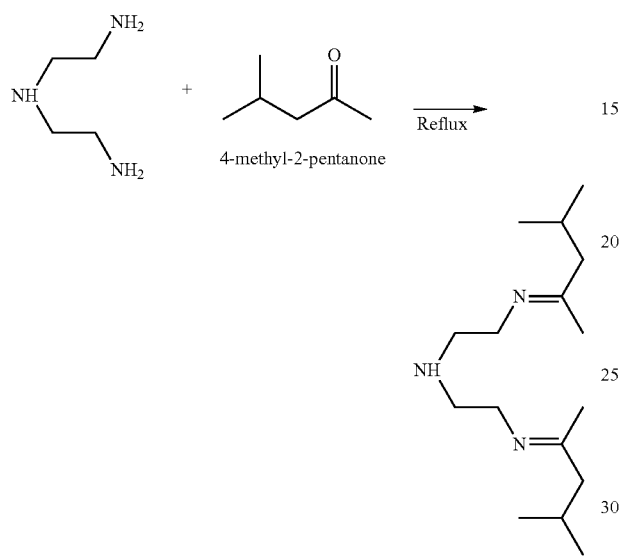

4-methyl-2-pentanone

In a 250-mL round bottom flask, equipped with a Dean-Stark trap, DETA (63.6 mmol) and 4-methyl-2-pentanone are heated to 140° C. under argon atmosphere. The theoretical amount of water is distilled out as an azeotrope, the reaction is cooled to RT. The mixture is transferred to a round bottom flask and the solvent is removed by rotary evaporation, yielding methyl isobutyl protected diethylenetriamine (DETA).

Transition Metal Complexes [TMC]

Example 1

Osmium bis(BiPy)(di-amino)dichloro

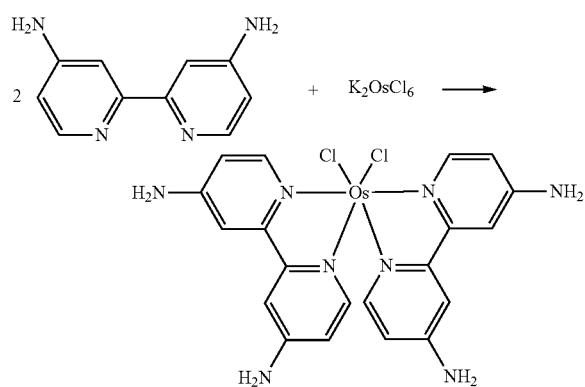

4,4'-diamino-2,2'-bipyridine [BiPy(di-amino)] (0.81 g, 4.36 mmol) (Carbosynth) was dissolved in 7 mL ethylene glycol and 25 mL DMF, followed by $K_2OsCl_6$ (1.0 g, 2.08 mmol). The reaction mixture was refluxed for 1 hour. It was then cooled to RT and transferred to a 500 mL beaker. $Na_2S_2O_4$ solution (7.2 g $Na_2SO_4$ in 150 mL water) was dripped to reaction mixture over a period of a half hour. The reaction mixture in the beaker was cooled in an ice bath for 1.5 hours. The solid product was collected by vacuum filtration and washed with deionized water (3×20 mL), refrigerated methanol (10 mL), and diethyl ether (120 mL) respectively. It was dried in a vacuum oven at 60° C. for 24 hours. (product: 1.22 g, yield: 68%) and its spectra are as follows:

IR (Neat): $V_{max}$ 3336, 3218, 1623, 1556, 1505, 1474, 1265, 1027 $cm^{-1}$;

ESI: $C_{20}H_{20}Cl_2N_8Os$ Calc. 634. found Mol Wt. 634.

Example 2

Osmium tris(4,4'-diamino-2,2'-bipyridine)dichlorate

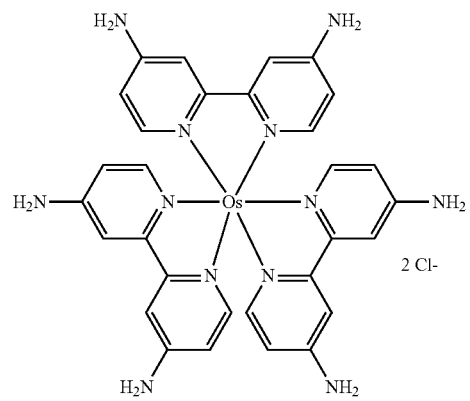

4,4'-diamino-2,2'-bipyridine [BiPy(di-amino)] (1.86 g, 9.98 mmol) (Carbosynth) was dissolved in 35 mL of ethylene glycol, followed by $K_2OsCl_6$ (0.8 g, 1.66 mmol). The reaction mixture was refluxed for 120 hours at 190-200° C. It was then cooled to RT and transferred to a 500 mL beaker. $Na_2S_2O_4$ solution (7.2 g $Na_2SO_4$ in 150 mL water) was dripped to reaction mixture over a period of a half hour. The reaction mixture in the beaker was cooled in an ice bath for 1.5 hours. The solid product was collected by vacuum filtration and washed with deionized water (3×20 mL), refrigerated methanol (10 mL), and diethyl ether (120 mL) respectively. The black powder, osmium tris(4,4'-diamino-2,2'-bipyridine) dichlorate, was collected and dried in a vacuum oven at 60° C. for 24 hours. (product: 1.08 g, yield: 76%) and its spectra are:

ESI: $C_{30}H_{30}N_{12}Os$ Calc. 750. found Mol Wt. 750

Example 3

Osmium bis(4,4'-di-carboxy-piperazine-2,2'-bipyridine)dichloro

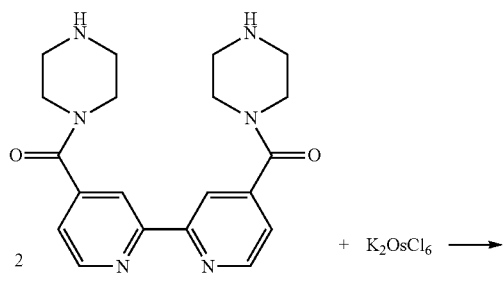

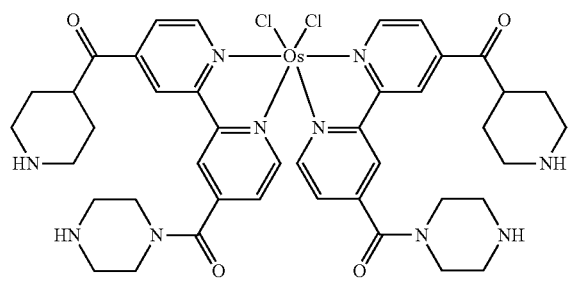

K$_2$OsCl$_6$ (0.145 g, 0.3 mmol) and BiPy(di-carboxy-piperazine) (0.24 g, 0.63 mmol) (from Example F) is added to a 50 round-bottomed flask, followed by 20 mL of DMF and 7 mL of ethylene glycol. The reaction is refluxed for 1.5 hours. After reaction finished, it is cooled down to RT and dripped to 500 mL of diethyl ether to crystallize product.

Example 4

Osmium tris(4,4'-di-carboxy-piperazine-2,2'-bipyridine)

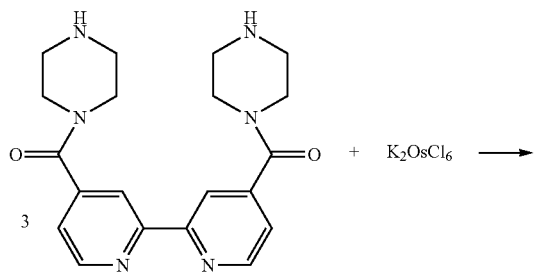

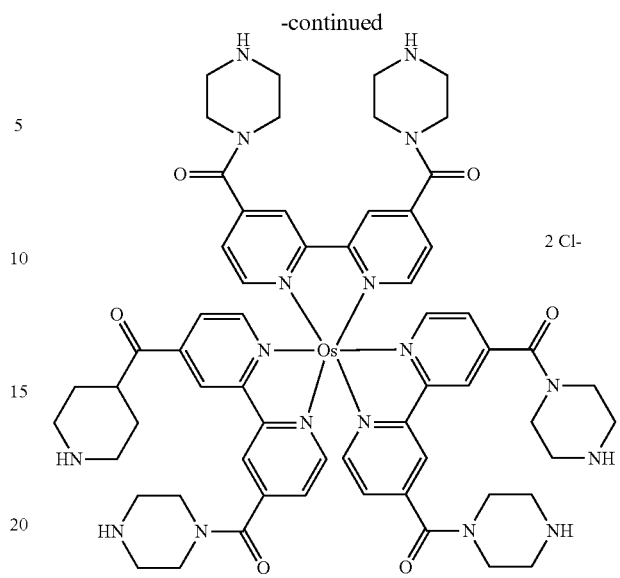

K$_2$OsCl$_6$ (0.09 g, 0.20 mmol) and BiPy(di-carboxy-piperazine) (0.32 g, 0.84 mmol) (from Example F) is added to a 50 round-bottomed flask, followed by 20 mL of DMF and 7 mL of ethylene glycol. The reaction is refluxed for 1.5 hours. After reaction finished, it is cooled down to RT and dripped to 500 mL of diethyl ether to crystallize product.

Example 5

Ruthenium bis(4,4'-diamino-2,2'-bipyridine)dichloro

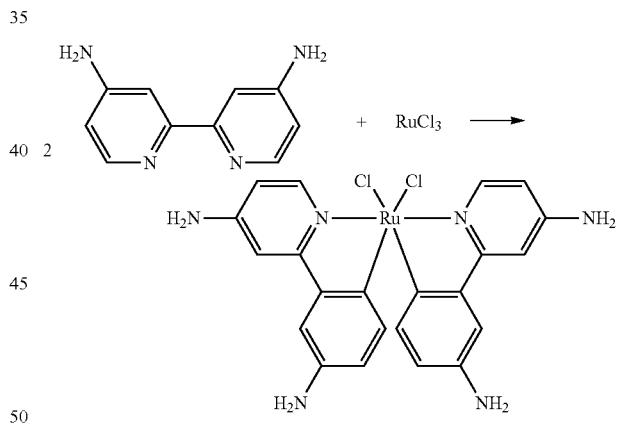

4,4'-diamino-2,2'-bipyridine [BiPy(di-amino)] (2.02 g, 10.86 mmol) (Carbosynth) was dissolved in 7 mL ethylene glycol and 25 mL DMF, followed by RuCl$_3$.3H$_2$O (1.31 g, 5.0 mmol). The reaction mixture was refluxed for 10 hour. It was then cooled to RT and transferred to a 500 mL beaker. Na$_2$S$_2$O$_4$ solution (7.2 g Na$_2$SO$_4$ in 150 mL water) was dripped to reaction mixture over a period of a half hour. The reaction mixture in the beaker was cooled in an ice bath for 1.5 hours. The solid product was collected by vacuum filtration and washed with deionized water (3×20 mL), refrigerated methanol (10 mL), and diethyl ether (120 mL) respectively. The black powder, ruthenium bis(4,4'-diamino-2,2'-bipyridine)dichloro, was collected and dried in a vacuum oven at 60° C. for 24 hours. (product: 2.38 g, yield: 75%) and its spectra are:

ESI: C$_{20}$H$_{20}$Cl$_2$N$_8$Ru Calc. 544. found Mol Wt. 544.

Example 6

Ruthenium tris(4,4'-diamino-2,2'-bipyridine)

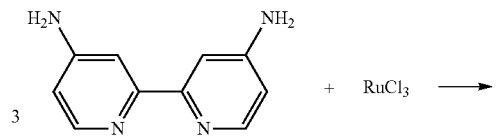

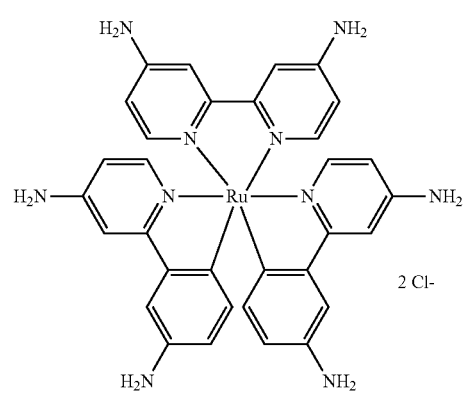

4,4'-diamino-2,2'-bipyridine [BiPy(di-amino)] (5.21 g, 28.02 mmol) (Carbosynth) was dissolved in 35 mL of ethylene glycol, followed by RuCl$_3$.3H2O (1.22 g, 4.67 mmol). The reaction mixture was refluxed for 80 hours at 190-200° C. It was then cooled to RT and transferred to a 500 mL beaker. Na$_2$S$_2$O$_4$ solution (7.2 g Na$_2$S$_2$O$_4$ in 150 mL water) was dripped to reaction mixture over a period of a half hour. The reaction mixture in the beaker was cooled in an ice bath for 1.5 hours. The solid product was collected by vacuum filtration and washed with deionized water (3×20 mL), refrigerated methanol (10 mL), and diethyl ether (120 mL) respectively. The black powder, ruthenium tris(4,4'-diamino-2,2'-bipyridine), was collected and dried in a vacuum oven at 60° C. for 24 hours. (product: 2.79, yield: 73%) and its spectra are:

ESI: C$_{30}$H$_{30}$N$_{12}$Ru Calc. 660. found Mol Wt. 660.

Example 7

Iron bis(BiPy)(di-amino)perchlorate

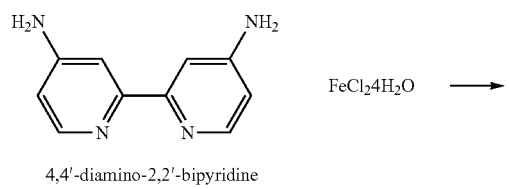

4,4'-diamino-2,2'-bipyridine

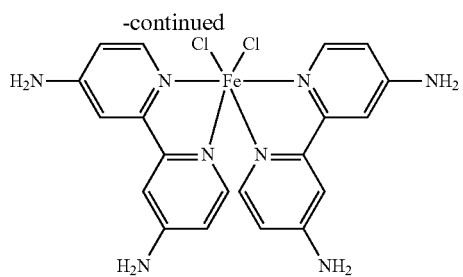

In DMF, FeClO$_4$ (0.21 mmol) is added to 4,4'-diamino-2,2'-bipyridine [BiPy (di-amino)] (0.42 mmol) (Carbosynth). The mixture is refluxed for at least 4 h under a nitrogen atmosphere at atmospheric pressure and at a temperature between 150° and 155° C. The solution is cooled to RT and solvent is removed by rotary evaporation. Cold water is added and the complex iron bis(BiPy)(diamino)perchlorate is isolated by filtration.

Example 8

Iron tris(BiPy)(di-amino)perchlorate

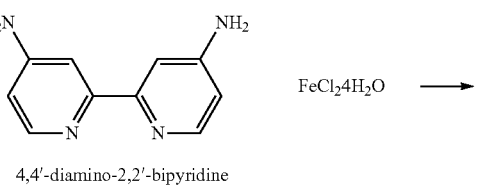

4,4'-diamino-2,2'-bipyridine

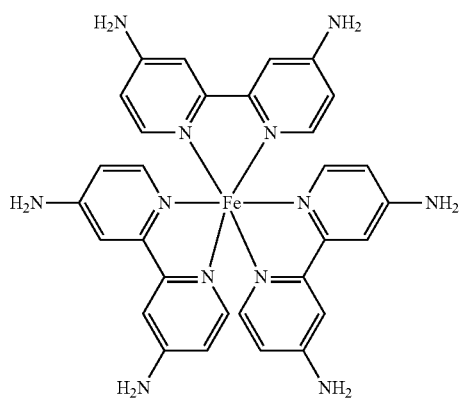

In DMF, FeClO$_4$ (0.21 mmol) is added to 4,4'-diamino-2,2'-bipyridine [BiPy (di-amino)] (0.63 mmol) (Carbosynth). The mixture is refluxed for at least 4 h under a nitrogen atmosphere at atmospheric pressure and at a temperature between 150° and 155° C. The solution is cooled to RT and solvent is removed by rotary evaporation. Cold water is added and the complex iron tris(BiPy)(di-amino)perchlorate is isolated by filtration.

BNPC Examples

Example 9

Anode Polymeric Bio-Nano Power Cells

Part A: Synthesis of Anode Complex+PVI

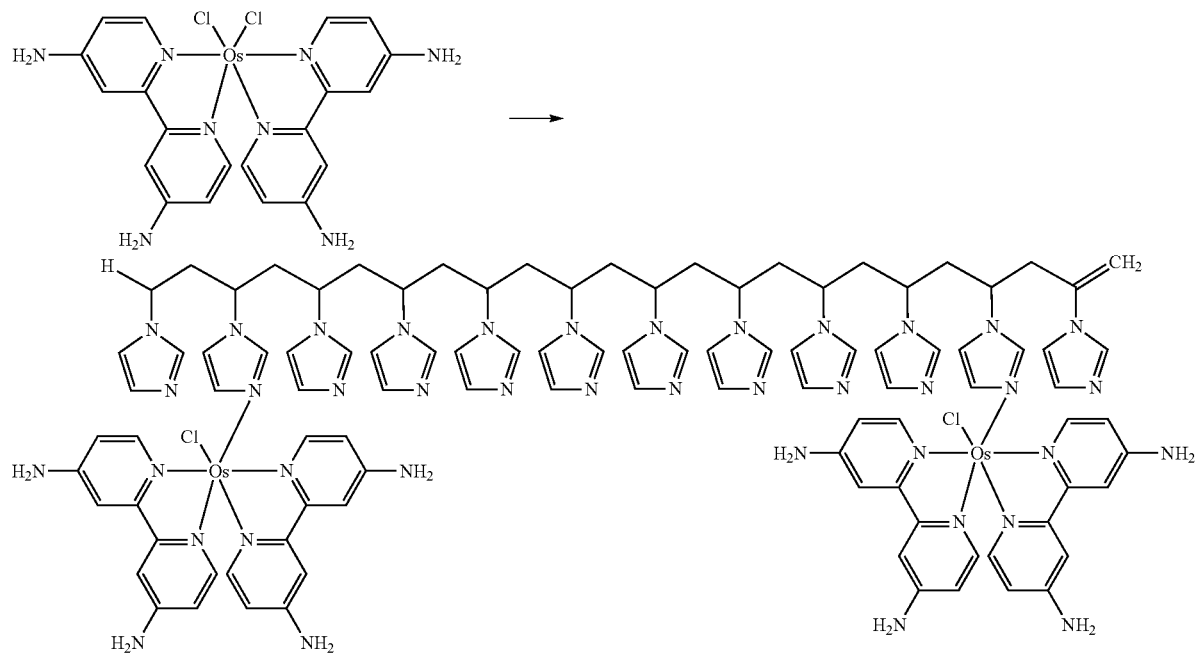

Osmium bis(BiPy)(di-amino)dichloro (0.28 g, 0.45 mmol) (from Example 1) was added to a three-neck flask, containing 150 mL of ethanol, and then it was flushed by nitrogen gas for 30 minutes. Poly (1-vinylimidazole) (from Example C) solution (0.51 g of polymer dissolved in 25 mL of ethanol) was added into flask, and the reaction was refluxed for 24 hours. When reaction finished, filtration was carried to remove solid materials. The filtrate was dripped to 1000 mL of diethyl ether to crystallize product. Its spectra are:

IR (Neat): $V_{max}$ 3335, 3196, 3110, 1622, 1504, 1416, 1228, 1083, 1025, 916 cm$^{-1}$;

Part B: Synthesis of Anode Polymer Complex+G1 Dendrimer

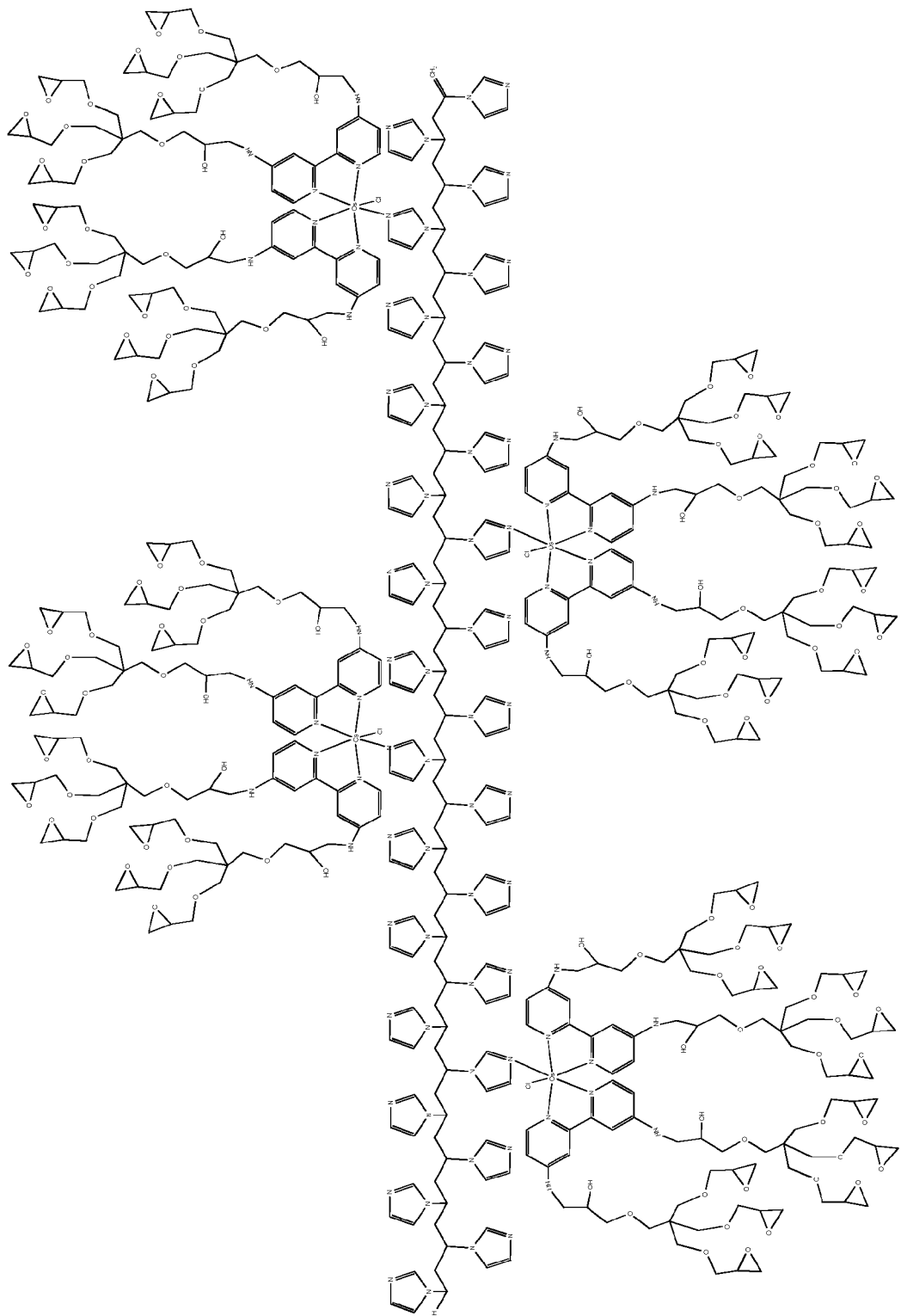

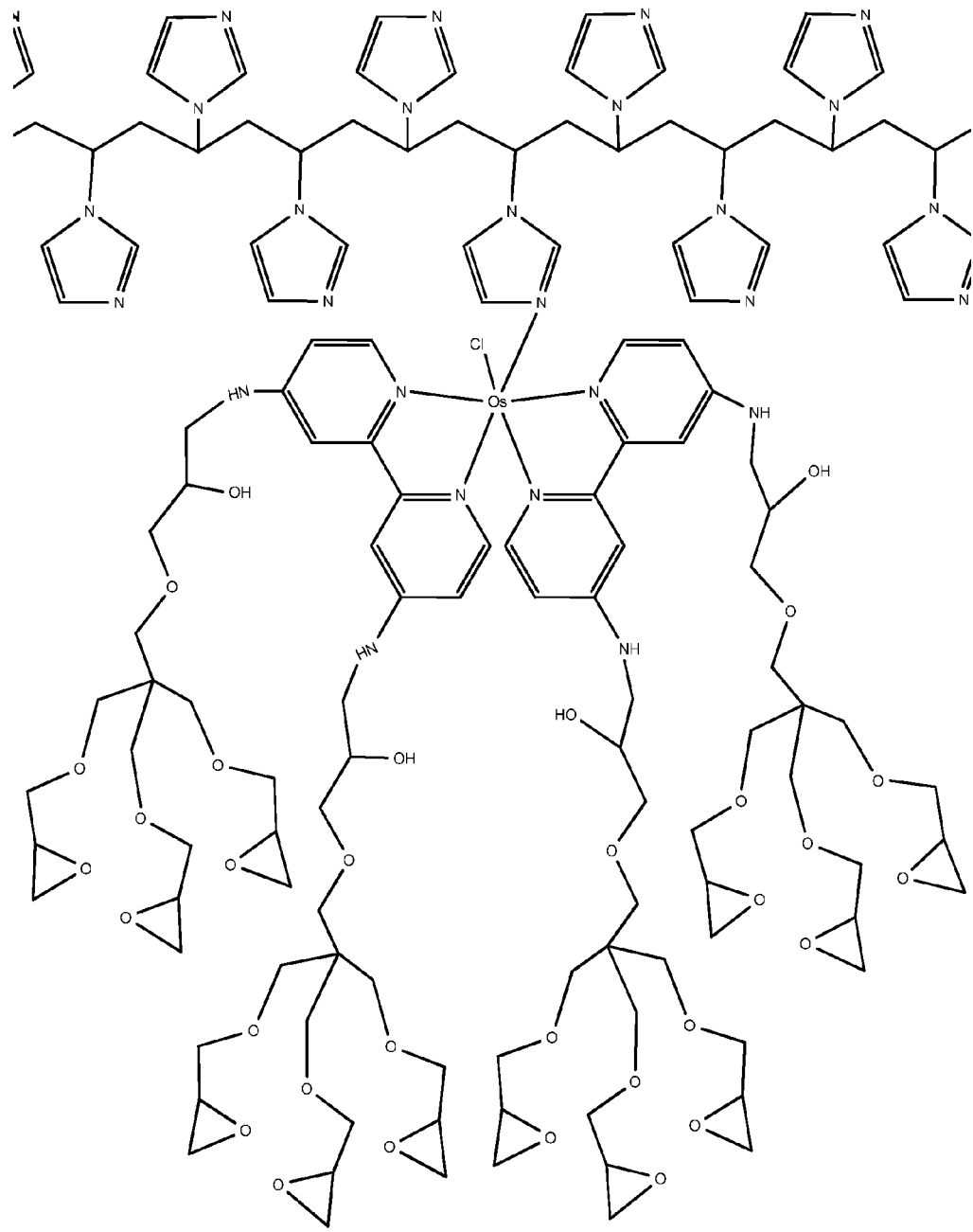

The above chemical structure illustrates one dendron molecule as enlarged from the immediately preceding chemical structure as attached to a portion of the backbone.

Compound of poly (1-vinylimidazole) with osmium complex (0.50 g) (from Example 9A) and PETGE (0.41 g, 1.14 mmol) were added to a 50 mL round-bottomed flask, followed by 24 mL of methanol. The reaction was carried out at 55° C. for 24 hours to finish it. The reaction crude was dripped into 400 mL diethyl ether to crystallize Anode Polymer Complex G1 Dendrimer product. (0.63 g) and its spectra are:

$^1$H NMR (300 MHz, CD$_3$OD): δ: 3.92-3.82 (b), 3.60-3.34 (b), 3.40-3.33 (b), 3.33-3.28 (b), and $^{13}$C NMR (75 MHz, CD$_3$OD): δ: 74.25, 72.80, 70.09, 69.29, 58.32, 45.78.

Figure 19:
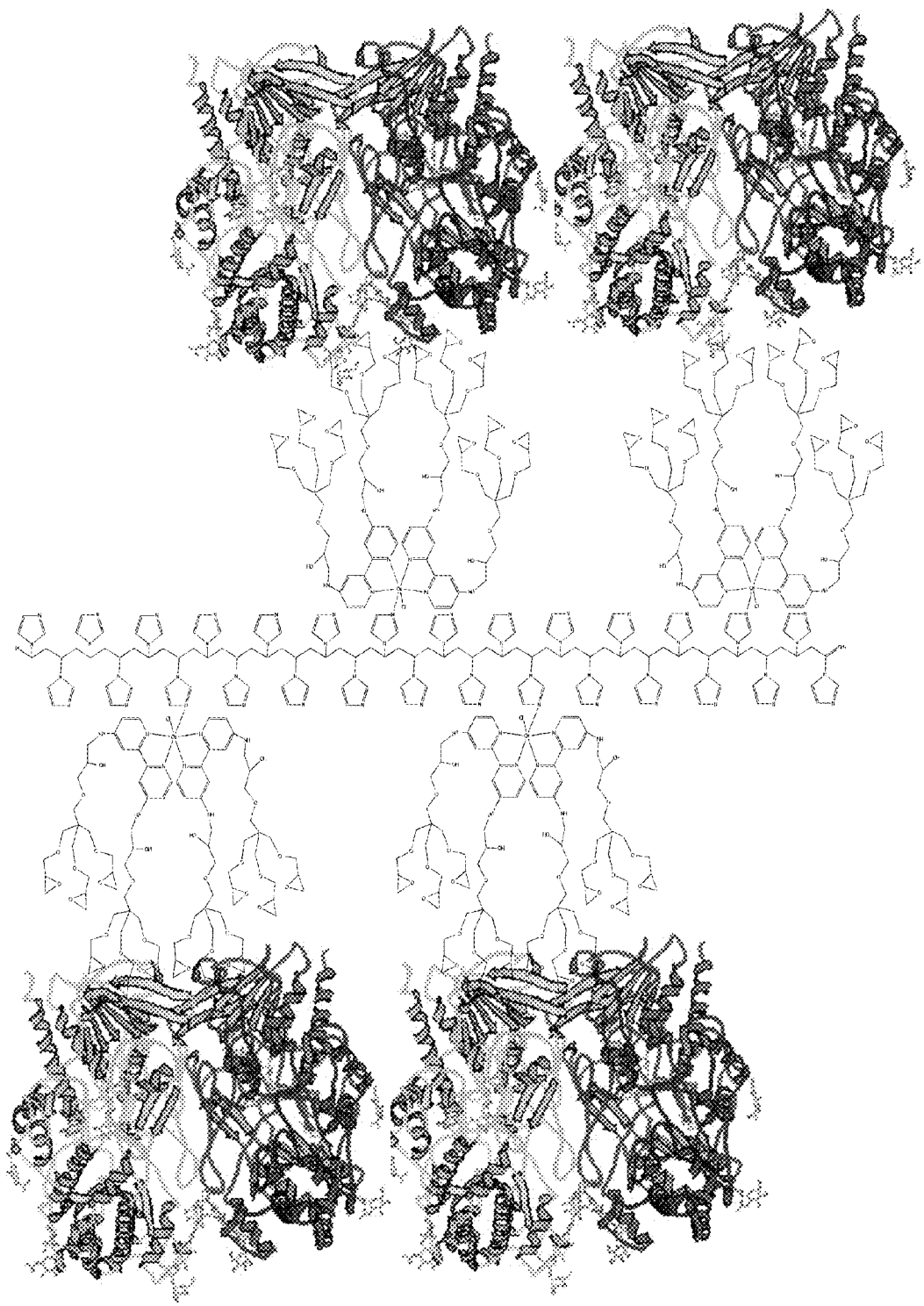
FIG. 19 is a depiction of the chemical structure of an anode polymer complex+G1 dendrimer+glucose oxidase (color portion) of Example 9, Part C.

Part C: Synthesis of Anode Polymer Complex+G1 Dendrimer+Glucose Oxidase; see FIG. 19 for the chemical structure of the product.

Compound of Anode Polymer Complex+G1 Dendrimer (10 mg) (from Example 9B) was dissolved in 1.5 mL 10% HEPES Solution. Glucose Oxidase (GOX) (10 mg) (Sigma-Aldrich) was dissolved in 1.5 mL 10% HEPES Solution. The two mixtures were combined, yielding the Anode Polymer Complex G1 Dendrimer+GOX product that has the following spectra:

HPLC: Starting Material: Example 9B: 4.36; GOX 3.97; Anode Polymer Complex+G1 Dendrimer+GOX (1 day): 5.38; Anode Polymer Complex+G1 Dendrimer+GOX (7 day): 6.18 and 7.32, indicating slow association of the Anode Polymer Complex+G1 Dendrimer with GOX.

Figure 20:
FIG. 20 is a photograph illustrating anode polymer complex G1 dendrimer+GOX product of Example 9, Part C.

Cyclic Voltametry: FIG. 20.

Part D: Synthesis of Anode Polymer Complex+G1.5 Dendrimer+PIPZ

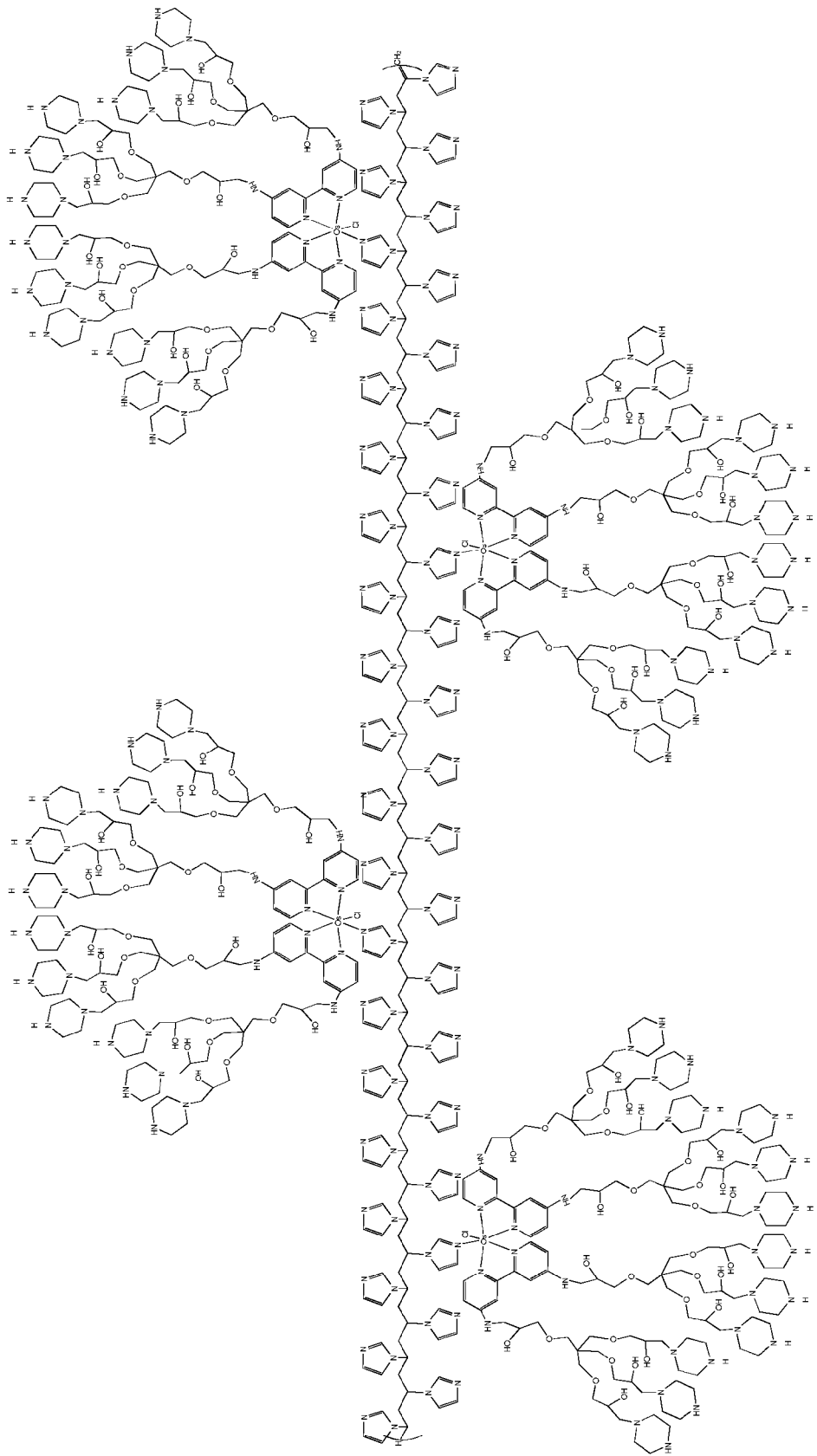

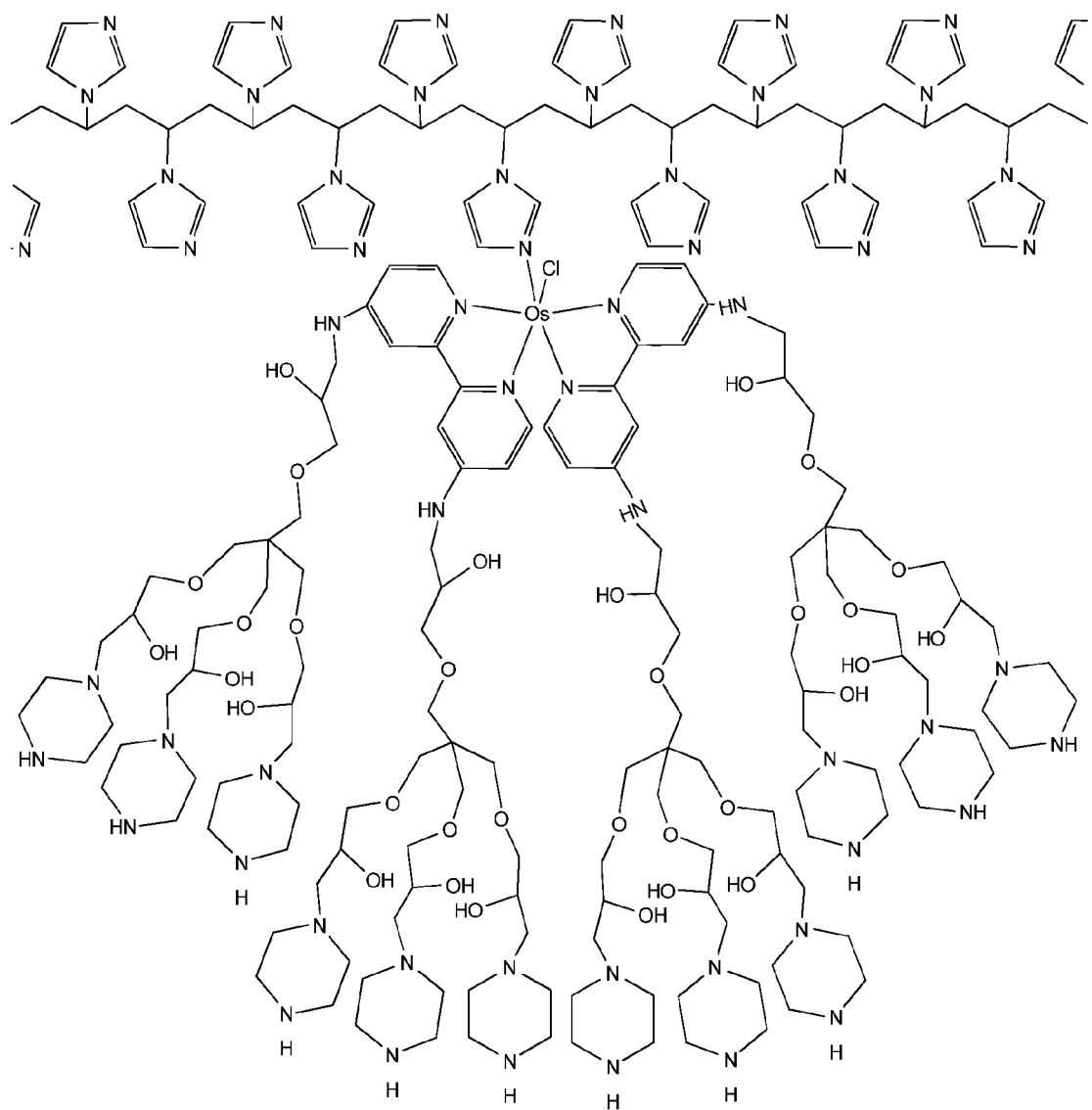

The above chemical structure illustrates one dendron molecule as enlarged from the immediately preceding chemical structure as attached to a portion of the backbone.

a) Ethyl N-piperazinecarboxylate (1.08 g, 6.83 mmol) and anode polymer G1 dendrimer (0.5 g) (from Example 9B) were added a 50 mL round-bottomed flask, followed by 20 mL of methanol. The reaction was carried out at 55° C. for 8 hours, then solvent was removed by rotary evaporator.

b) A 10 mL of potasium hydroxide solution (0.57 g of KOH dissolved in 10 mL $H_2O$) and 10 mL of methanol were added to flask, and then refluxed for 24 hours. The pH of reaction crude was adjusted to 8 by HCl, and then dried by rotary evaporator. A 15 mL of methanol was added to dissolve product, and insoluble materials were removed by filtration. The filtrate was dripped into 400 mL diethyl ether to crystallize piperazine-terminated G1.

Part E: Synthesis of Anode Polymer G2 Dendrimer

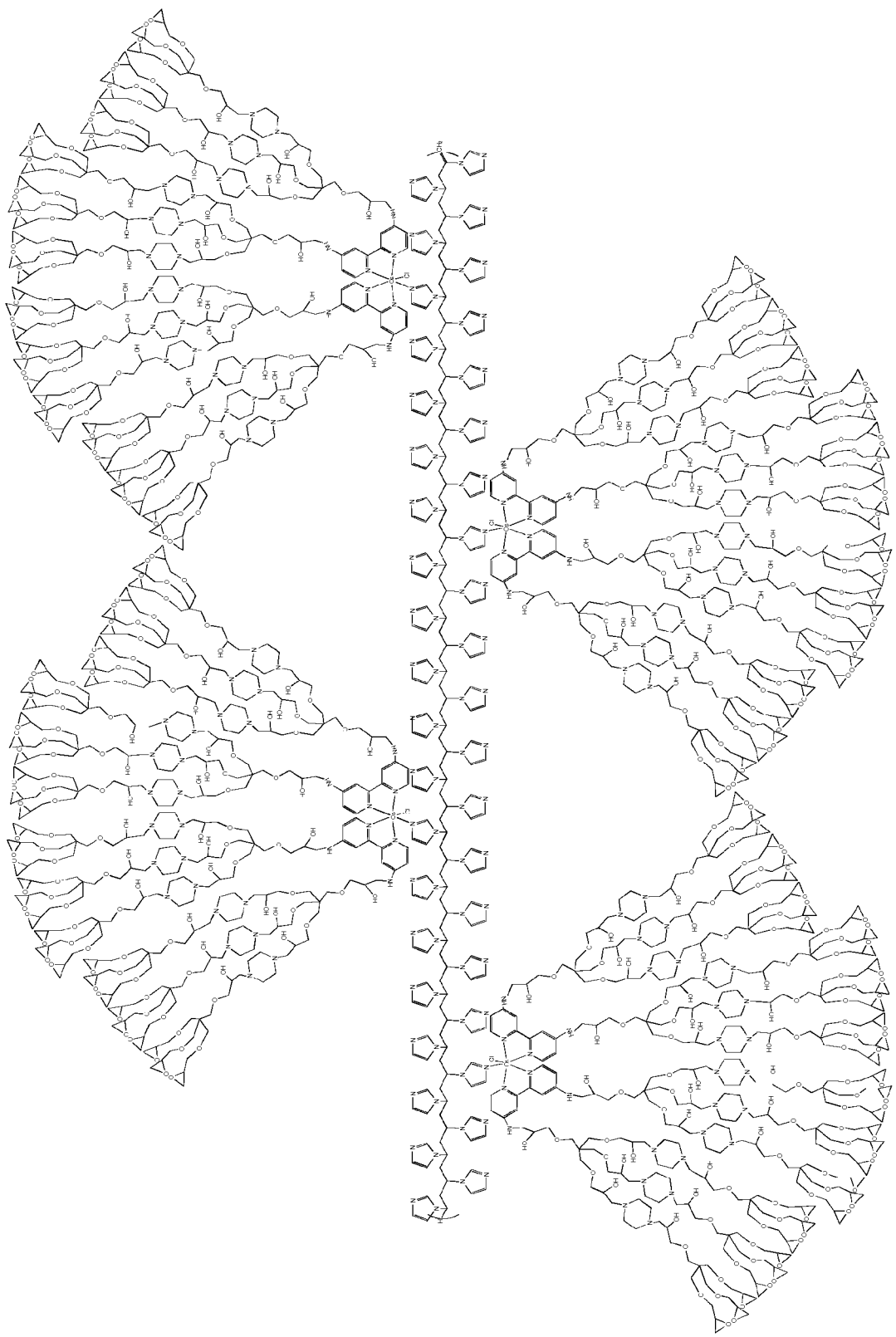

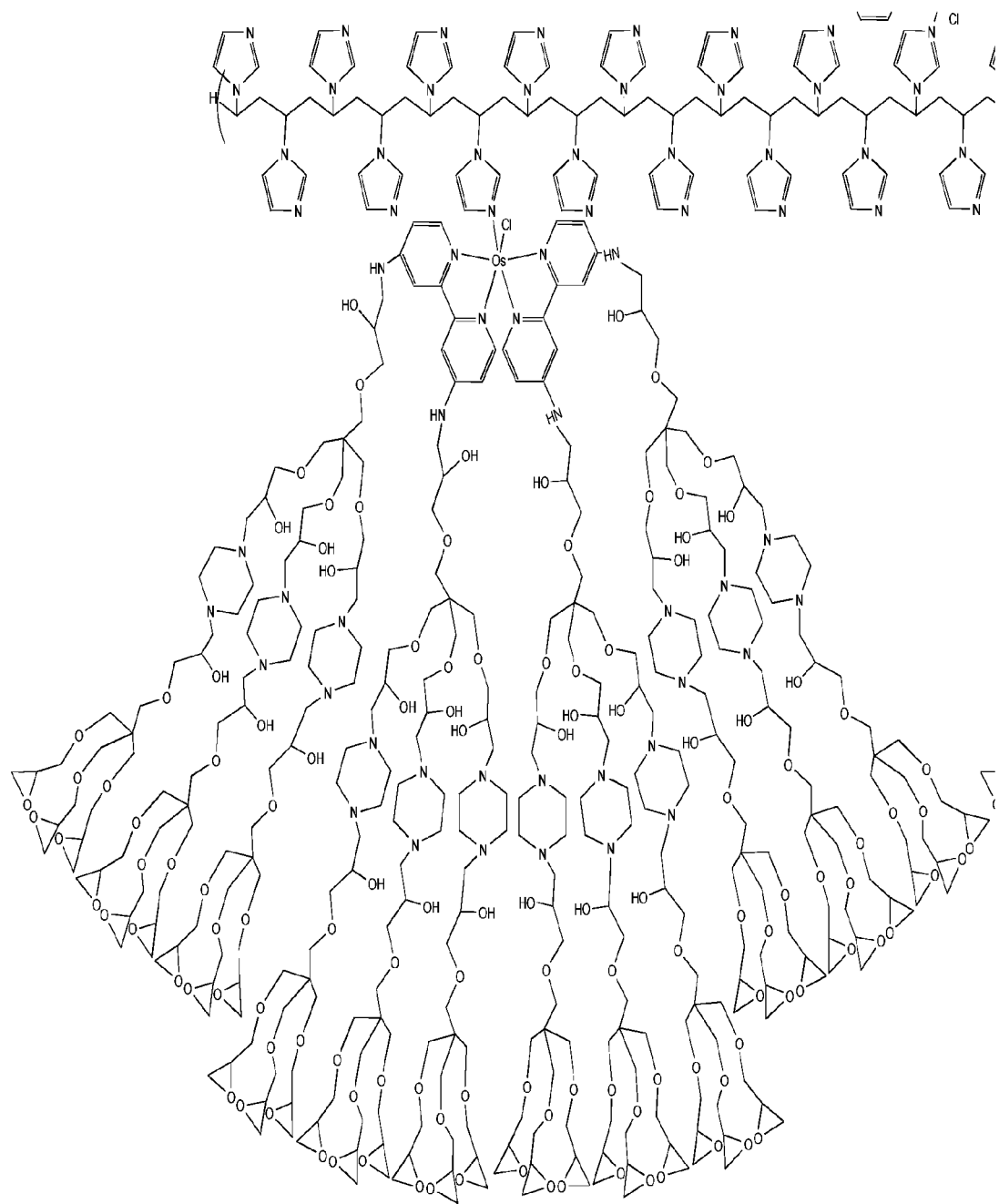

The above chemical structure illustrates one dendron molecule as enlarged from the immediately preceding chemical structure as attached to a portion of the backbone.

Anode Polymer Complex+G1.5 Dendrimer+PIPZ (from Example 9D) and PETGE (2.45 g, 6.83 mmol) were added to a 50 mL round-bottomed flask, followed by 20 mL of methanol. The reaction was carried out at room temperature for 6 hours. When reaction finished, the crude was dripped into 400 mL diethyl ether to crystallize anode polymer G2 dendrimer. (1.26 g) and its spectra are:

$^1$H NMR (500 MHz, CD$_3$OD): δ: 7.6-6.3 (b), 4.4-3.7 (b), 3.5, 3.4-2.80 (b), 2.4-2.2 (b) 2.2-1.6 (b) and $^{13}$C NMR (75 MHz, CD$_3$OD): δ: 73.52, 72.64, 70.03, 68.75, 62.69, 58.64.

Part F: Synthesis of Anode Polymer G2.5 Dendrimer

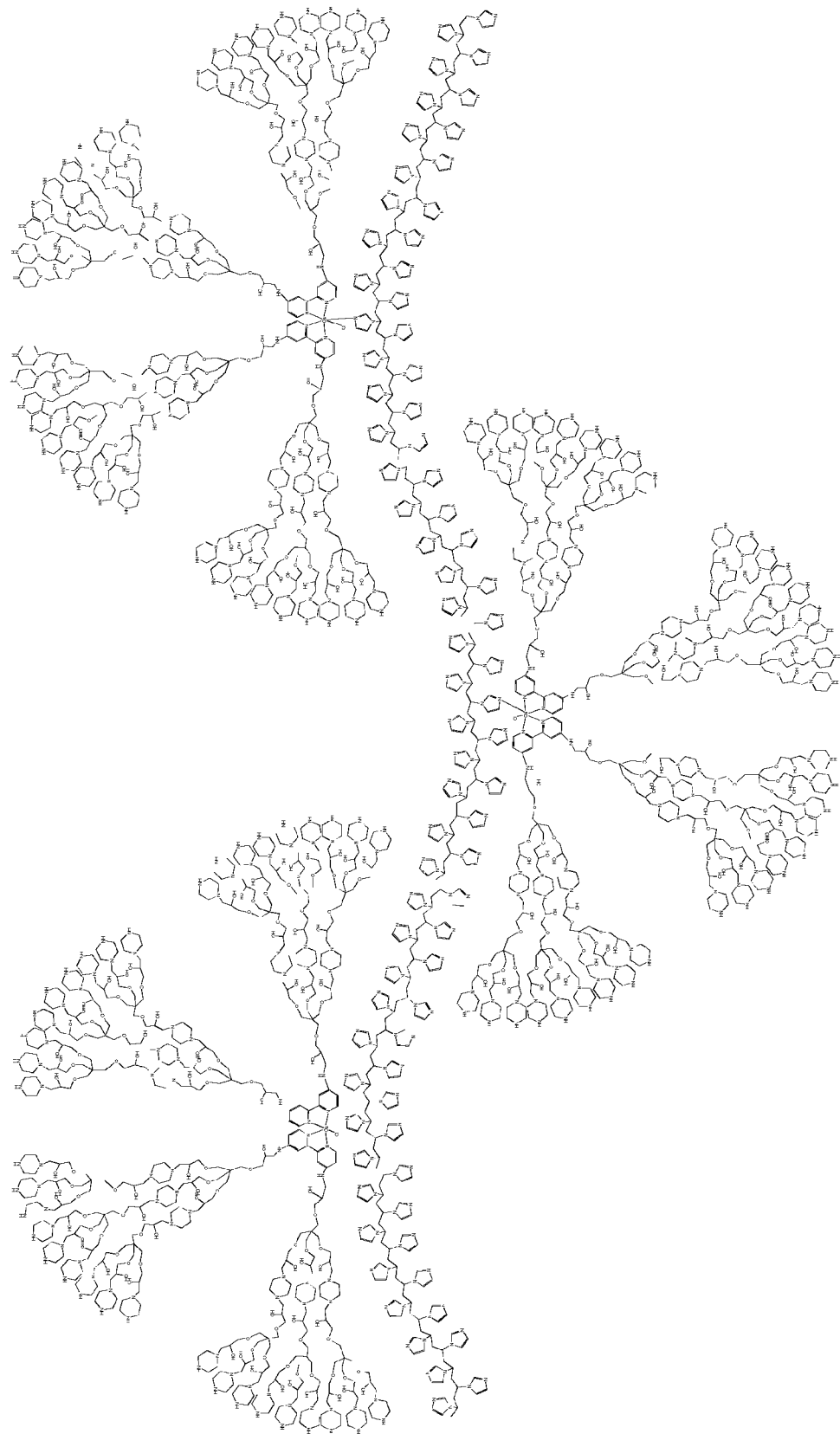

81 82
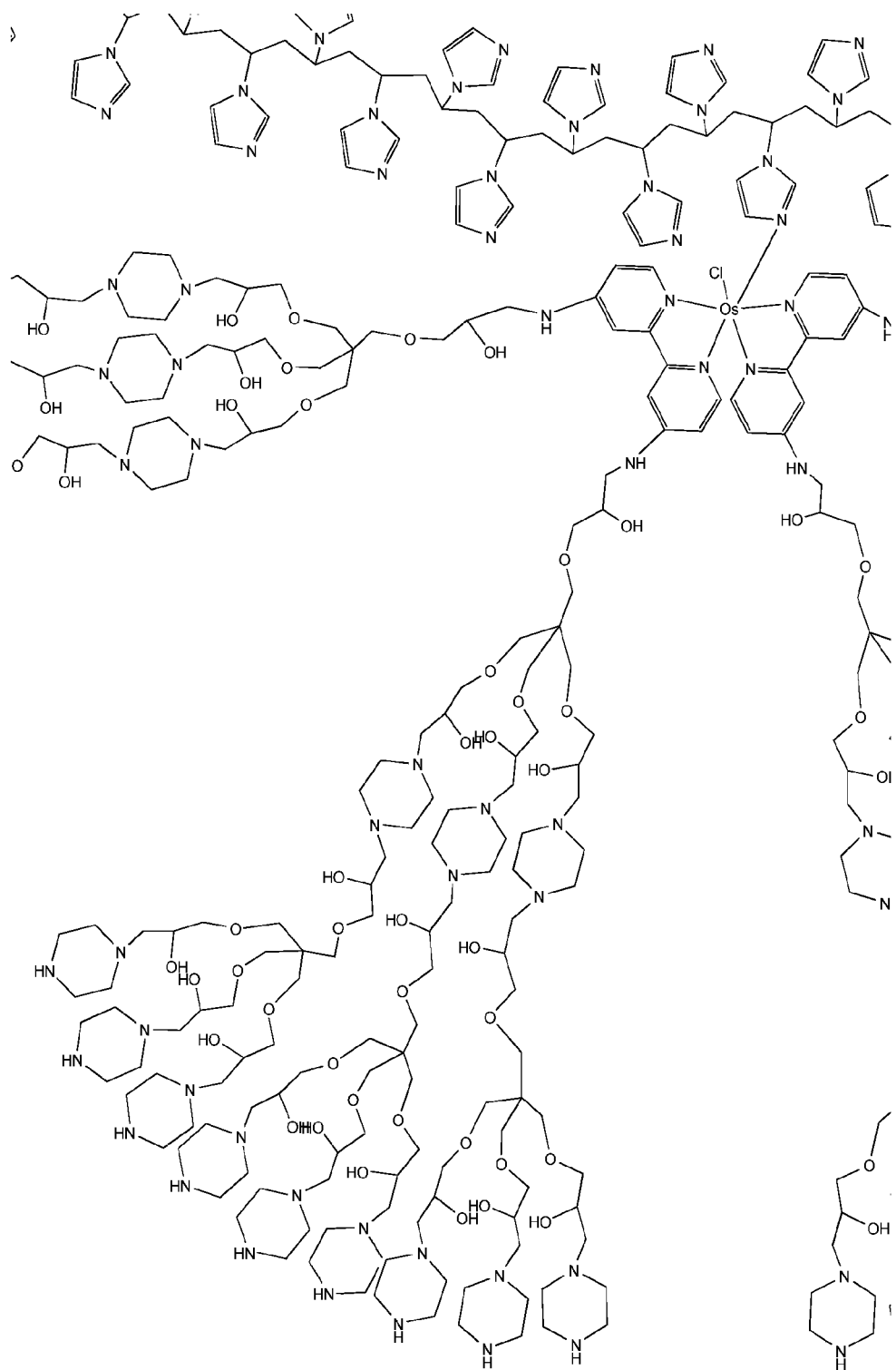

The above chemical structure illustrates one arm of a dendron molecule as enlarged from the immediately preceding chemical structure as attached to a portion of the backbone.

a) Ethyl N-piperazinecarboxylate (2.72 g, 17.23 mmol) and Anode Polymer G2 dendrimer (0.42 g) (from Example 9E) were added a 50 mL round-bottomed flask, followed by 20 mL of methanol. The reaction was carried out at 55° C. for 8 hours, then solvent was removed by rotary evaporator.

b) A 12 mL of potasium hydroxide solution (1.44 g of KOH dissolved in 12 mL $H_2O$) and 12 mL of methanol were added to flask, and then refluxed for 24 hours. The pH of reaction crude was adjusted to 8 by HCl, and then dried by rotary evaporator. A 15 mL of methanol was added to dissolve product, and insoluble materials were removed by filtration. The filtrate was dripped into 400 mL diethyl ether to crystallize piperazine-terminated G2.

Part G: Synthesis of Anode Polymer G3 Dendrimer

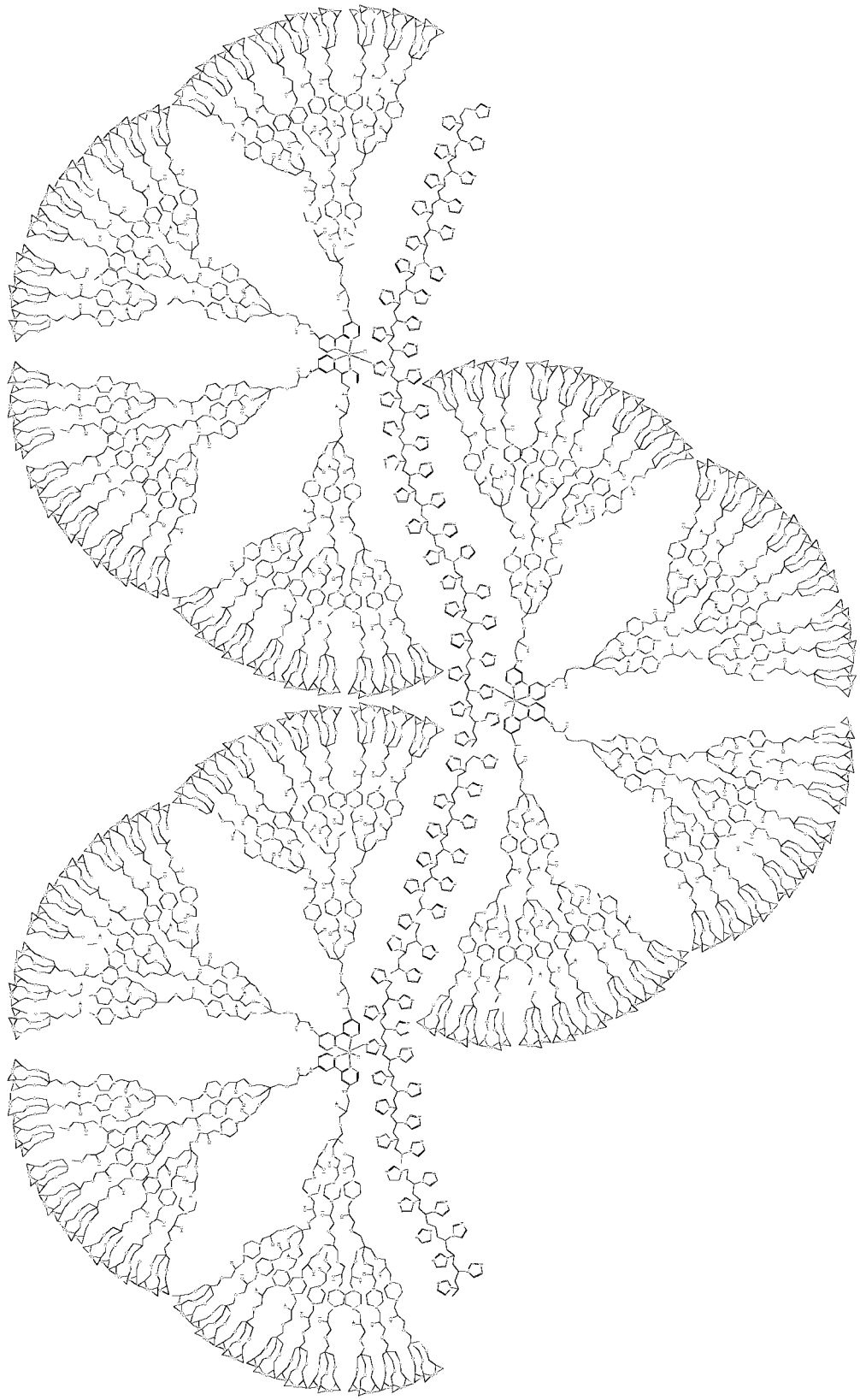

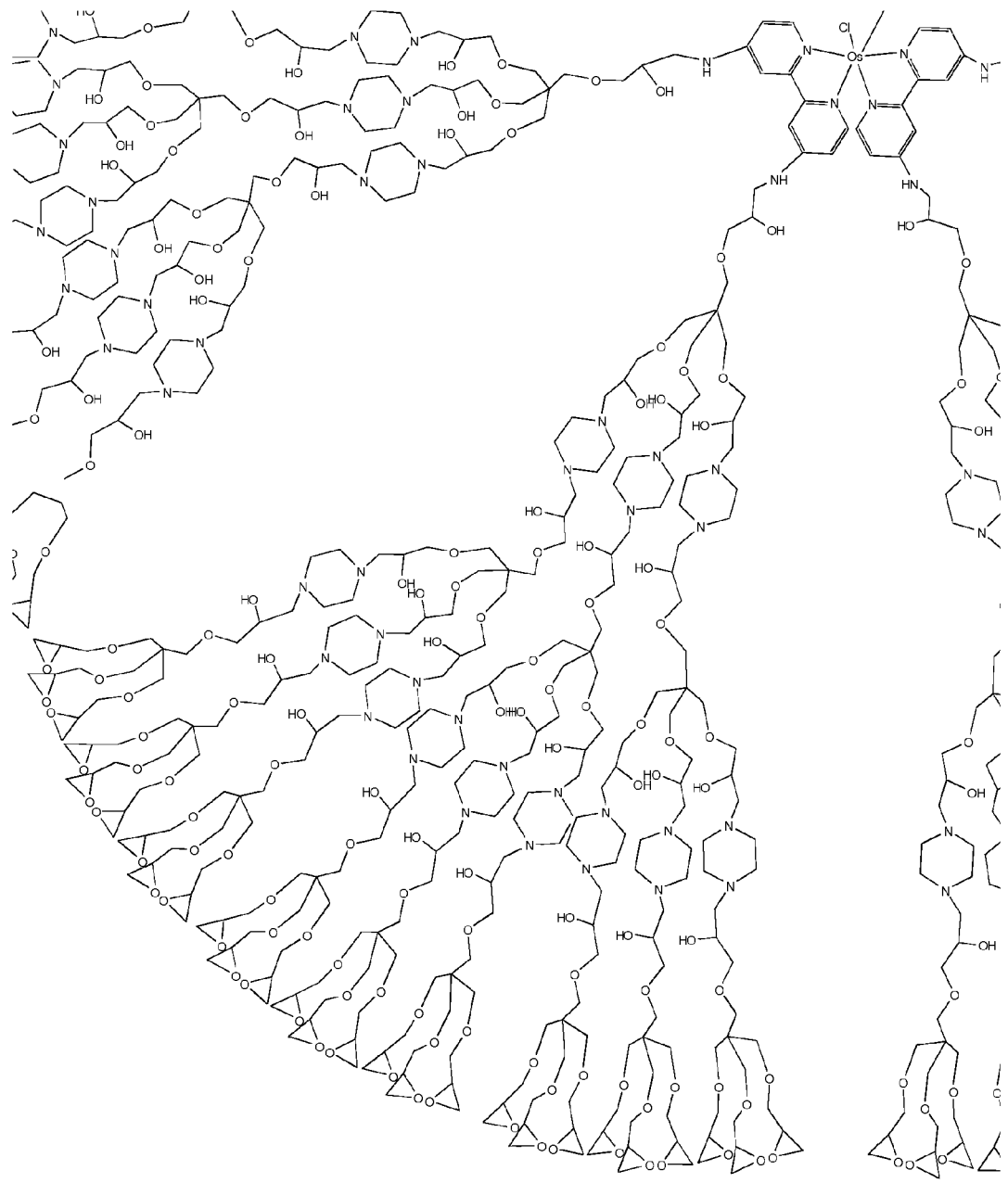

The above chemical structure illustrates one arm of a dendron molecule as enlarged from the immediately preceding chemical structure as attached to a portion of the backbone.

Anode Polymer Complex+G2.5 Dendrimer+PIPZ (from Example 9F) and PETGE (7.17 g, 17.15 mmol) were added to a 50 mL round-bottomed flask, followed by 30 mL of methanol. The reaction was carried out at room temperature for 6 hours. When reaction finished, the crude was dripped into 400 mL diethyl ether to crystallize Anode Polymer G3 dendrimer. Yield: 1.68 g

Example 10

Synthesis of Bio-Nano Power Cell (Anode)

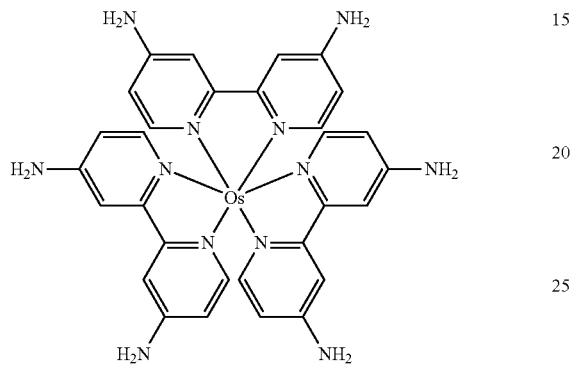

Part A: Anode Complex

Prepare Anode Complex by the procedure of Example 2.

Part B: Anode Complex G1

91 92
Anode Complex + PETGE →
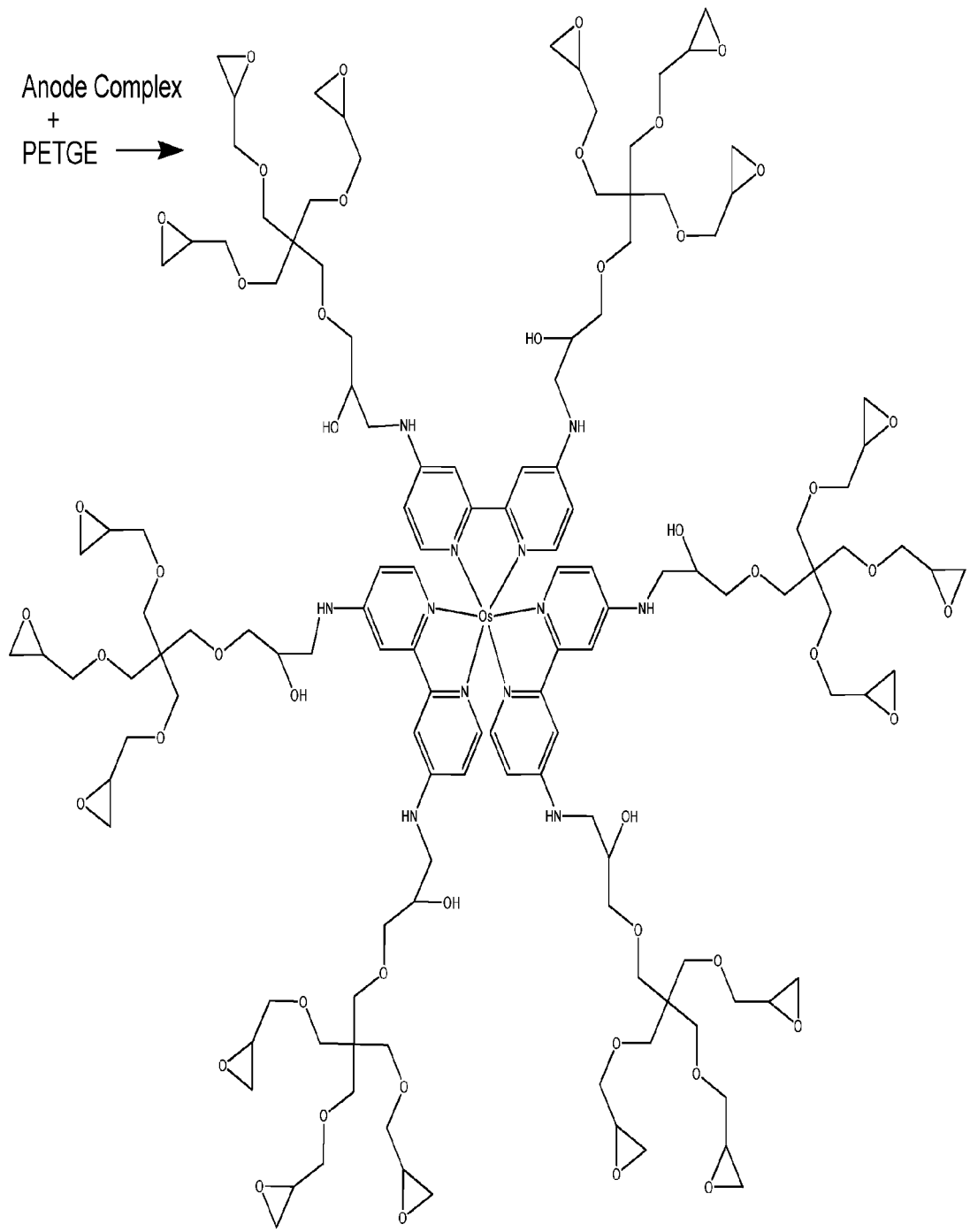

Osmium tris(4,4'-diamino-2,2'-bipyridine) (0.24 g, 0.23 mmol) (from Example 2) and PETGE (0.52 g, 1.43 mmol) were added to a 50 mL round-bottomed flask, followed by 15 mL of DMF and 10 mL of methanol. Reaction was carried out at 55° C. for 24 hours. When reaction finished, crude was dripped into 400 ml diethyl ether to crystallize product. (0.44 g).

Part C: Synthesis of Anode Complex G1.5 Dendrimer+PIPZ Linker; see FIG. 27 for the Reaction Scheme.

Anode G1 Dendrimer + PIPZ →
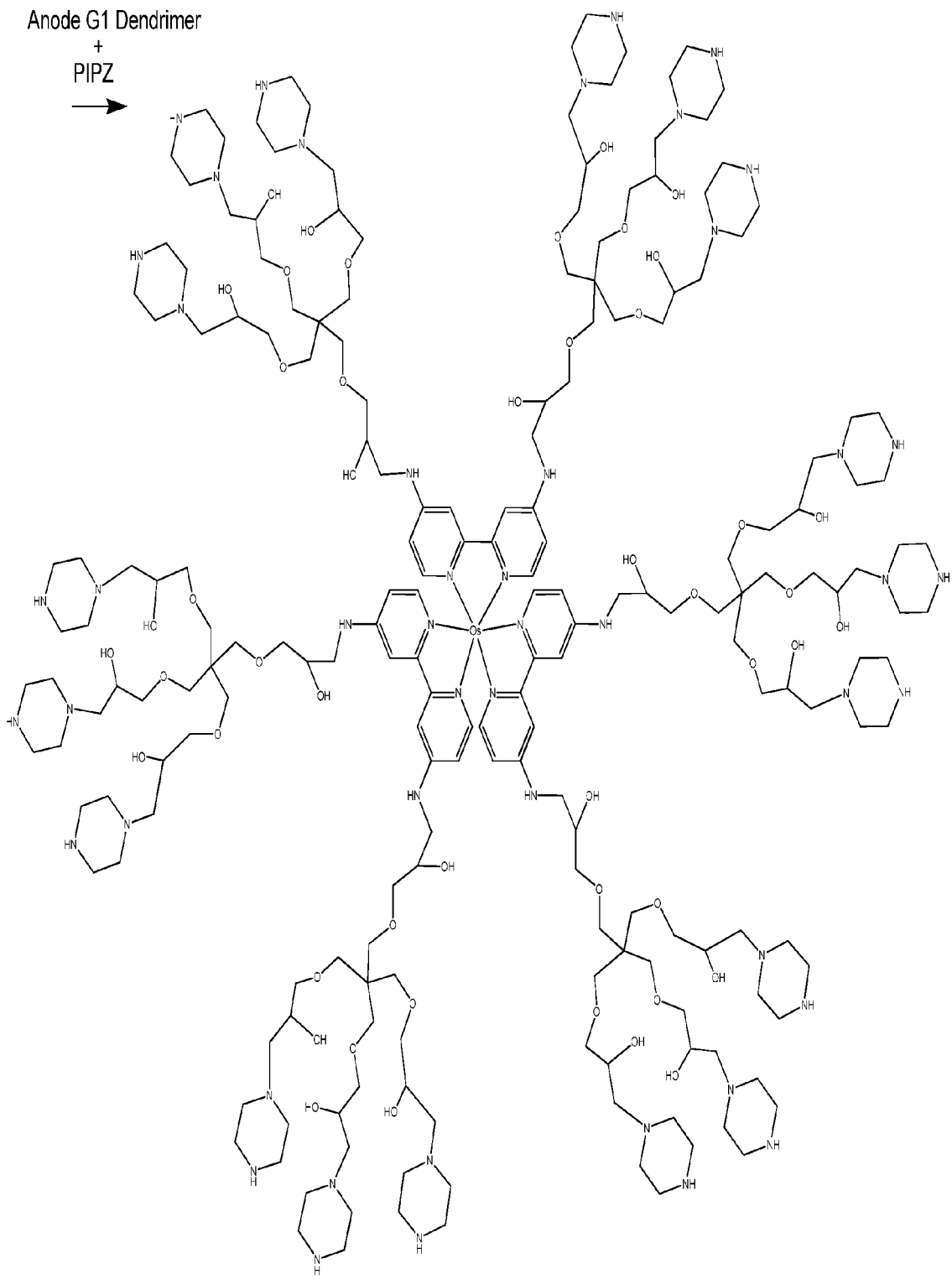

a) Ethyl N-piperazinecarboxylate (0.55 g, 3.47 mmol) and Anode Complex G1 Dendrimer (0.56 g) (from Example 10, Part B) is added a 50 mL round-bottomed flask, followed by 20 mL of methanol. The reaction is carried out at 55° C. for 12 hours, then solvent is removed by rotary evaporator.

b) A 10 mL of potasium hydroxide solution (0.30 g of KOH dissolved in 10 mL $H_2O$) and 10 mL of methanol are added to flask, and then refluxed for 24 hours. The pH of reaction crude is adjusted to 8 by HCl, and then dried by rotary evaporator. A 15 mL of methanol is added to dissolve product, and insoluble materials are removed by filtration. The filtrate is dripped into 400 mL diethyl ether to crystallize Anode Complex G1.5 Dendrimer+PIPZ.

Part D: Synthesis of Anode Complex G2 Dendrimer

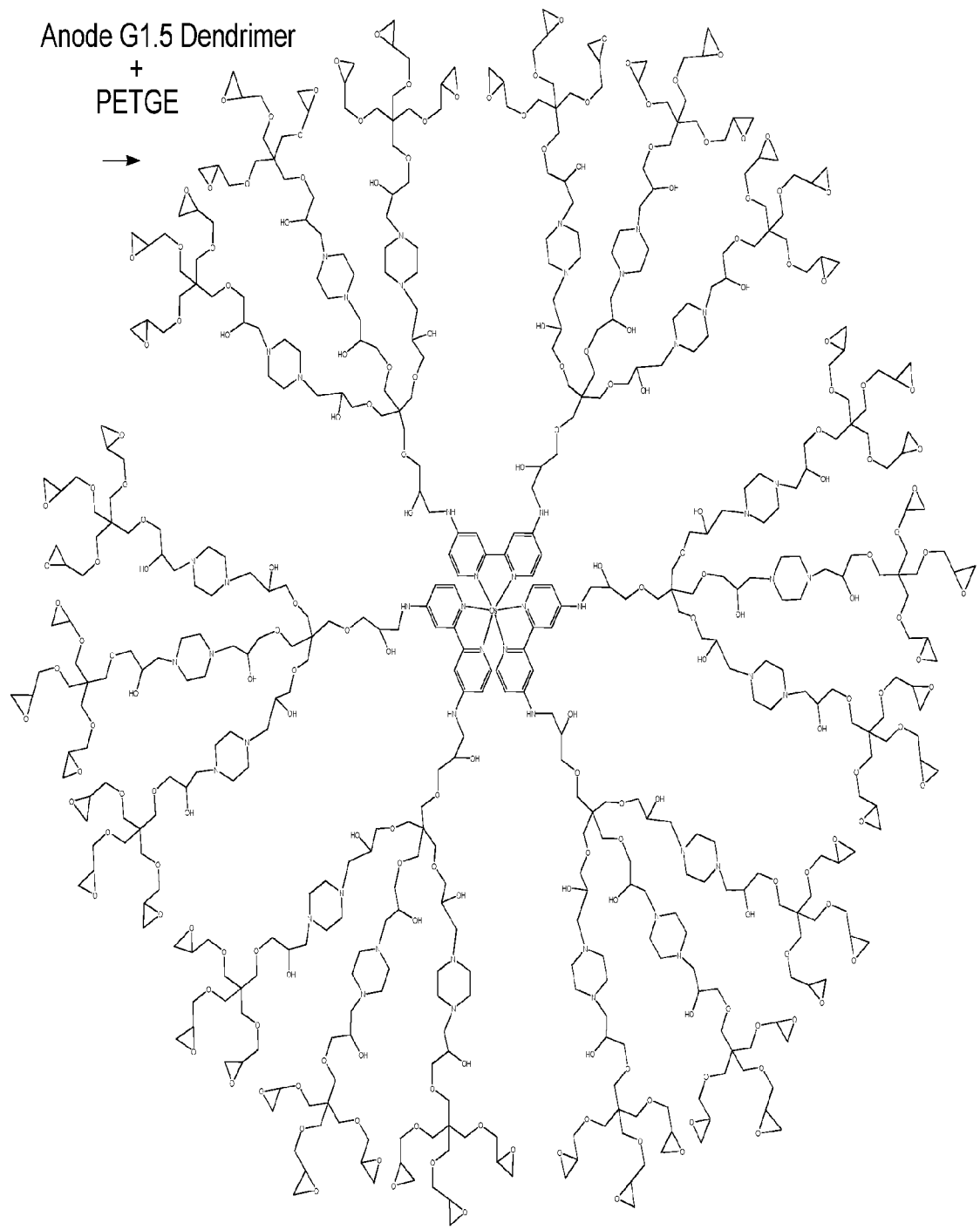

101 102
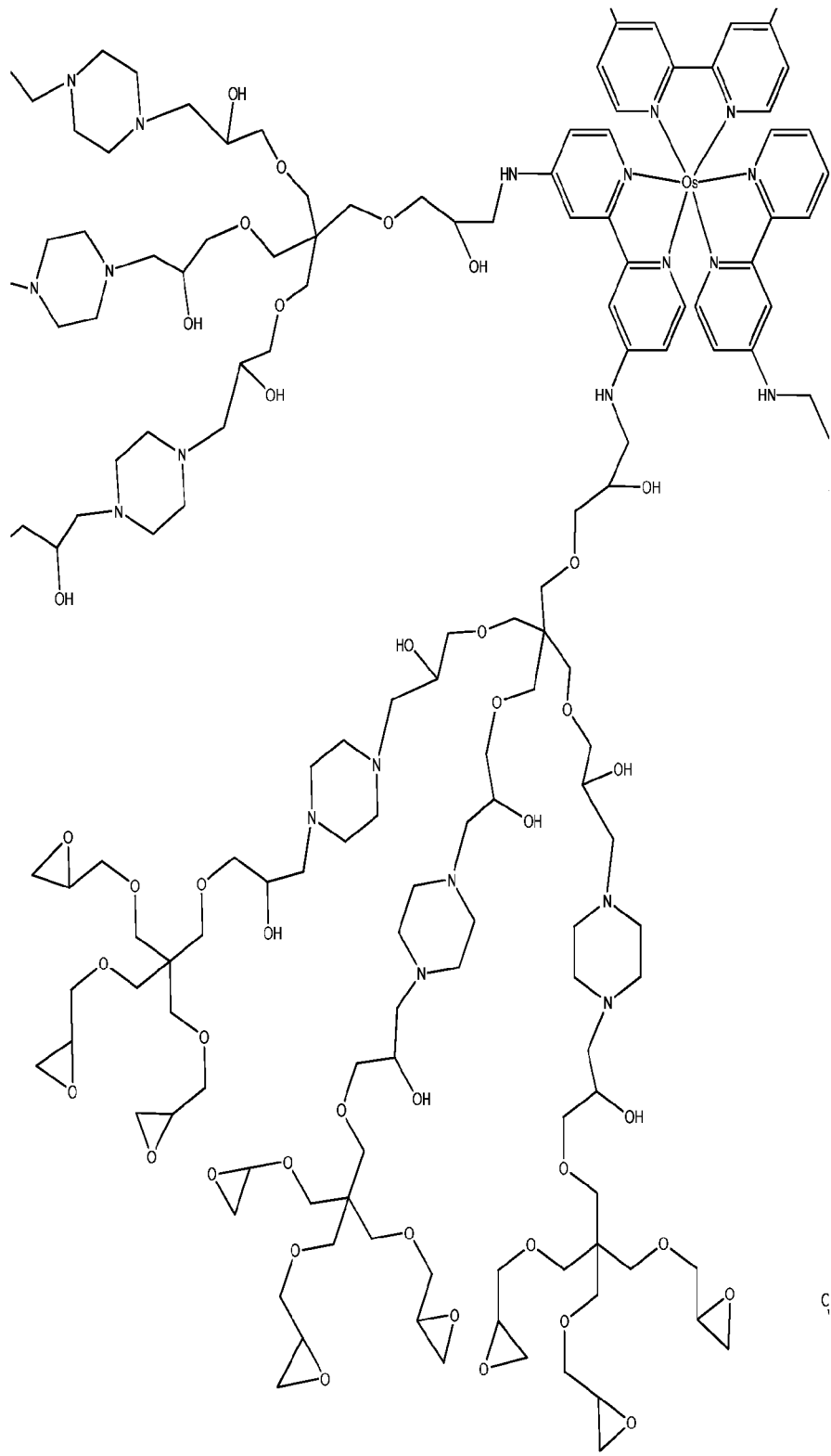

The above chemical structure illustrates one arm of a dendron molecule as enlarged from the immediately preceding chemical structure as attached to the core.

Anode Complex G1.5 Dendrimer-PIPZ (made from Example 10, Part C) and PETGE (1.27 g, 3.52 mmol) is added to a 50 mL round-bottomed flask, followed by 30 mL of methanol. The reaction is carried out at room temperature for 6 hours. When the reaction is finished, the crude is dripped into 400 mL diethyl ether to crystallize Anode Complex G2 Dendrimer.

Part E: Synthesis of Anode Complex G2 Dendrimer+DEIDA Surface

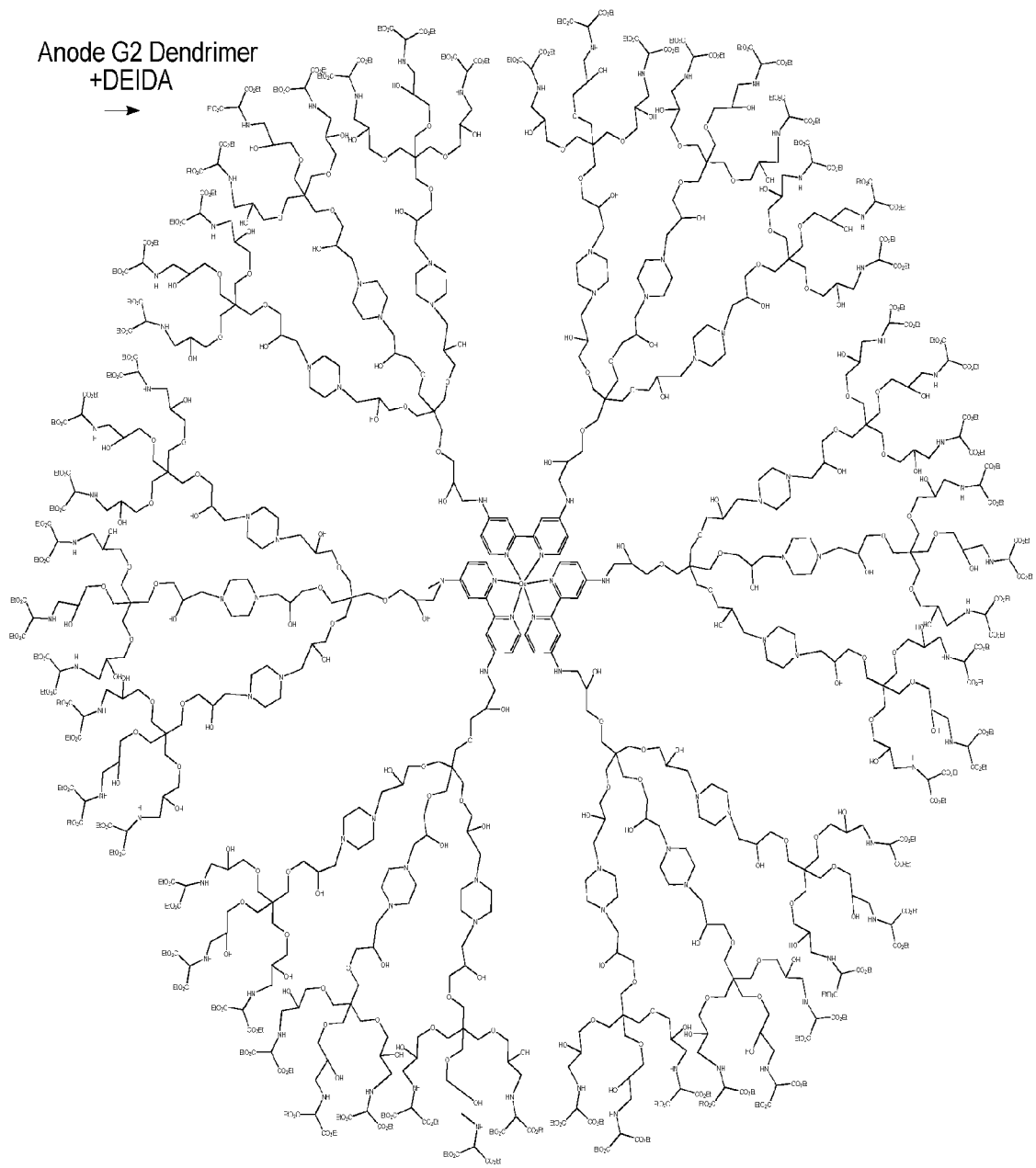

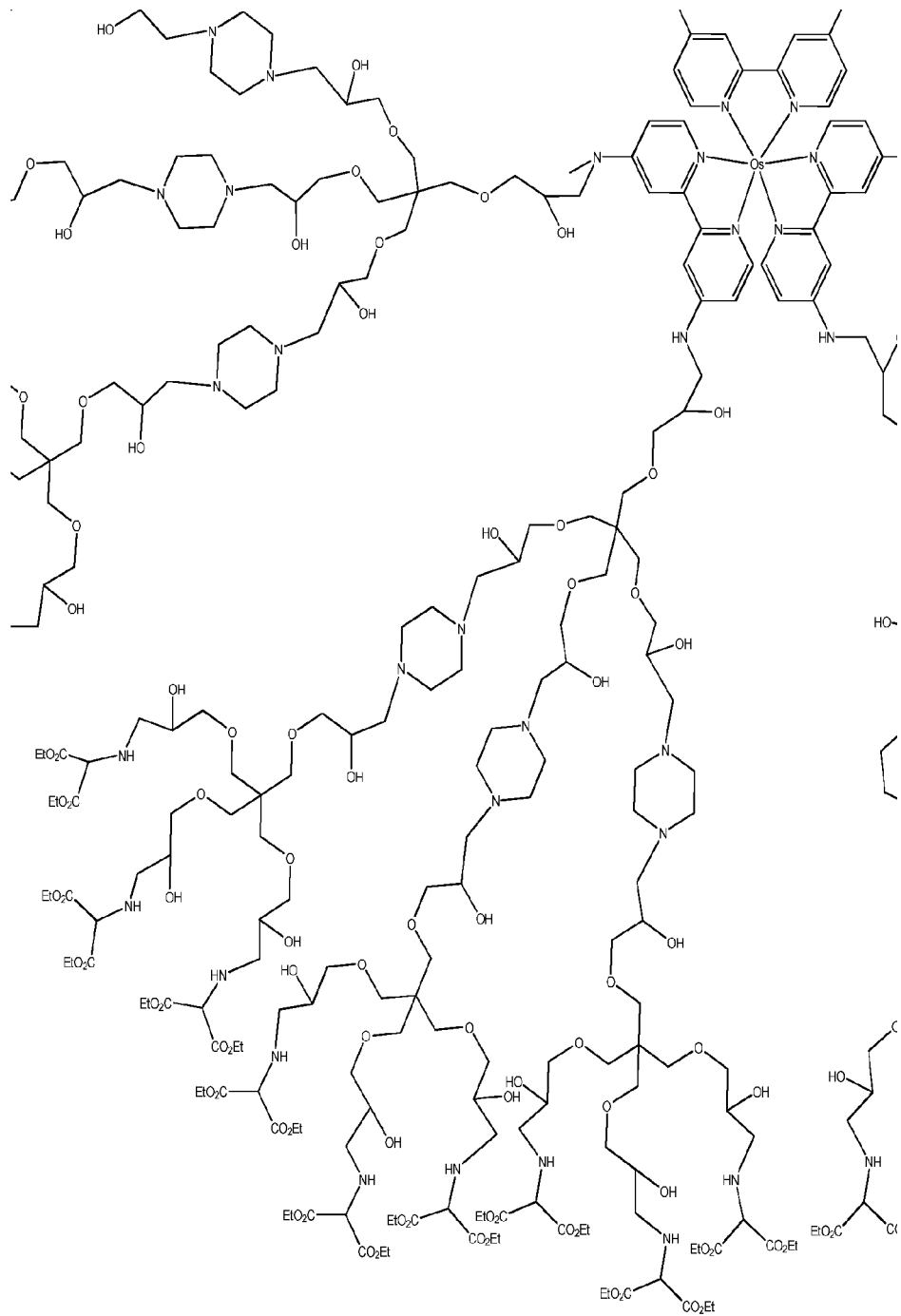

The above chemical structure illustrates one arm of a dendron molecule as enlarged from the immediately preceding chemical structure as attached to the core.

In a round bottom flask, add Anode Complex G2 Dendrimer (2 mmol, made from Example 10, Part D), MeOH and a solution of DEIDA (7.5 mmol) (Aldrich) in MeOH. Heat at 60° C. for 24 hours.

Example 11
Synthesis of Cathode Power Cells Complex

Part A: Synthesis of Cathode Transition Metal Complex

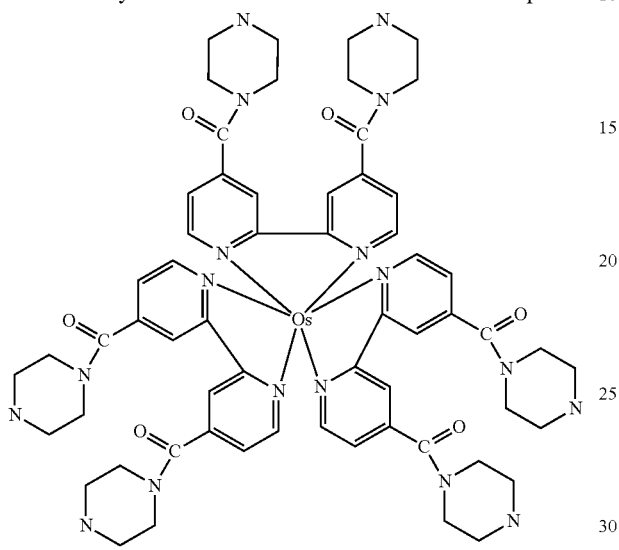

Prepare using procedure from Example 4.

Part B: Synthesis of G1 Dendrimer

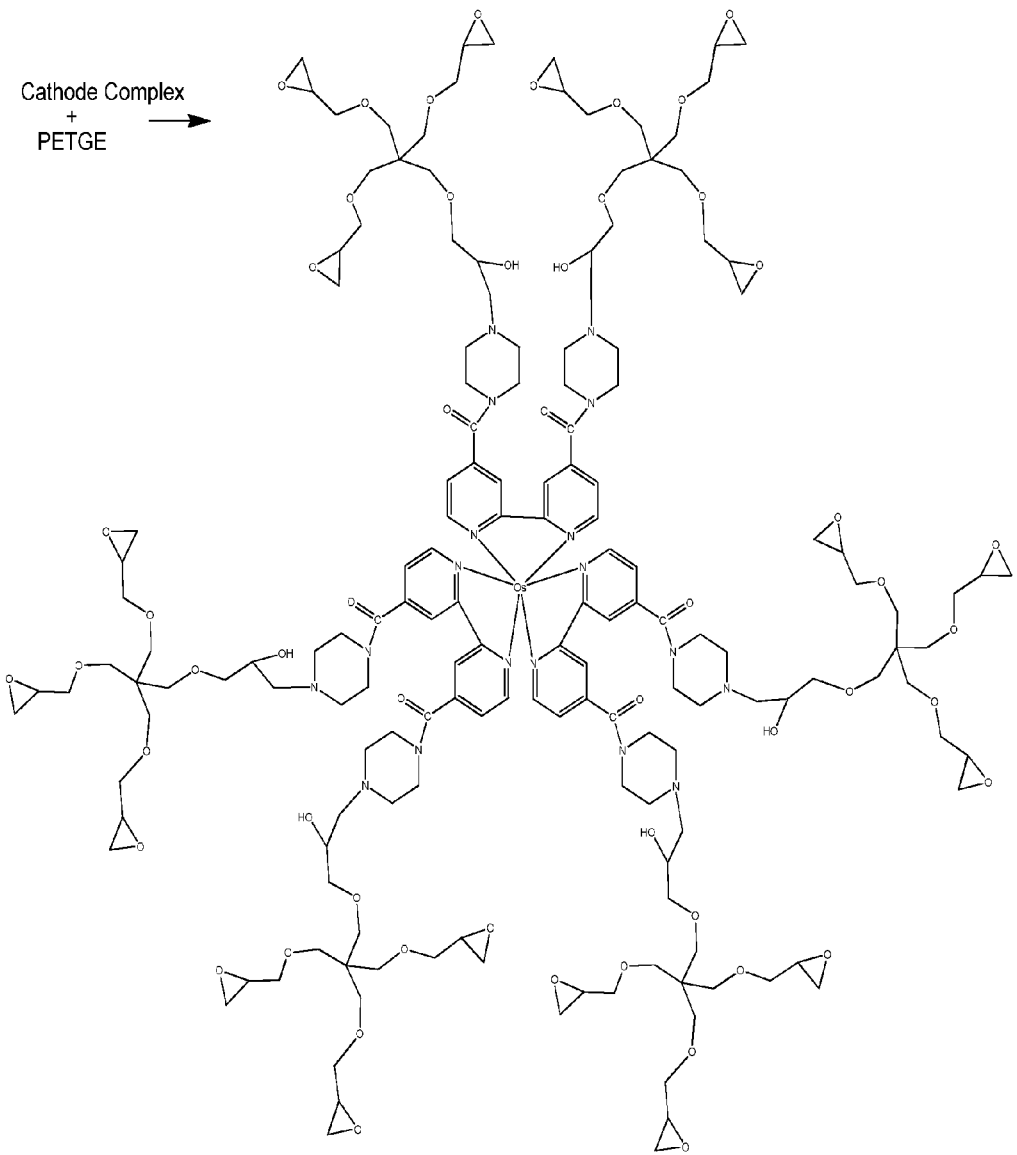

113 114
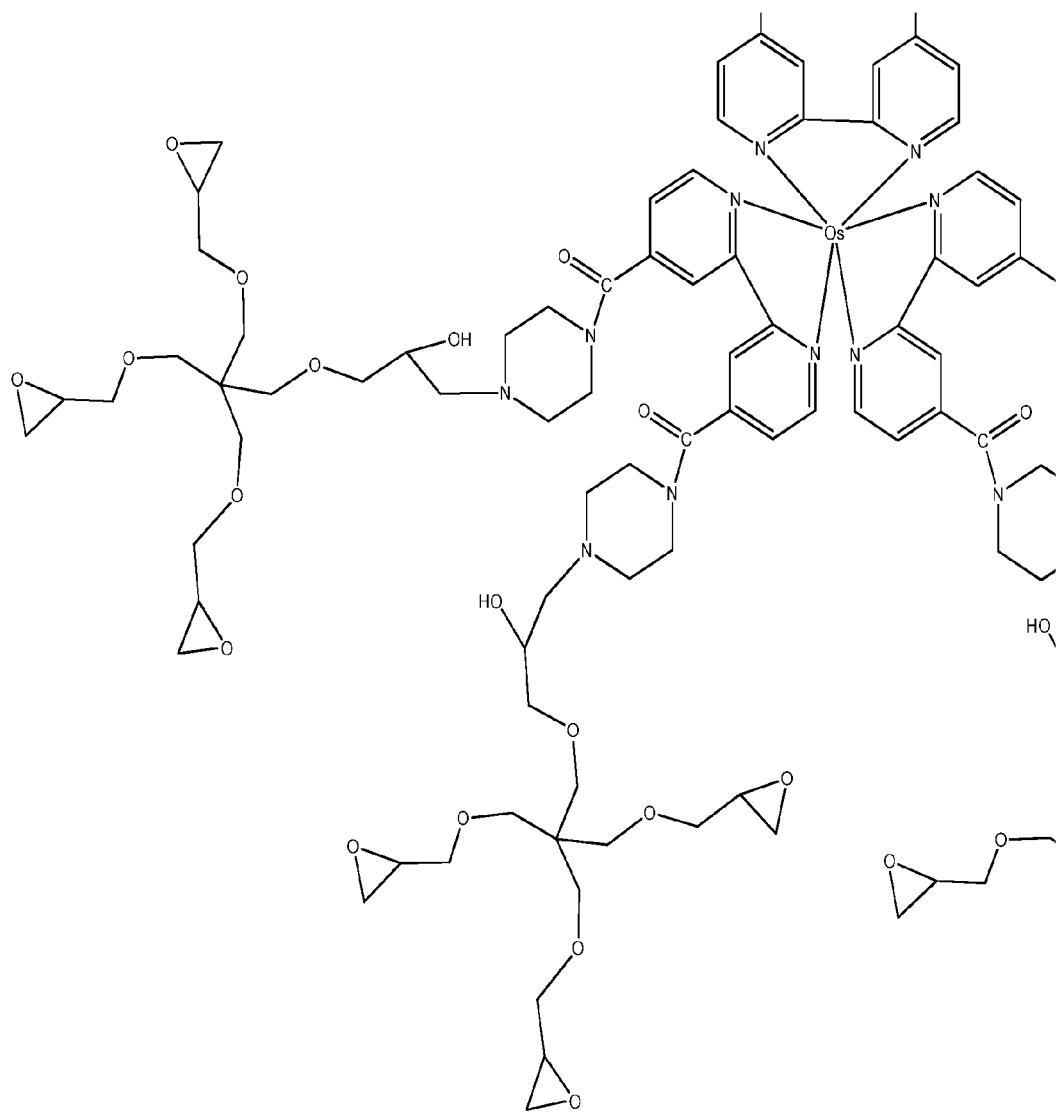

The above chemical structure illustrates two arms of a dendrimer molecule as enlarged from the immediately preceding dendrimer chemical structure as attached the core.

To a round bottom flask containing a stir bar, add PETGE (14.6 mmol) and MeOH. To this mixture add tris(bipyridine-di(carboxypiperazine) osmium (Cathode complex, prepared in Example 11, Part A) (1.25 mmol). Heat this mixture for 3 days at 50° C. under a $N_2$ atmosphere.

Part C: Synthesis of Cathode G1.5 Dendrimer+PIPZ Linker

G1 Dendrimer
+
PIPZ
→
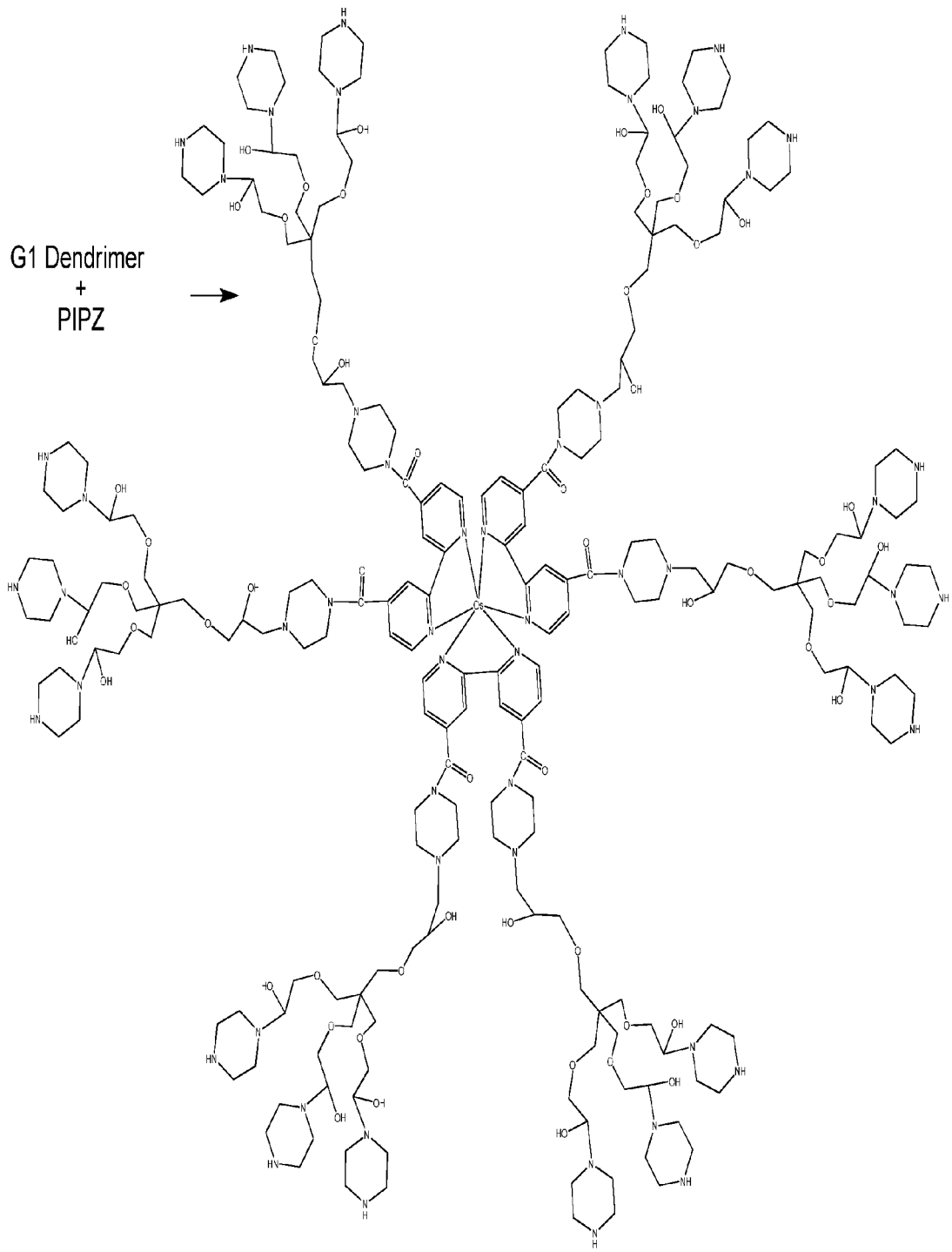

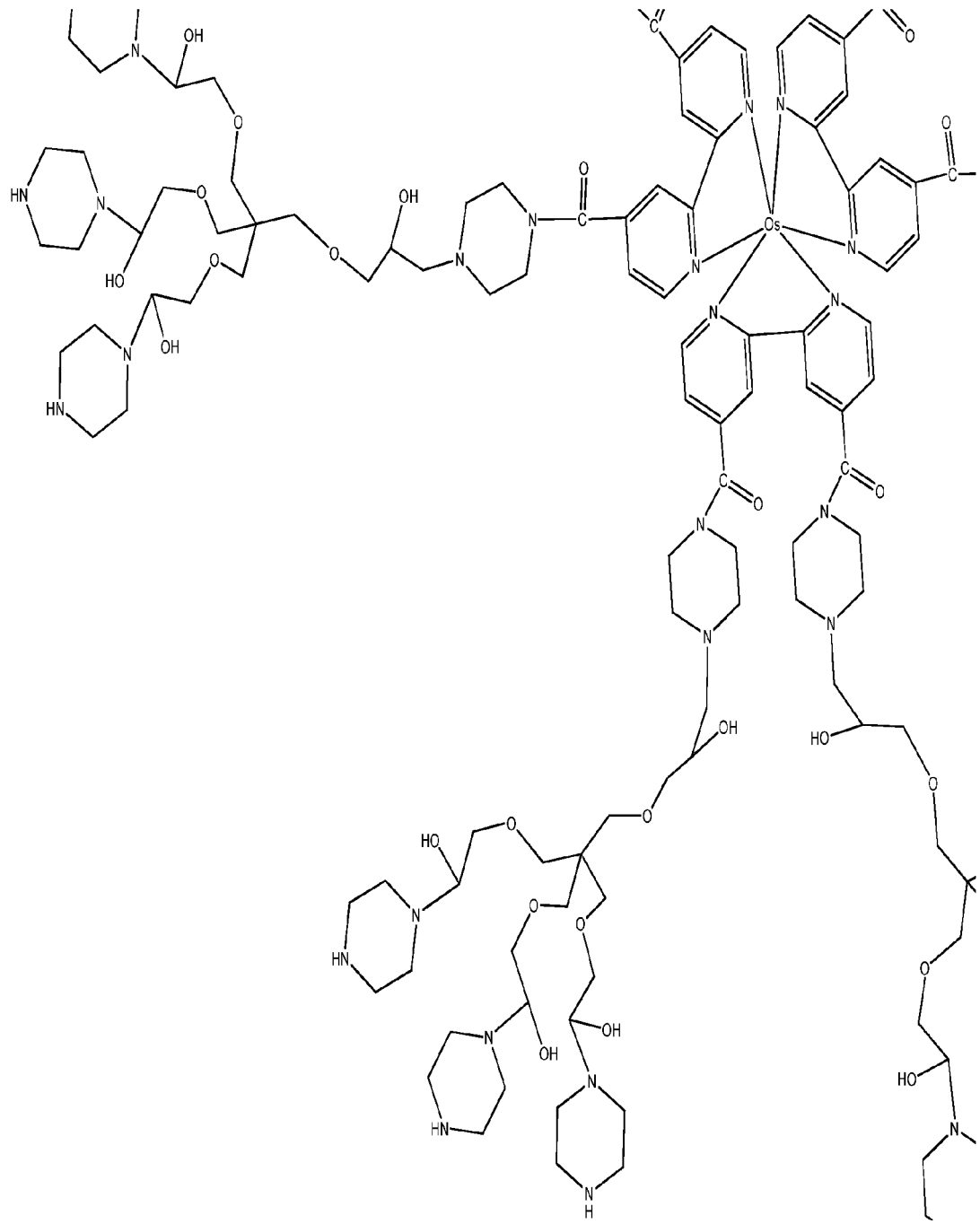

The above chemical structure illustrates one arm of a dendrimer molecule as enlarged from the immediately preceding dendrimer chemical structure as attached the core.

a) Ethyl N-piperazinecarboxylate (0.44 g, 2.78 mmol) and Cathode G1 Dendrimer (0.54 g) (from Example 11, Part B) is added a 50 mL round-bottomed flask, followed by 20 mL of methanol. The reaction is carried out at 55° C. for 8 hours, then solvent is removed by rotary evaporator.

b) A 10 mL of potasium hydroxide solution (0.30 g of KOH dissolved in 10 mL $H_2O$) and 10 mL of methanol are added to flask, and then refluxed for 24 hours. The pH of reaction crude is adjusted to 8 by HCl, and then dried by rotary evaporator. A 15 mL of methanol is added to dissolve product, and insoluble materials are removed by filtration. The filtrate is dripped into 400 mL diethyl ether to crystallize Cathode G1.5 Dendrimer+PIPZ.

Part D: Synthesis of Cathode G2 Dendrimer

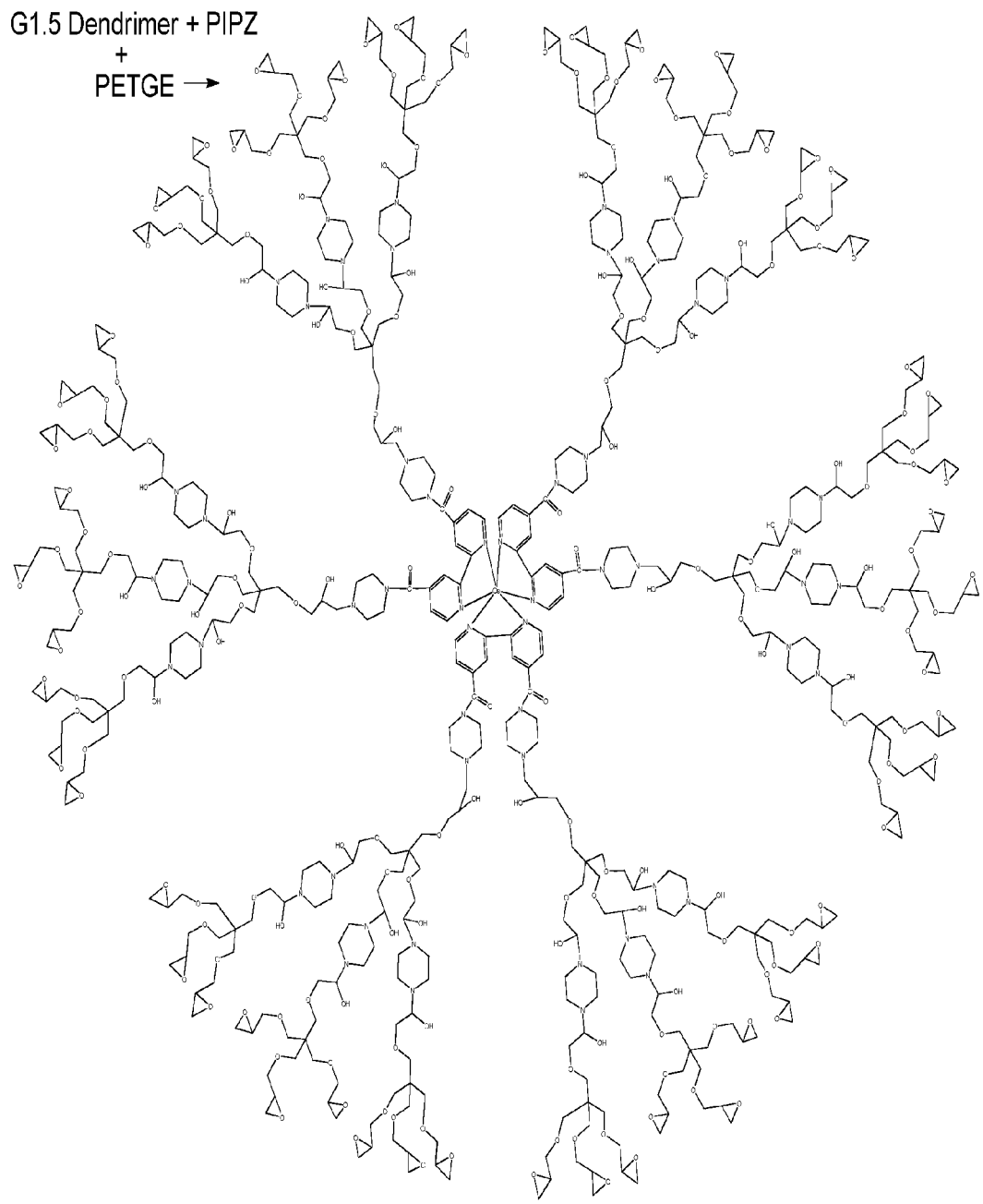
G1.5 Dendrimer + PIPZ + PETGE →

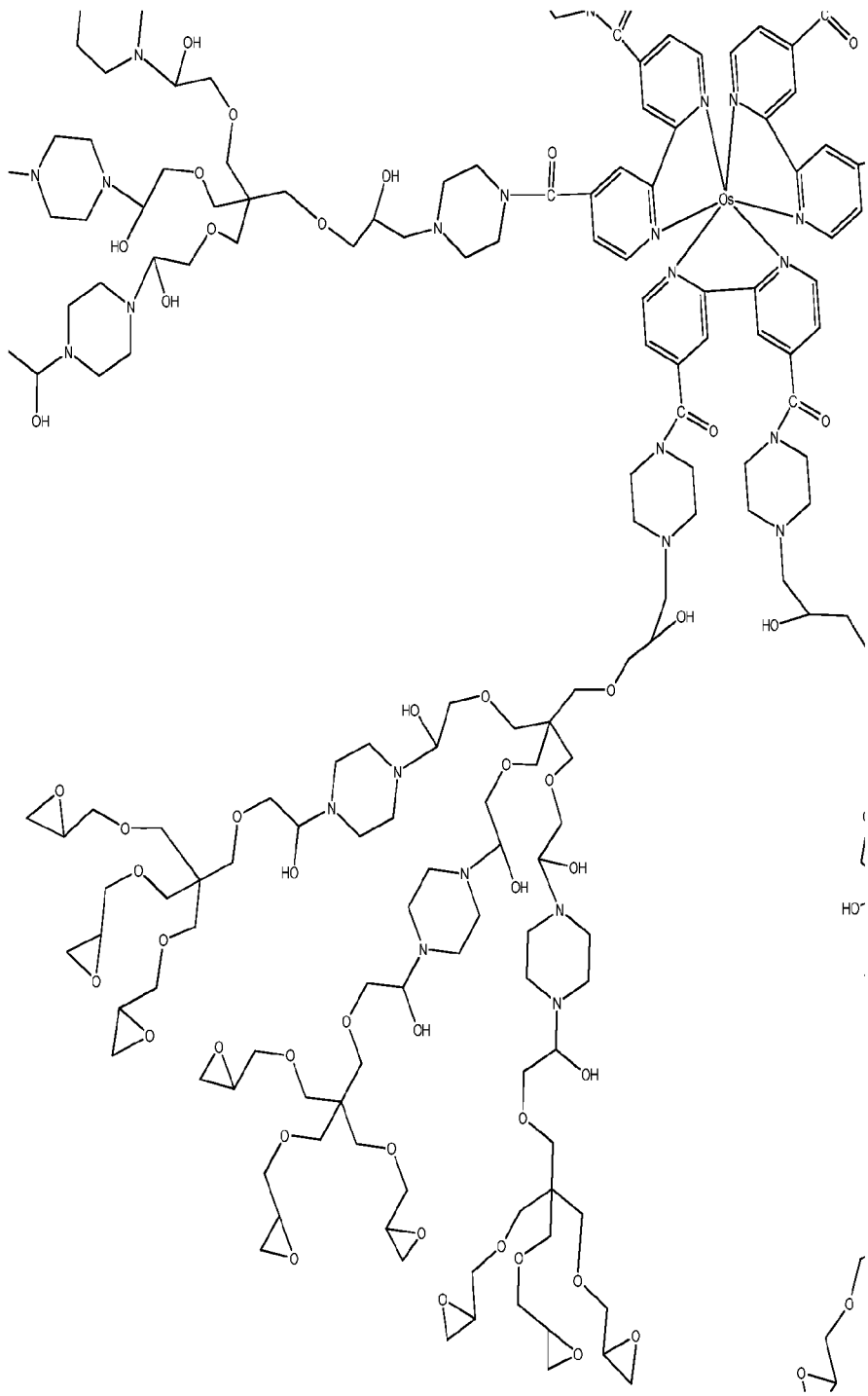

The above chemical structure illustrates one arm of a dendrimer molecule as enlarged from the immediately preceding dendrimer chemical structure as attached the core.

To a round bottom flask, Cathode G1.5 Dendrimer-PIPZ (0.57 g, 0.53 mmol) (made from Example 11, Part C) and PETGE (1.0 g, 2.8 mmol) is added to a 50 mL round-bottomed flask, followed by 30 mL of methanol. The reaction is carried out at room temperature for 6 hours. When the reaction is finished, the crude is dripped into 400 mL diethyl ether to crystallize Cathode Complex G2 Dendrimer.

Part E: Synthesis of Cathode G2 Dendrimer+DEIDA Surface

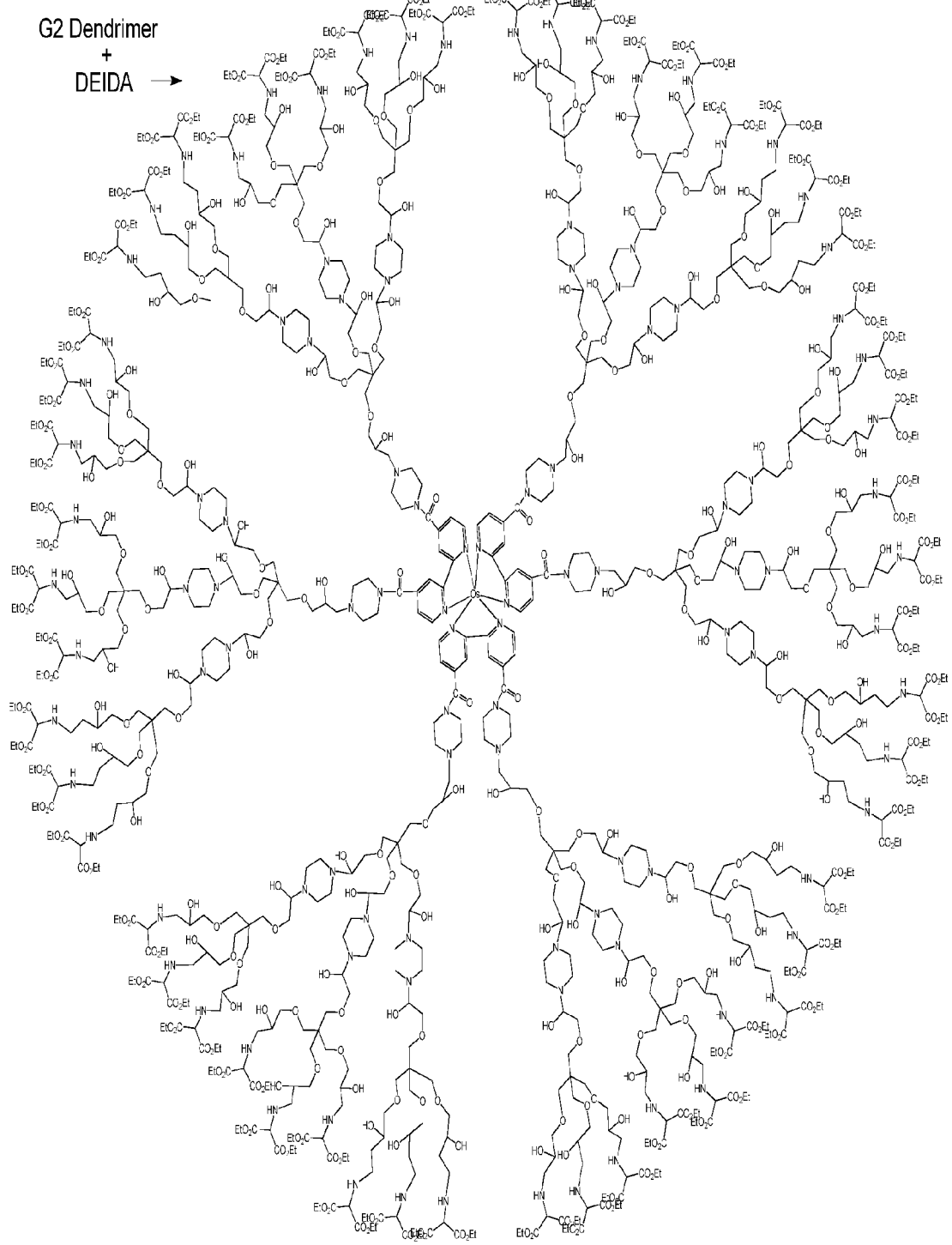

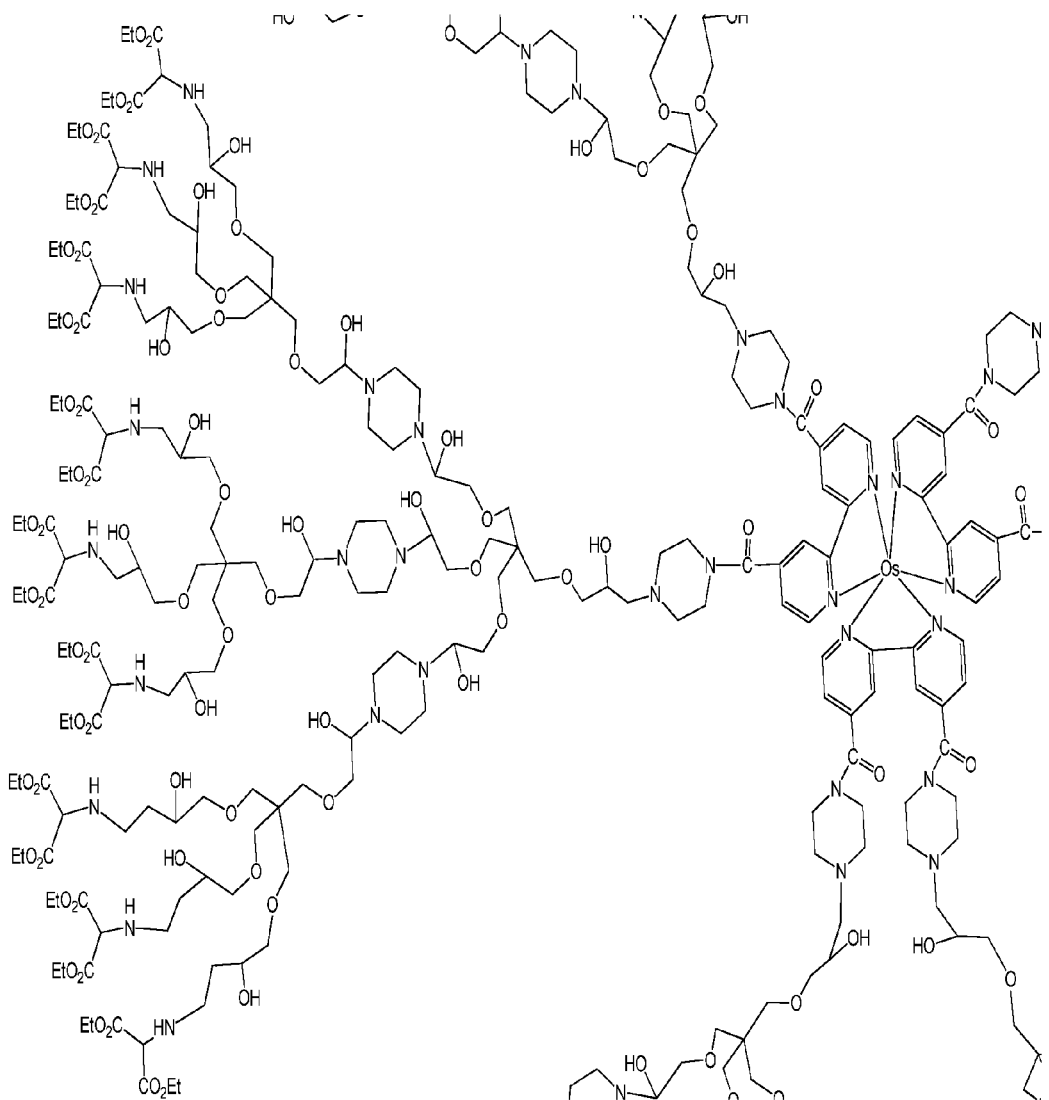

The above chemical structure illustrates one dendron of a dendrimer molecule as enlarged from the immediately preceding dendrimer chemical structure as attached the core.

In a round bottom flask, Cathode G2 Dendrimer (2 mmol, made from Example 11, Part D), is added to a solution of Tris (7.5 mmol) (Aldrich) in MeOH. It is heated at 60° C. for 24 hours.

Example 12

Synthesis of Anode Polymeric Power Cells Aggregate Network

Part A: Synthesis of Anode G2 Dendrimer Made by example 10, Part D

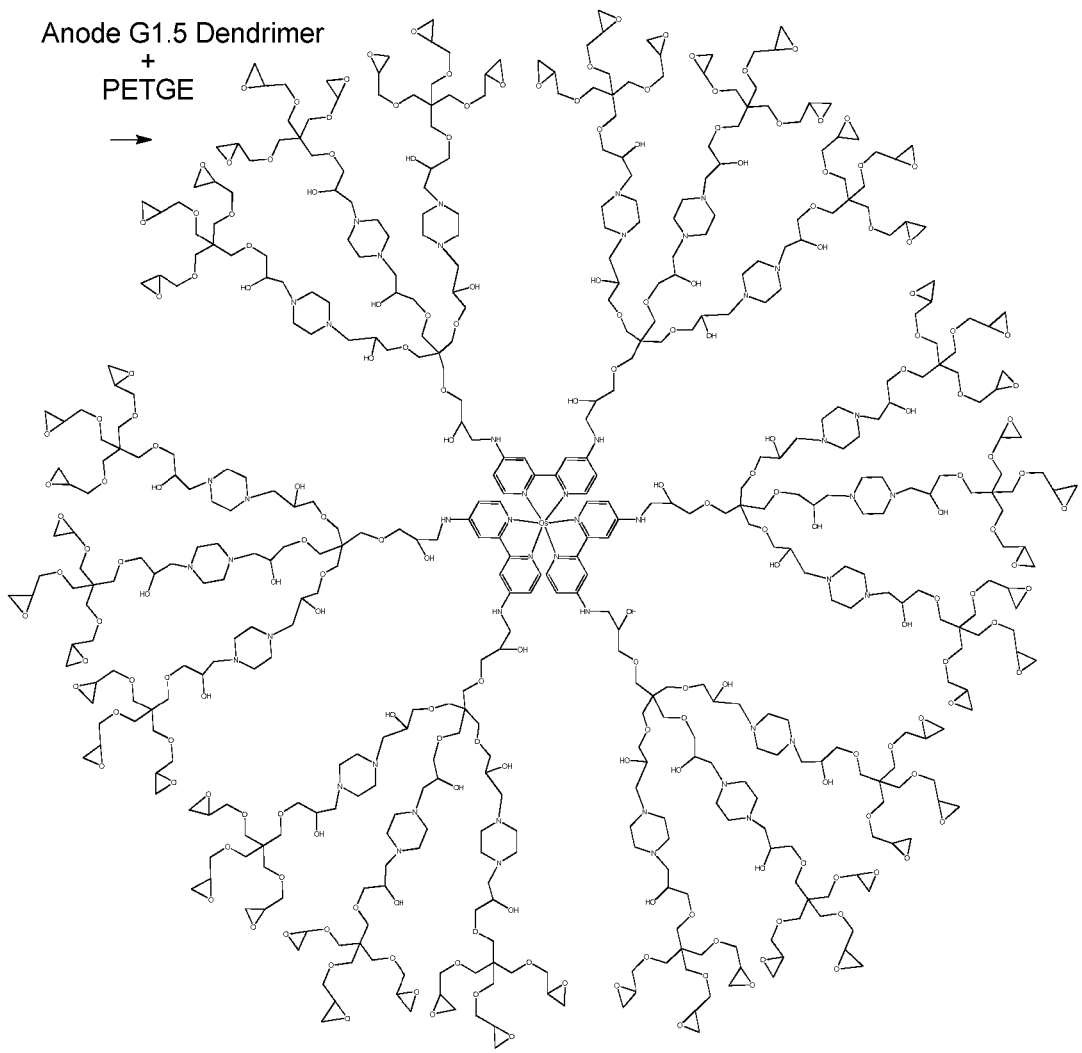

137    138
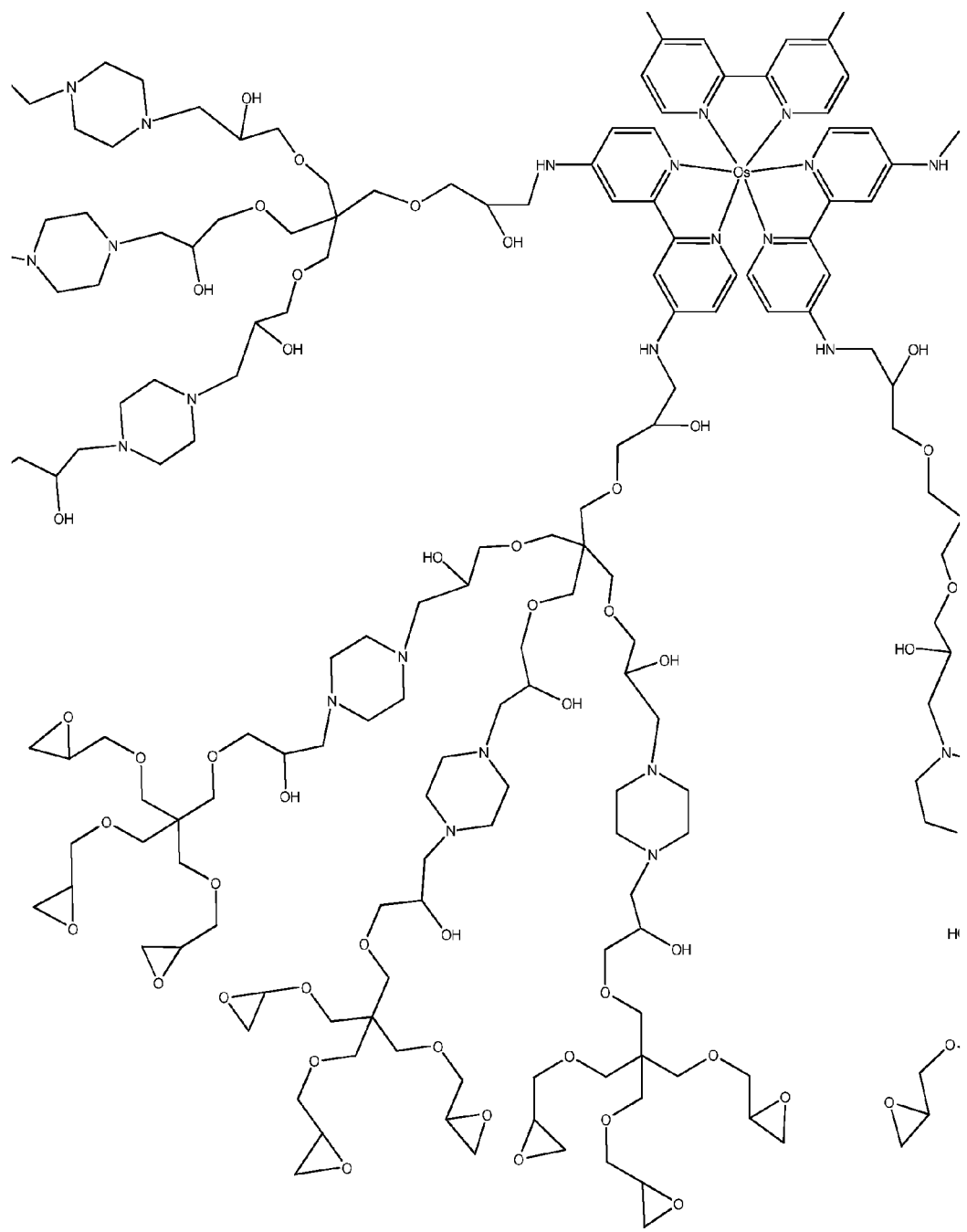

The above chemical structure illustrates two dendrons of a dendrimer molecule as enlarged from the immediately preceding dendrimer chemical structure as attached the core.

Prepare according to procedure in Example 10, Part D

Part B: Synthesis of G2 Dendrimer Network

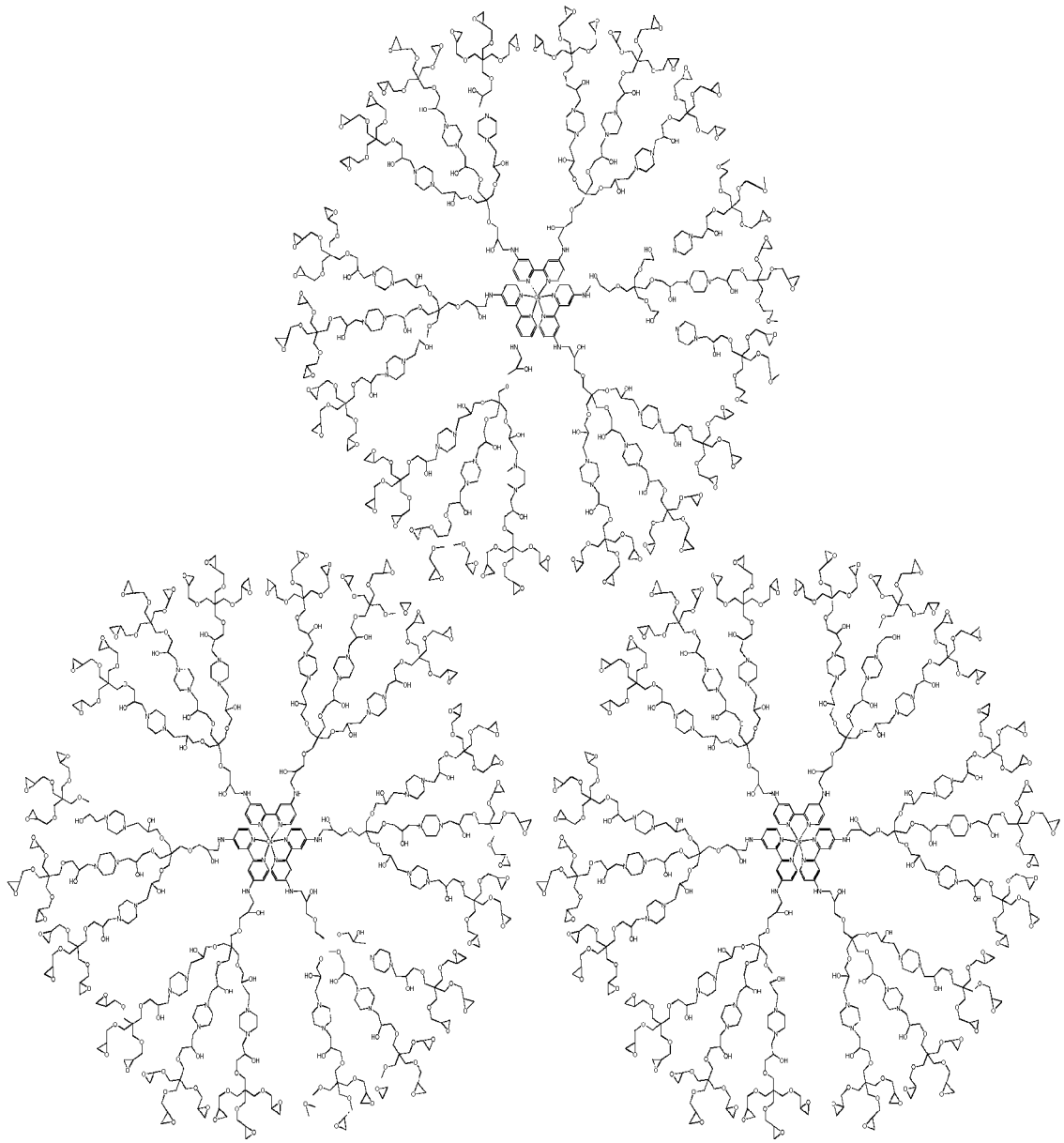

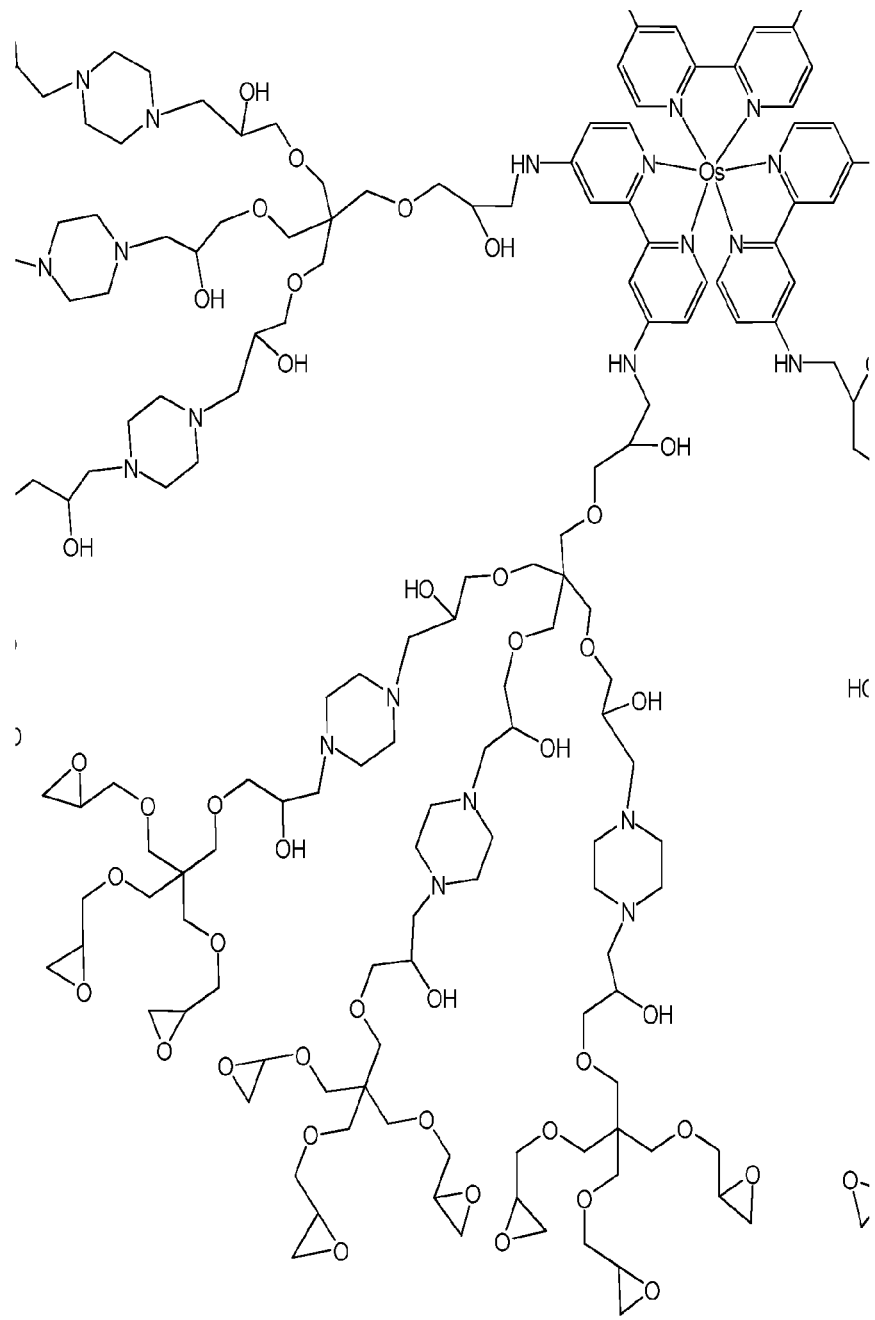

The above chemical structure illustrates two dendron arms of one of the dendrimer molecules as attached to the core and as enlarged from the immediately preceding dendrimer chemical structure.

30 mg Anode G2 Dendrimer (from Example 10, Part D) is added to 1.5 mL 10% HEPES solution.

Figure 21:
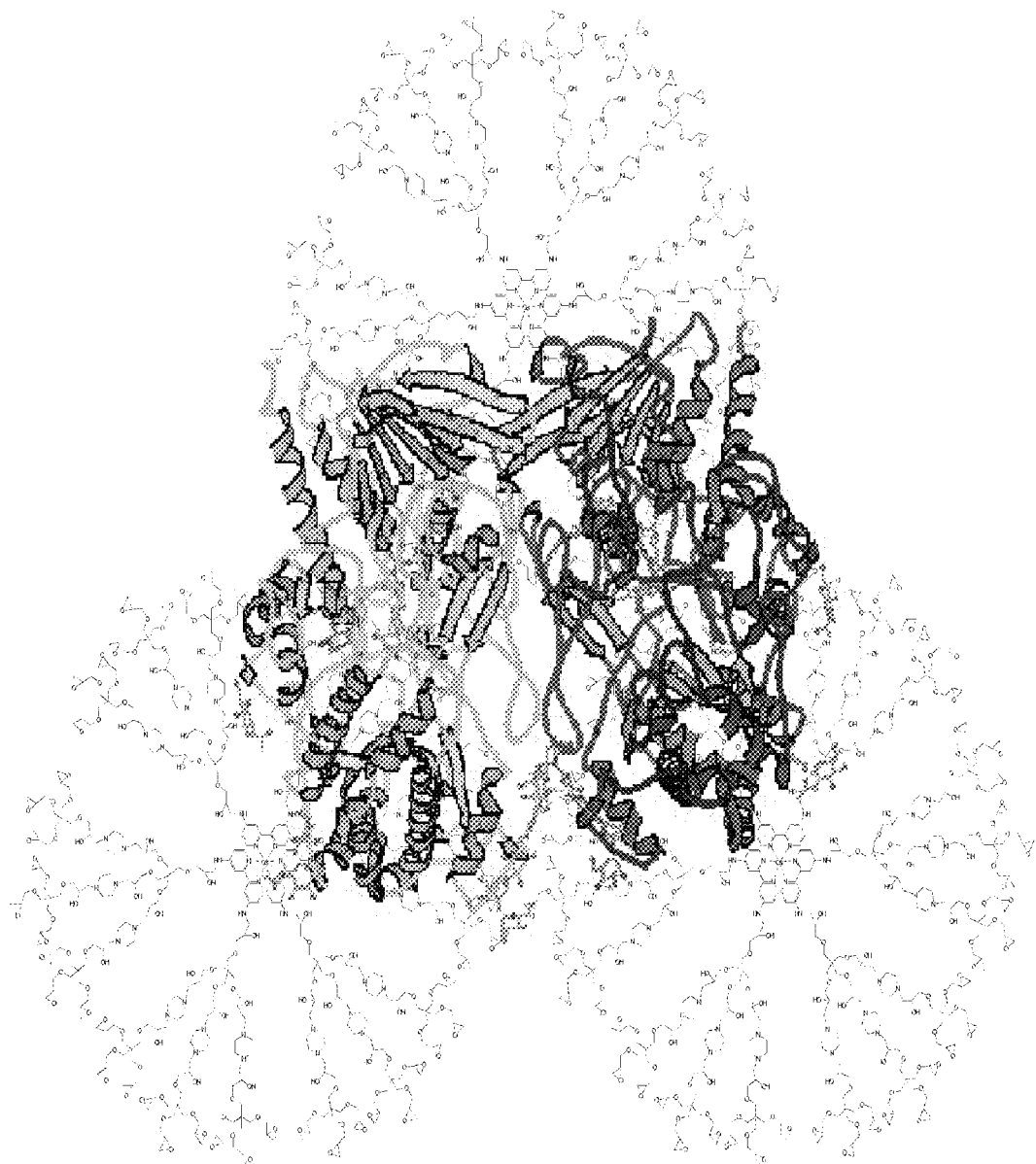
FIG. 21 is a depiction of the chemical structure of a G2 dendrimer network+enzyme (color portion) of Example 12, Part C.

Part C: Synthesis of G2 Dendrimer Network Plus Enzyme; the chemical structure is depicted in FIG. 21.

10 mg of Glucose oxidase is added to 1.5 mL 10% HEPES solution. Anode G2 Dendrimer solution prepared above (from Example 12, Part B) is added to the glucose oxidase solution. The complex is stored at room temperature for seven days before use. Different ratios of Anode G2 Dendrimer and glucose oxidase are possible by adjusting concentrations.

Example 13

Synthesis of Dimer Power Cells

Part A: Synthesis of Bridging Group

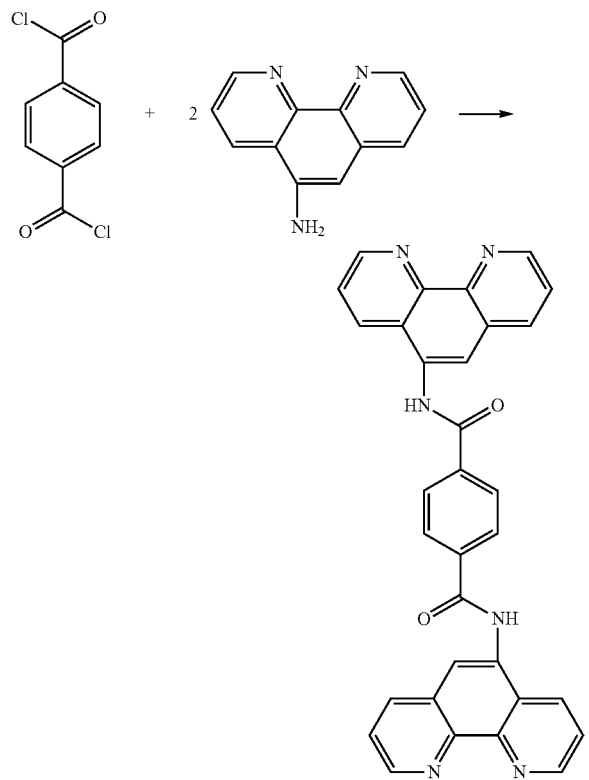

Terephthaloyl chloride (Sigma-Aldrich) (0.31 g, 1.53 mmol) was dissolved in 10 mL of DMSO anhydrous, and then it was dripped into 5-amino-1,10-phenanthroline solution made up by 5-amino-1,10-phenanthroline (Polysciences) (0.60 g, 3.08 mmol) and triethylamine (0.466 g, 4.61 mmol) dissolved in 15 mL of DMSO anhydrous at 0° C. The reaction was allowed to warm to room temperature slowly and then refluxed for 1 hour to finish the reaction. The crude was washed by water (5×20 mL), dried over $Na_2SO_4$ and then yield the product under reduced pressure and high temperature. (product: 0.76 g, yield: 96% before further purification).

Part B: Synthesis of Anode Transition Metal Complex-2

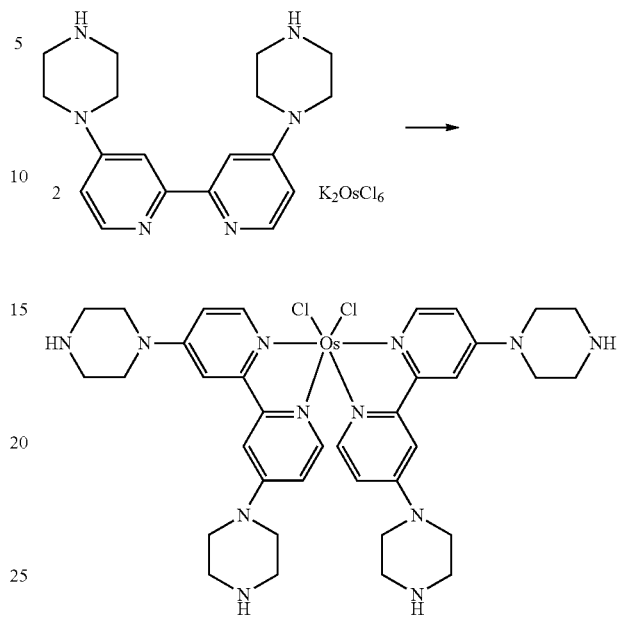

4,4'-Dipiperazine-2,2'-bipyridine (1.16 g, 4.36 mmol) (from Example C) is dissolved in 7 mL ethylene glycol and 25 mL DMF, followed by $K_2OsCl_6$ (1.0 g, 2.08 mmol). The reaction mixture is refluxed for 1 hour. It is then cooled to RT and transferred to a 500 mL beaker. $Na_2S_2O_4$ solution (7.2 g $Na_2SO_4$ in 150 mL water) is dripped to reaction mixture over a period of a half hour. The reaction mixture in the beaker is cooled in an ice bath for 1.5 hours. The solid product is collected by vacuum filtration and washed with deionized water (3×20 mL), refrigerated methanol (10 mL), and diethyl ether (120 mL) respectively. It is dried in a vacuum oven at 60° C. for 24 hours.

Part C: Synthesis of Dimer Complex a) Synthesis of Dimer Complex-Anode Complex Addition

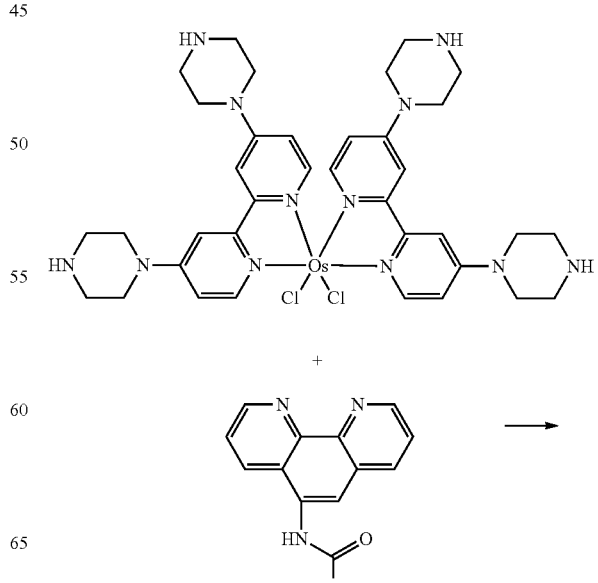

-continued

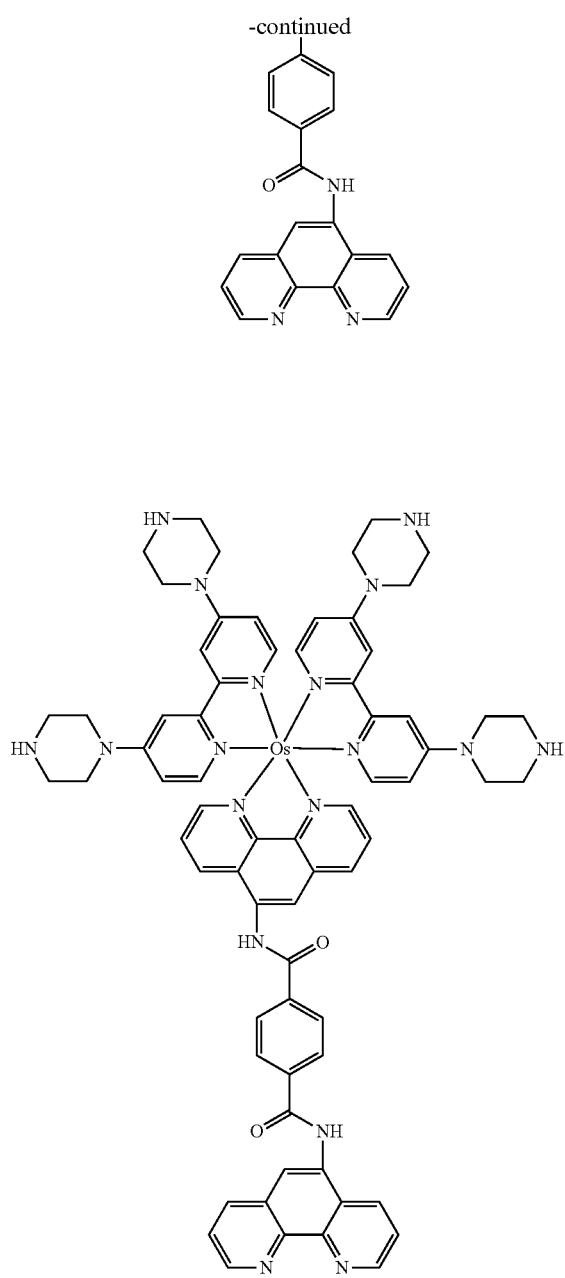

b) Synthesis of Dimer Complex-Cathode Complex Addition

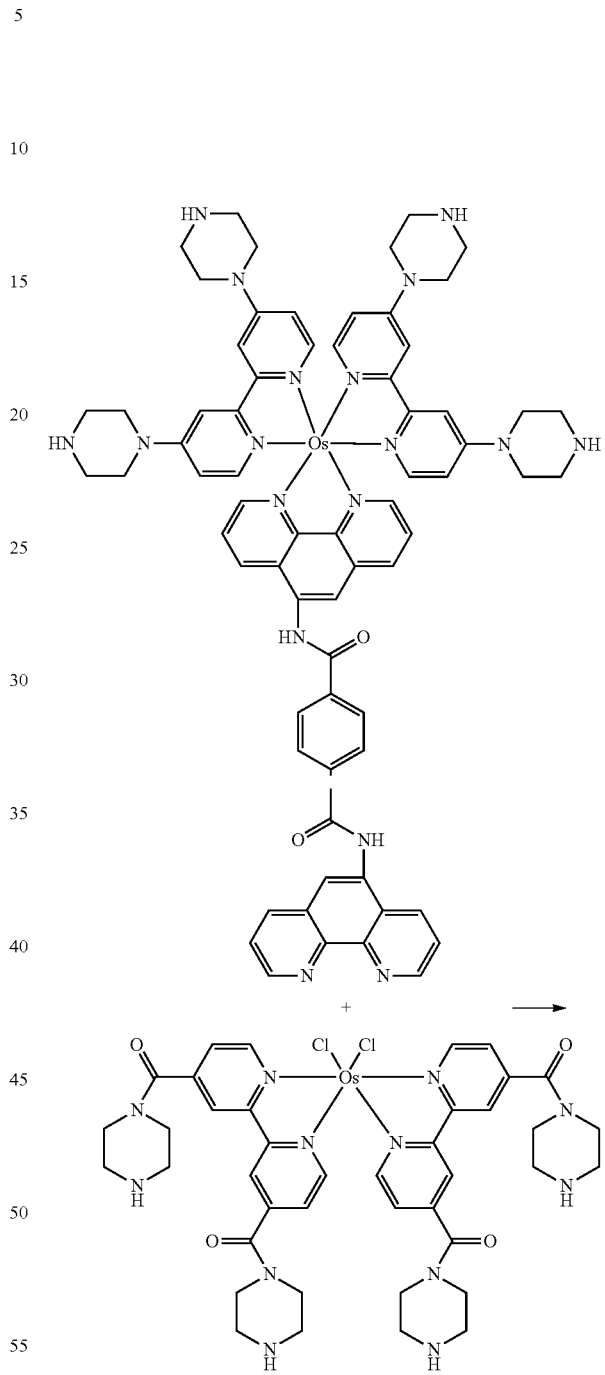

0.91 mg (1.0 mmol) Anode Transition Metal Complex-2 (from Example 13, Part B) is dissolved in 35 mL of ethylene glycol, followed by 0.52 mg (1.0 mmol) bridging complex (from Example 13, Part A). The reaction mixture is refluxed for 120 hours at 190-200° C. It is then cooled to RT and transferred to a 500 mL beaker. The black powder, Dimer Complex-Anode Complex, was collected and dried in a vacuum oven at 60° C. for 24 hours.

149
-continued

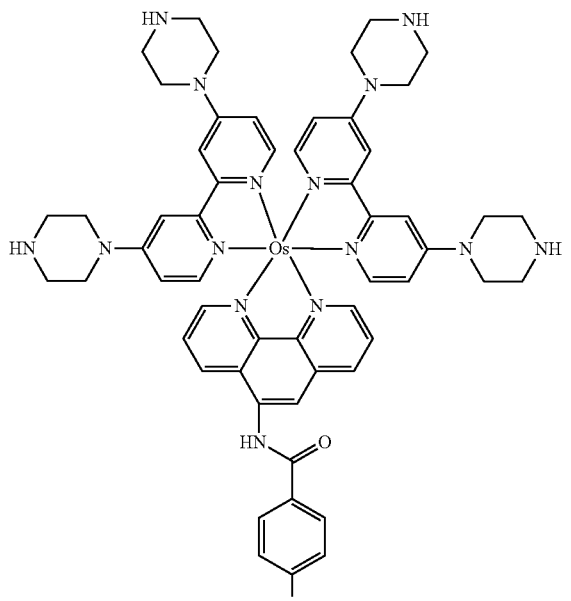

150
-continued

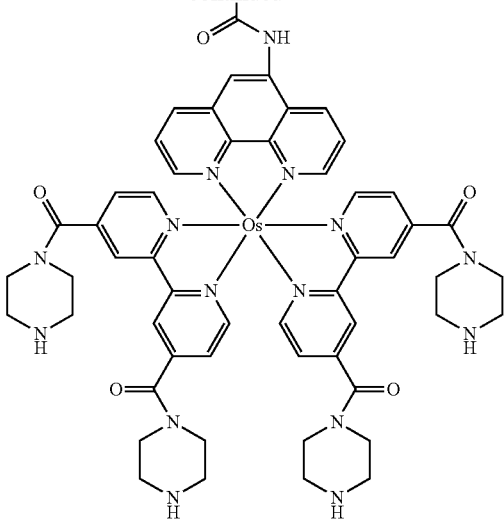

1.36 g (1.0 mmol) Dimer Complex-Anode Complex (from above) is dissolved in 35 mL of ethylene glycol, followed by 1.02 g (1.0 mmol) Cathode Complex (from Example 3). The reaction mixture is refluxed for 120 hours at 190-200° C. It is then cooled to RT and transferred to a 500 mL beaker. The black powder, Dimer Complex (Anode-Cathode), was collected and dried in a vacuum oven at 60° C. for 24 hours.

Part D: Synthesis of Dimer G1 Dendrimer

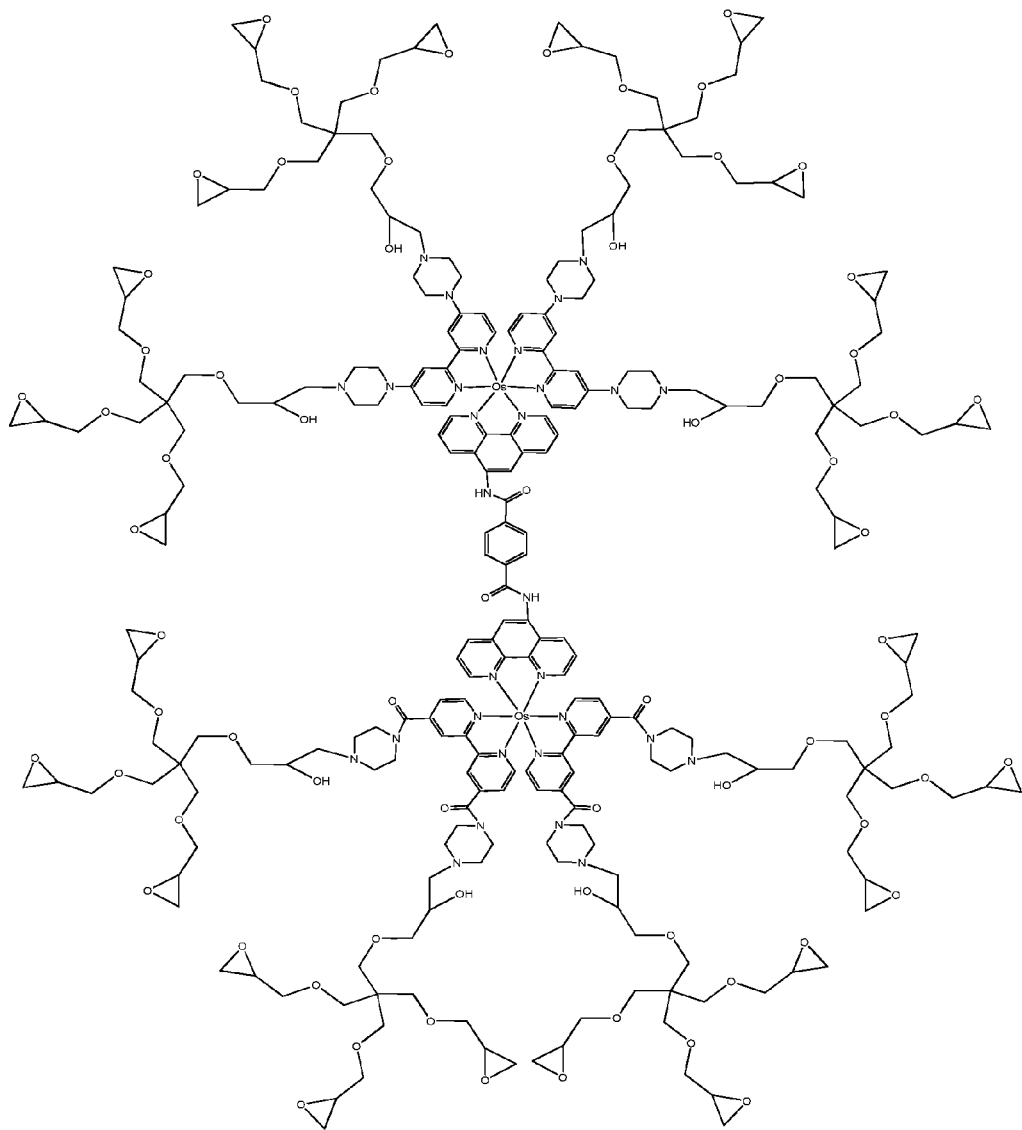

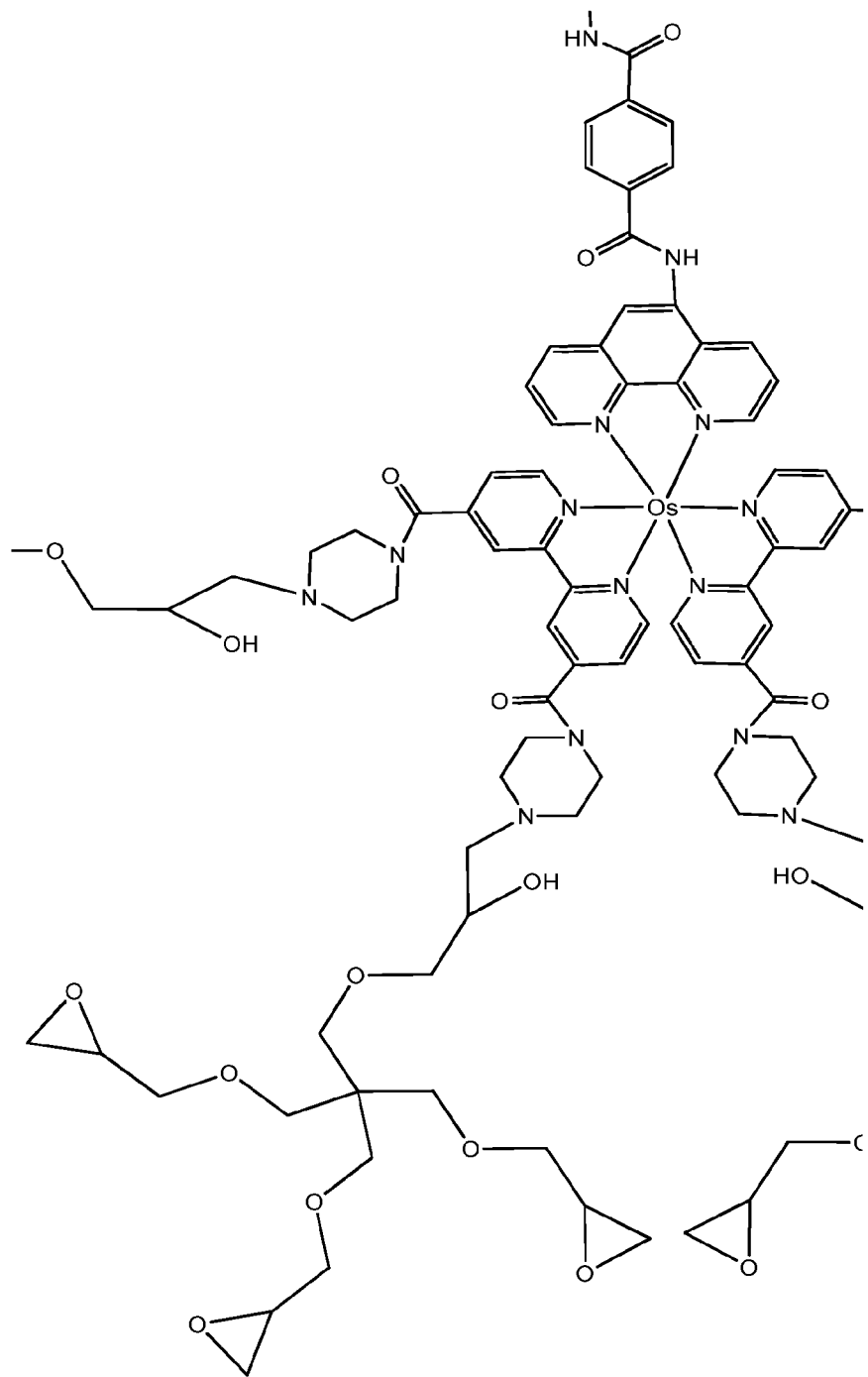

The above chemical structure illustrates one arm of the dimer dendrimer molecule as attached to the core and as enlarged from the immediately preceding dimer dendrimer chemical structure.

Dimer Complex (Anode-Cathode), (0.76 g, 0.33 mmol) (made from Example 13, Part C) and PETGE (2.8 g, 7.89 mmol) is added to a 50 mL round-bottomed flask, followed by 30 mL of methanol. The reaction is carried out at room temperature for 6 hours. When the reaction is finished, the crude is dripped into 400 mL diethyl ether to crystallize Dimer G1 Dendrimer.

Part E: Synthesis of Dimer G1.5 Dendrimer PIPZ

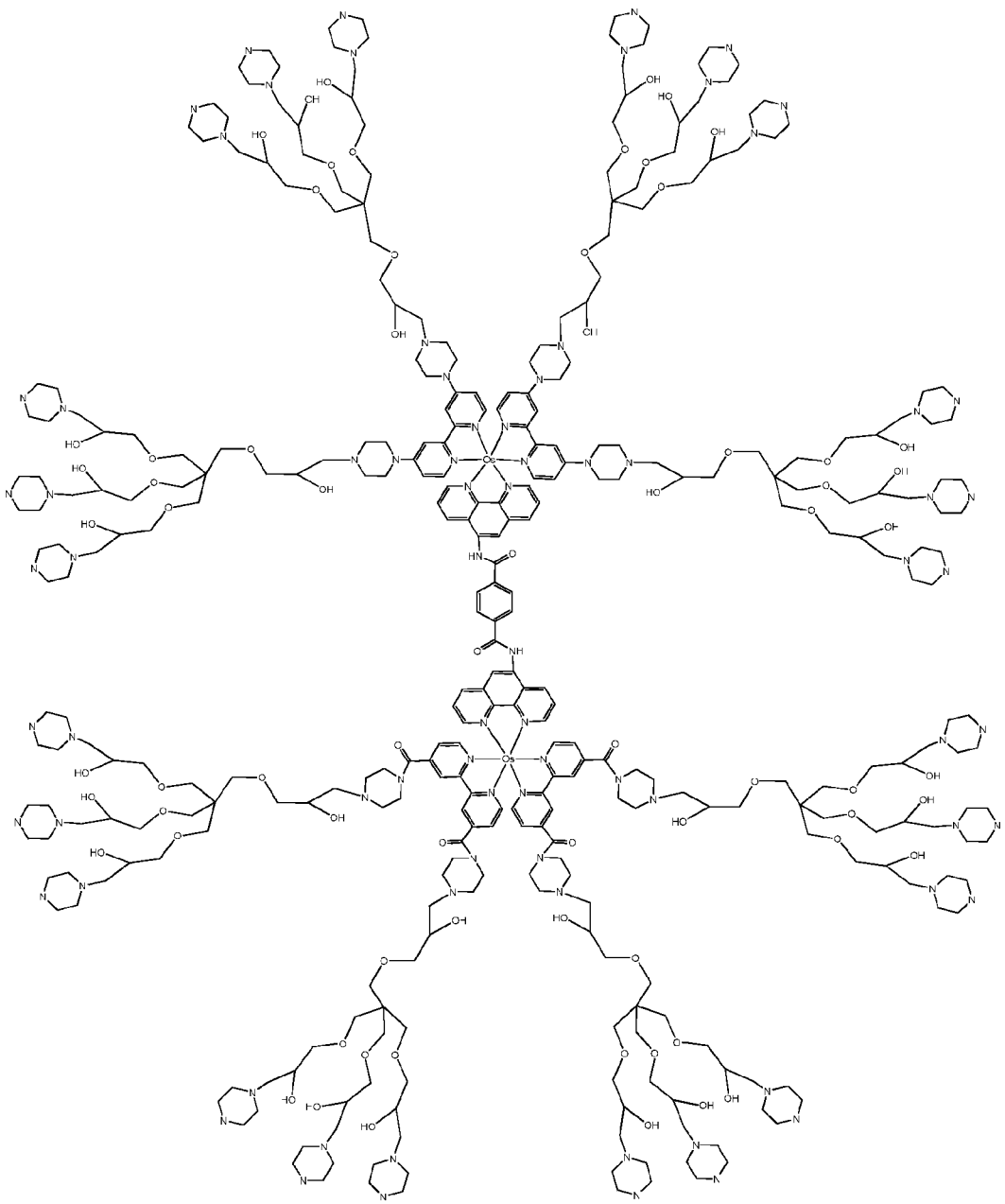

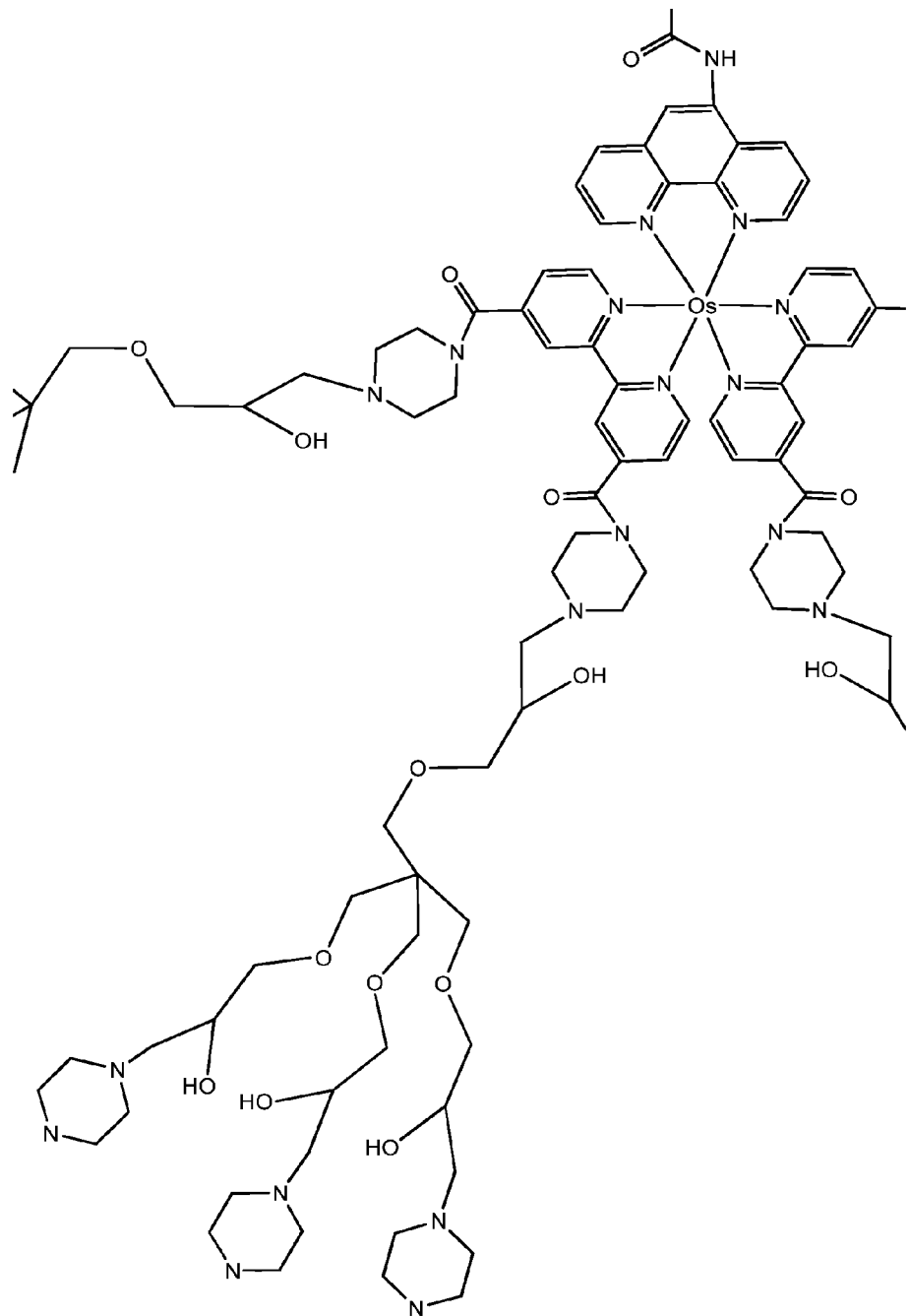

The above chemical structure illustrates one arm of the dimer dendrimer molecule as attached to the core and as enlarged from the immediately preceding dimer dendrimer chemical structure.

a) Ethyl N-piperazinecarboxylate (0.52 g, 3.29 mmol) and Dimer G1 Dendrimer (0.48 g) (from Example 13, Part D) is added a 50 mL round-bottomed flask, followed by 20 mL of methanol. The reaction is carried out at 55° C. for 8 hours, then solvent is removed by rotary evaporator.

b) A 10 mL of potasium hydroxide solution (0.40 g of KOH dissolved in 10 mL $H_2O$) and 10 mL of methanol are added to flask, and then refluxed for 24 hours. The pH of reaction crude is adjusted to 8 by HCl, and then dried by rotary evaporator. A 15 mL of methanol is added to dissolve product, and insoluble materials are removed by filtration. The filtrate is dripped into 400 mL diethyl ether to crystallize Dimer G1.5 Dendrimer PIPZ.

Part F: Synthesis of Dimer G2 Dendrimer

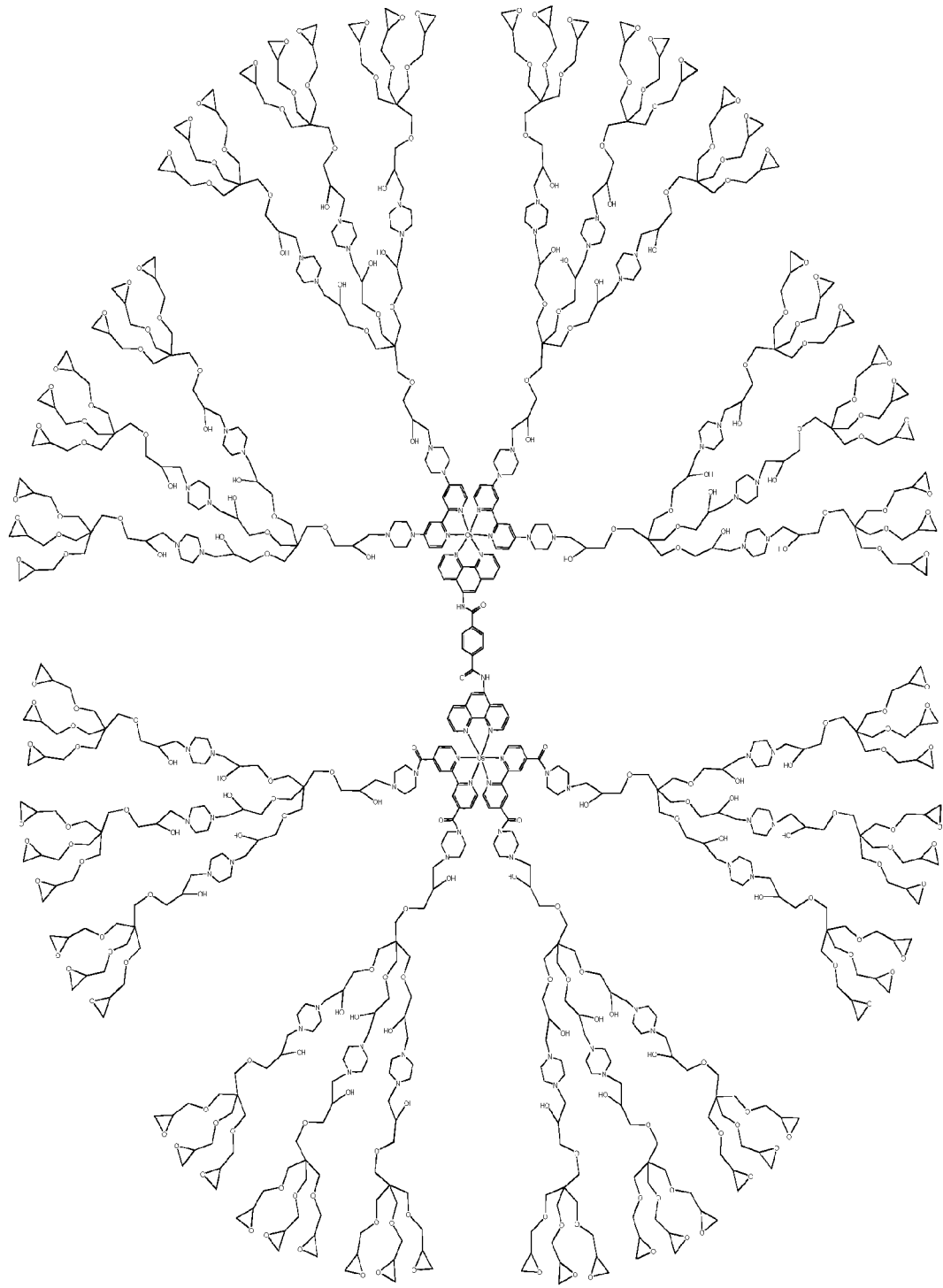

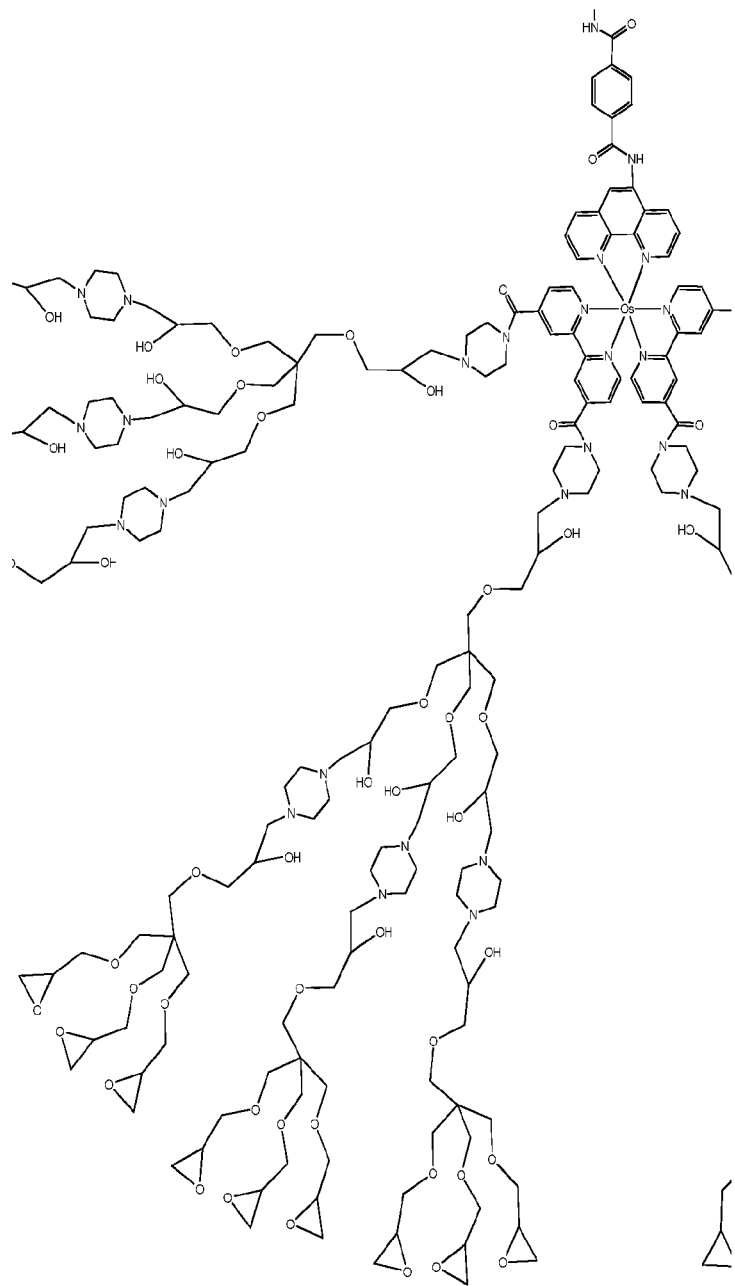

The above chemical structure illustrates one arm of the dimer dendrimer molecule as attached to the core and as enlarged from the immediately preceding dimer dendrimer chemical structure.

Dimer G1.5 Dendrimer PIPZ (0.76 g, 0.33 mmol) (made from Example 13, Part C) and PETGE (2.8 g, 7.89 mmol) is added to a 50 mL round-bottomed flask, followed by 30 mL of methanol. The reaction is carried out at room temperature for 6 hours. When the reaction is finished, the crude is dripped into 400 mL diethyl ether to crystallize Dimer G2 Dendrimer.

Part G: Synthesis of Dimer G2 Dendrimer+Tris [SF]

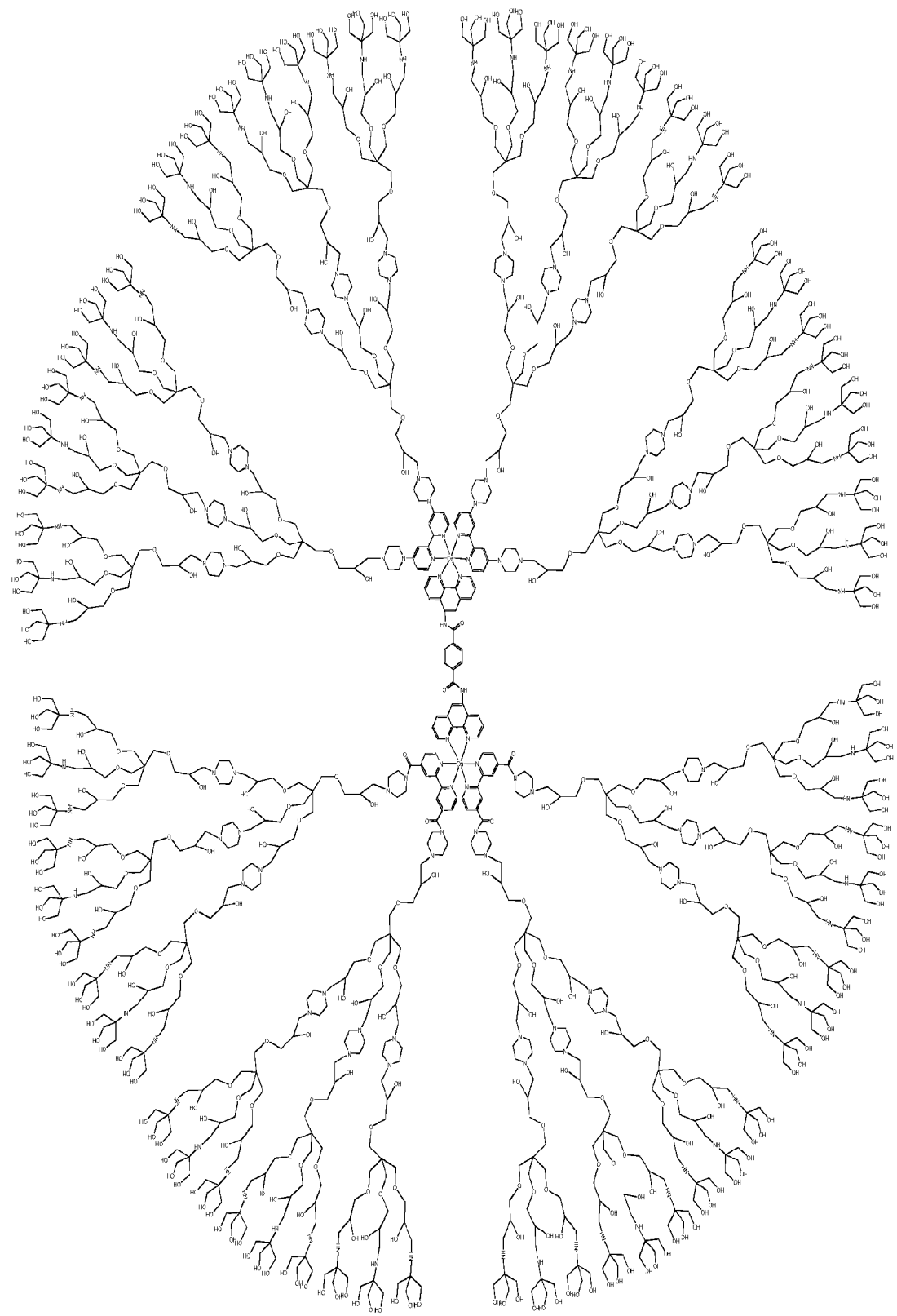

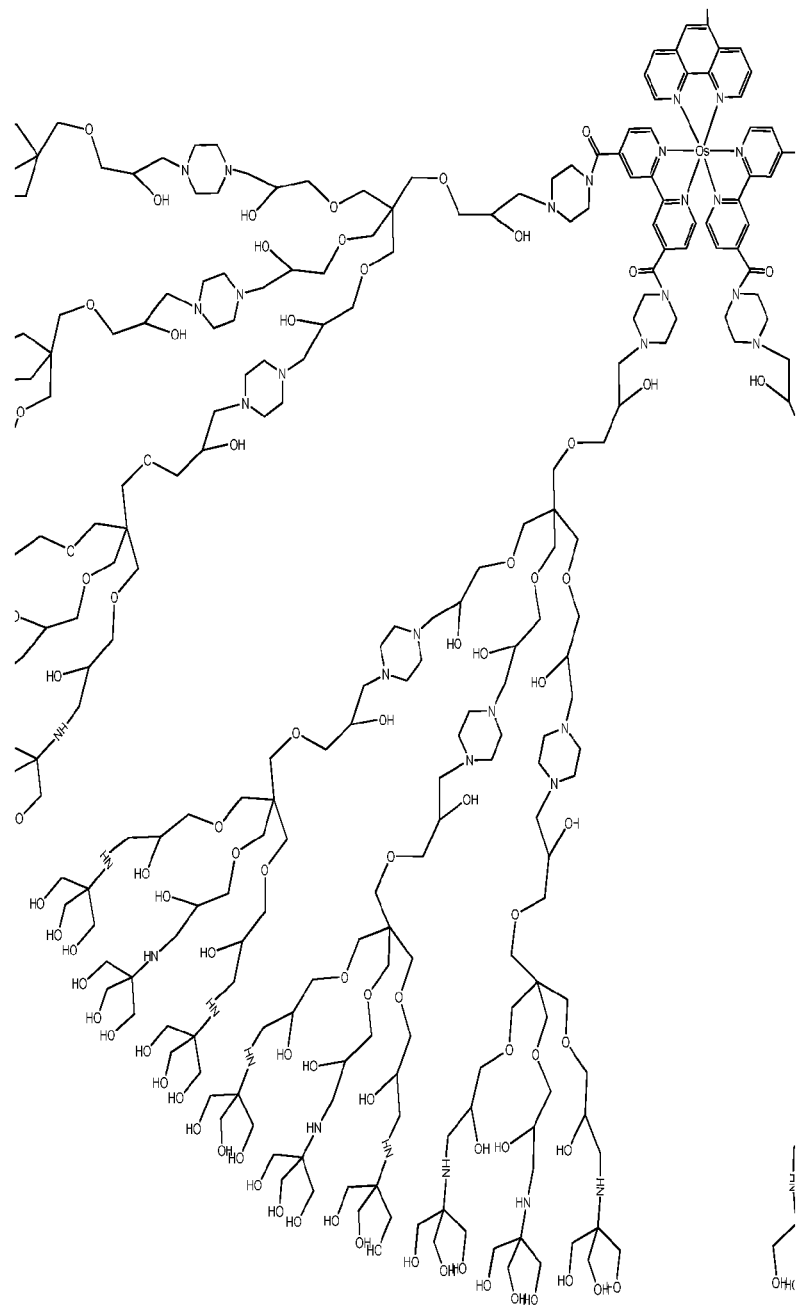

The above chemical structure illustrates one arm of the dimer dendrimer molecule as attached to the core and as enlarged from the immediately preceding dimer dendrimer chemical structure.

In a round bottom flask, Dimer Complex G2 Dendrimer (2 mmol, made from Example 13, Part E), is added to a solution of Tris (7.5 mmol) (Aldrich) in MeOH. It is heated at 60° C. for 24 hours.

Carried Materials with BNPC

Example 14

Figure 22:
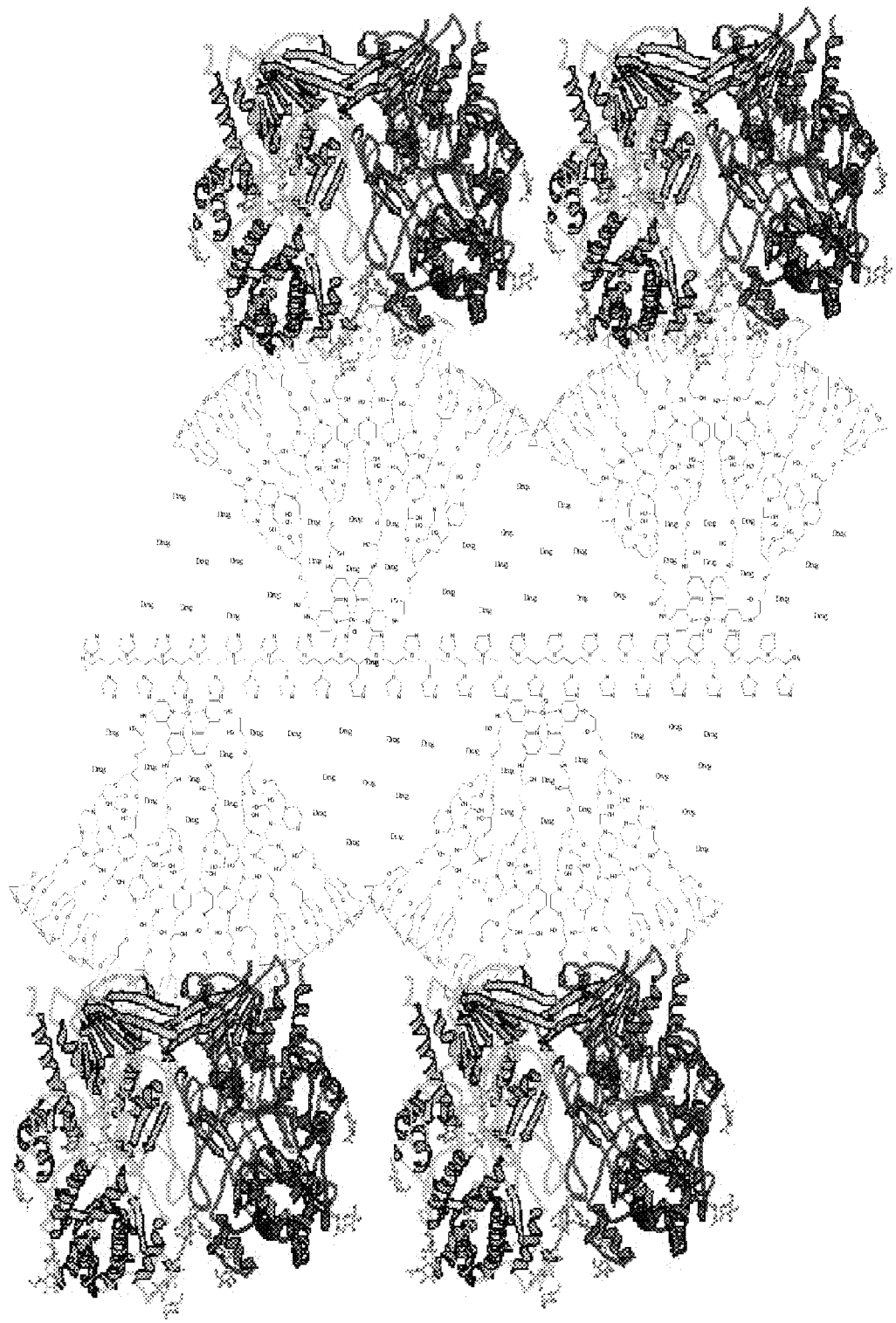
FIG. 22 is a depiction of the chemical structure of a drug (indomethacin) encapsulated by BNPC.

Drug Encapsulation by BNPC, Using the Non-Steroidal Anti-Inflammatory Drug (NSAID) Indomethacin as a Model Drug; [BNPC]-[CM]; See FIG. 22 for the Product Structure An excess (15 mg) of indomethacin was added to vials containing the aqueous BNPC (0.2% w/v) in 5.0 mL of DI water solutions. These suspensions were briefly exposed to ultrasonication, then incubated overnight at 37° C. and 100 rpm in a shaking water bath, and allowed to equilibrate at RT. The BNPC-indomethacin suspensions were filtered through a 0.2 nm, 13-mm in diameter nylon syringe filter to remove excess drug. By UV spectroscopy at 220 nm on UPLC from Waters, after 6 minutes, we found a new peak for the mixture of the BNPC-Indomethacin. The peak for Indomethacin by itself was at 4.8 minutes and peak for the dendrimer was at 5.02 minutes.

Example 15

Encapsulation of Copper(0) Atoms by BNPC a) Synthesis of Anode Polymer G2 Dendrimer+Copper$^{+2}$

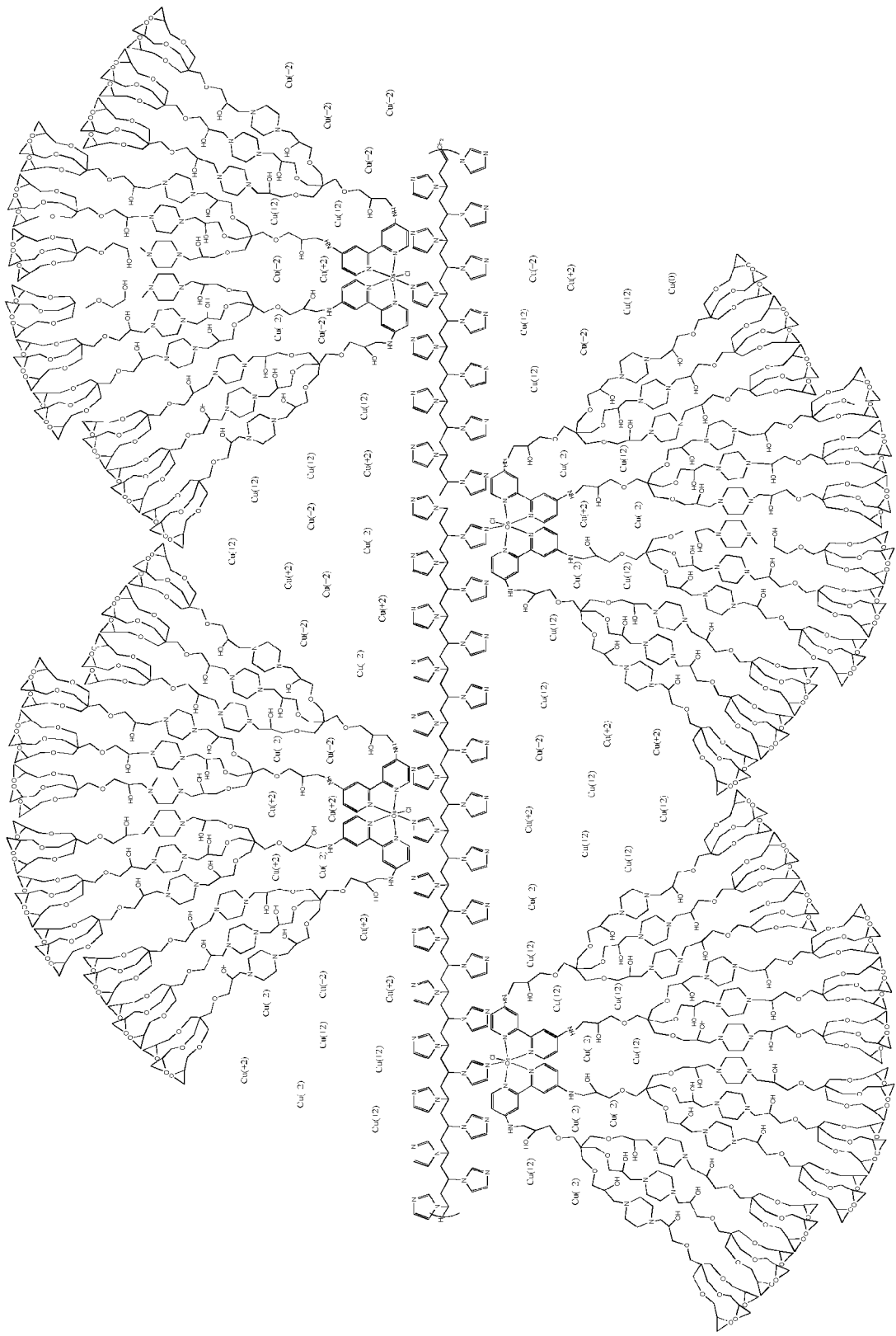

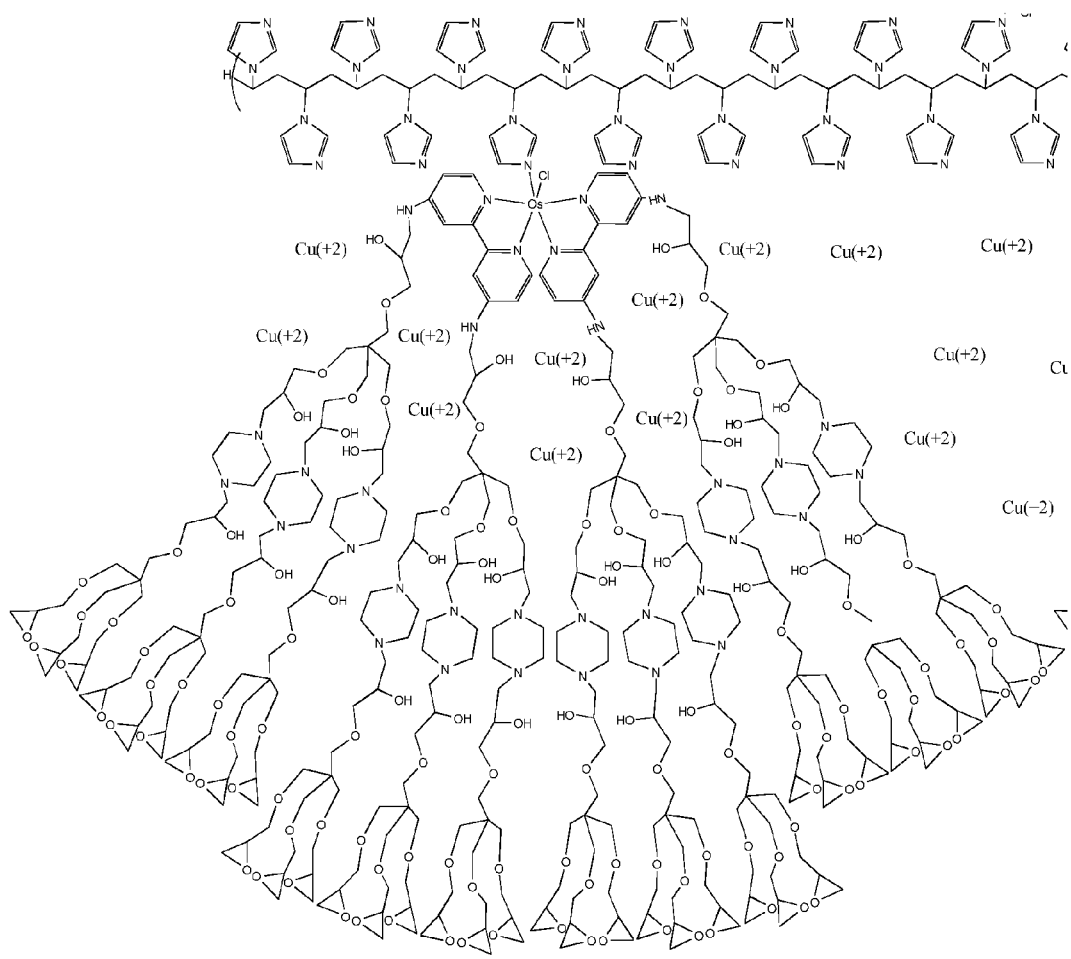

The above chemical structure illustrates one dendron molecule as attached to the core and as enlarged from the immediately preceding backbone structure.

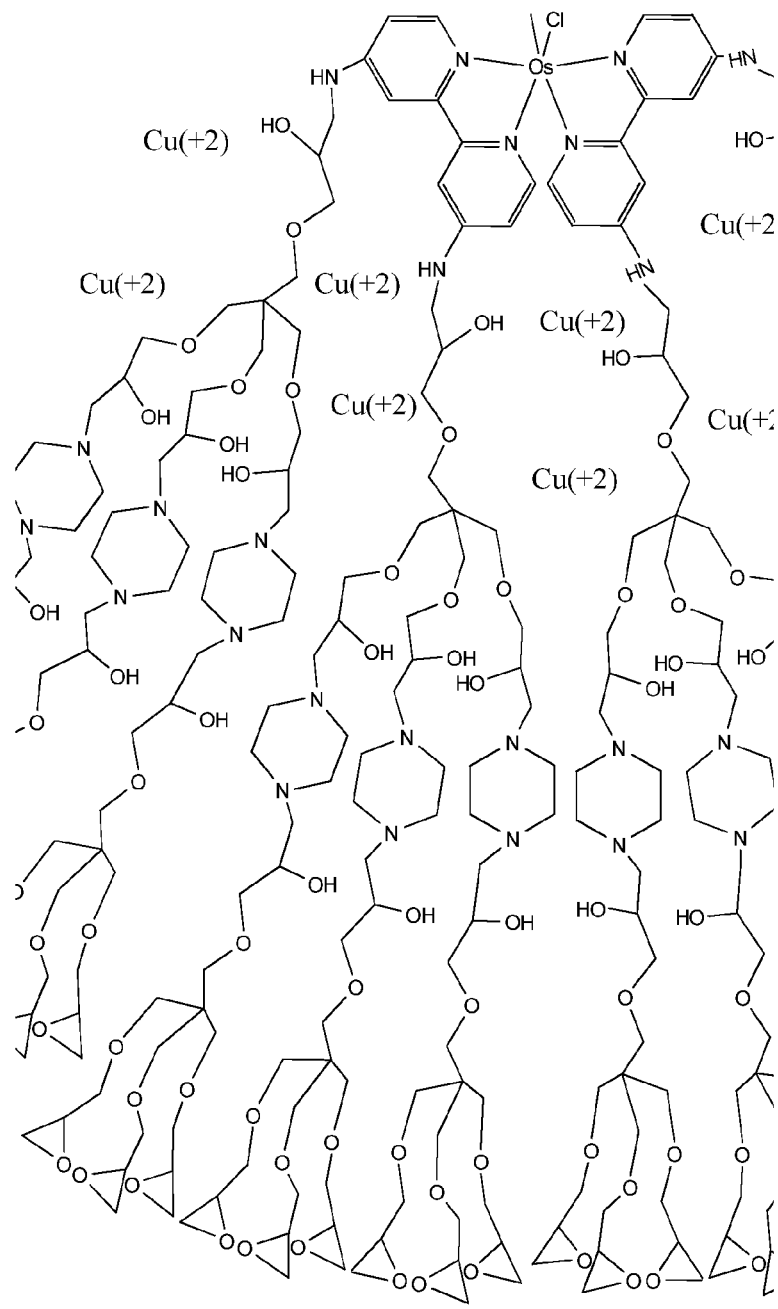

The above chemical structure illustrates one dendron arm of one of the dendron molecules as attached to the core and as enlarged from the immediately preceding dendron chemical structure.

In a round bottom flask, Anode Polymer G2 Dendrimer ((0.0038 mmol) made from Example 9, Part E) was dissolved in DI water as a BNPC stock solution. Copper(II) acetate (0.0734 mmol) was dissolved in DI water. The BNPC stock solution was then mixed with the copper(II) acetate solution. This mixture was stirred at RT for 20 mins to form the BNPC-copper(II) complex.

b) Synthesis of Anode Polymer G2 Dendrimer+Copper (0)

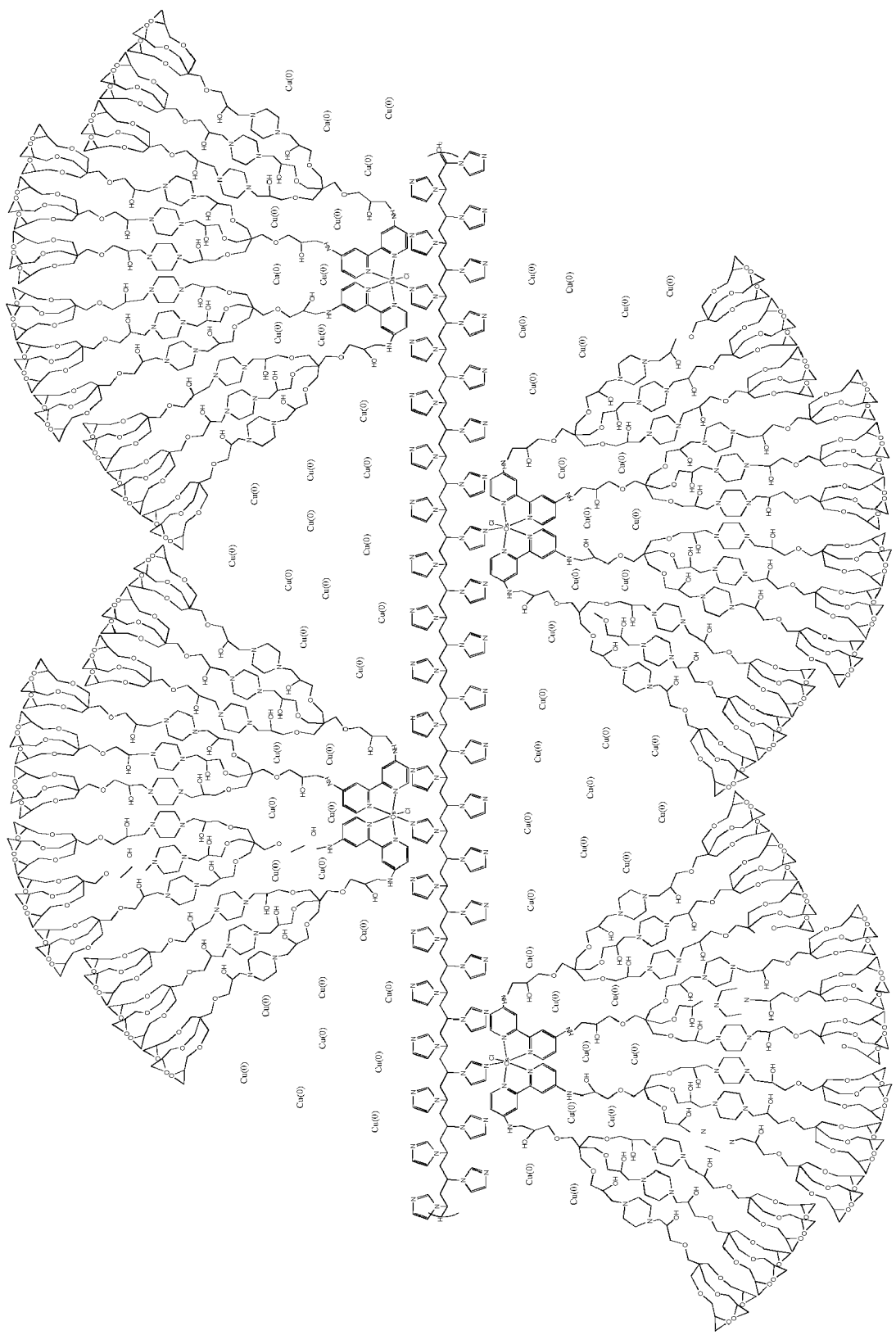

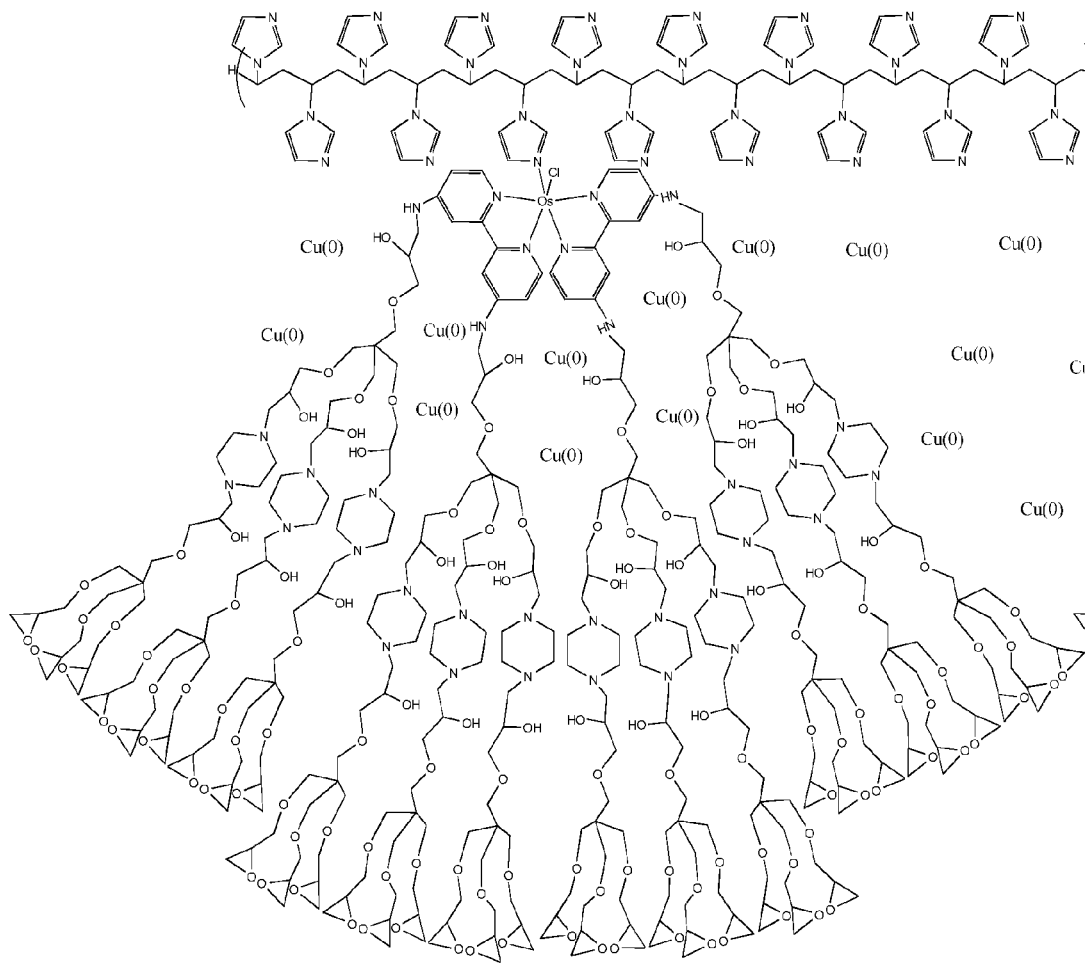

The above chemical structure illustrates one dendron molecule as attached to the core and as enlarged from the immediately preceding backbone chemical structure.

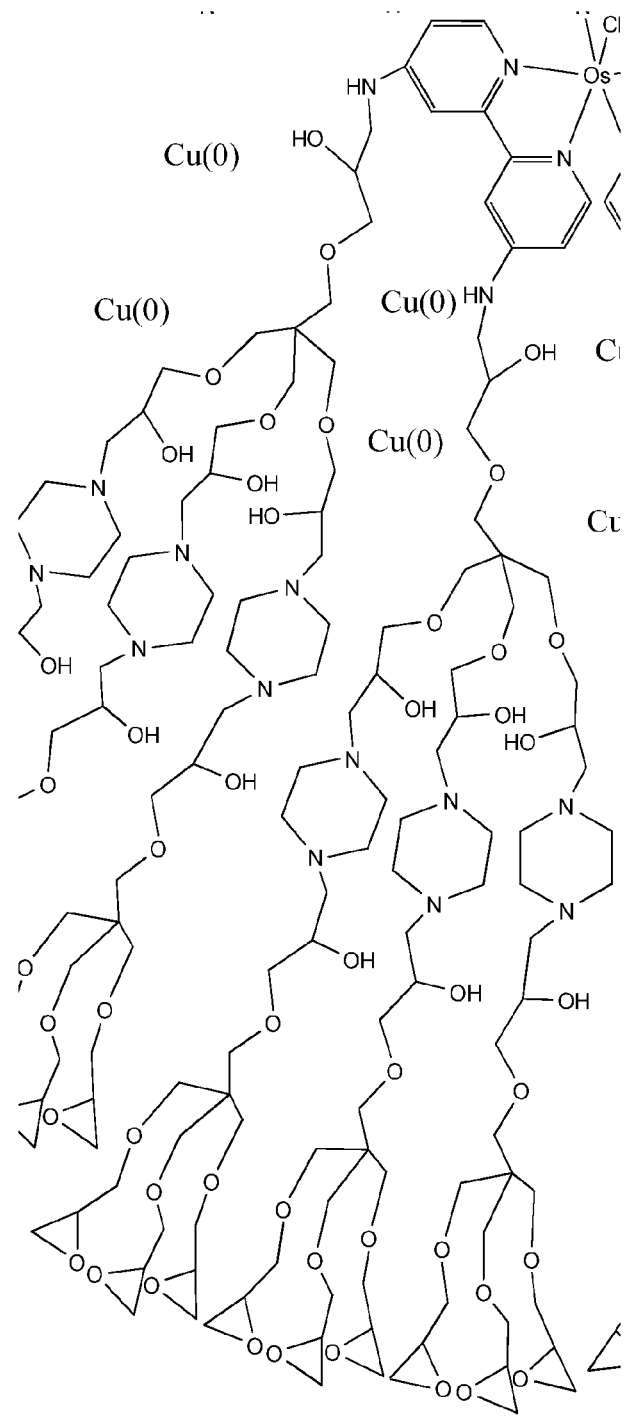

The above chemical structure illustrates one arm of one of the dendron molecules as attached to the core and as enlarged from the immediately preceding dendron chemical structure.

In a round bottom flask, Example Anode Polymer G2 Dendrimer+copper 2+((0.0038 mmol), made from Example 15, a) was dissolved in DI water as a BNPC stock solution. The reducing agent hydrazine monohydrate (0.1 mL, 99%) was mixed with 0.1 mL of water. Then the hydrazine solution was then slowly added to form the copper(0) nanoparticles inside the BNPC.

Color change results were consistent with encapsulation of copper and reduction to Cu(0). For example the color of the Anode Polymer G2 Dendrimer was faint orange. This color changed to bluish-orange after the addition of the Cu(2+). After the addition of hydrazine and filtration of the solution, the color became very dark orange with a blue hue.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A bio-nano power cell (BNPC) which comprises:

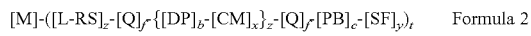
    Formula 2 wherein:
  [M] is an iron, cobalt, ruthenium, osmium, or vanadium metal ion;
  [L-RS] means a ligand or groups of ligands, including monodentate, bidentate, and tridentate ligands as shown by the following Formula 1:

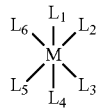
    Formula 1 wherein:
  $L_1, L_2, L_3, L_4, L_5, L_6$, collectively [L], means the same or different ligand that is bound or associated with the metal [M] and is any organic or inorganic moiety that can associate with [M]; and provided that at least one [L] have at its end terminus a reactive site [RS];
  z is independently from 1 to 6;
  [Q] means a linker moiety having at least 2 reactive sites and if more than 1 [Q] is present, they may be the same or different moieties;
  f is independently 0 or from 1 to the number of [RS];
  [DP] means Dendritic Polymer having the ability to react with [RS] and the number of generations, G, of [DP], where G=from 1.0 to the de Gennes dense packing of the surface or N-SIS effects; the surface groups on the [DP] are biocompatible or can react with biocompatible surface groups such that the entire BNPC is biocompatible;
  b is independently from 1 to at least the number of [L-RS] present;
  [CM] means carried material;
  x means 0 or an integer from 1 to 4000;
  [PB] means polymer backbone;
  c is independently from 1 to 6;
  [SF] means the surface functionality groups that can either react with or associate with an enzyme, analyte, biocompatible group, cross-linking group, or [CM], or be inert, provided that the entire BNPC is biocompatible and anti-biofouling;
  y means from 1 to the total number of possible surface groups available, and if greater than 1 may be the same or different moiety; and
  t is from 1 to 6, provided that when t is less than 6, the other available sites on [M] are [L], H, F, Cl, Br, I, CN, SCN, OH, $H_2O$, $NH_3$, alkylamine, dialkylamine, trialkylamine, alkoxy, heterocyclic compounds or polymer backbones that do not have reactive sites; and
  provided that for at least one entity where t is 1 or more, all z are at least 1.

2. The BNPC of claim 1 wherein [M], [L-RS], [Q], [DP], [CM], [PB] and [SF] of Formula 2 can appear in the structure in any order so long as they are bound to at least one other moiety in Formula 2 and one moiety is bound to [M].

3. The BNPC of claim 1 wherein z=5 for [L-RS], f=0 or 1; x=0; and b=4, 5 or 6.

4. The BNPC of claim 1 wherein z=4 for [L-RS], f=0, c=1; x=0, and b=4.

5. The BNPC of claim 1 wherein [L-RS] is PyMIM, BiPyDA, BiPyDADme, BiPyDAE, BiPyDCBOA4, BiPyDCBOX, BiPyDCHMDA, BiPyDCPIPZ, BiPyDCTMDA, BiPyDDEDAOP, BiPyDTMDA or BiPyDHMDA.

6. The BNPC of claim 1 wherein [M] is osmium.

7. The BNPC of claim 1 wherein [Q] is DDEDA, DETA, HMDA, TREN, EDA, PMDA or PIPZ.

8. The BNPC of claim 1 wherein [DP] is PETGE, PETriGE, PETAE or PETAZ.

9. The BNPC of claim 1 wherein [PB] is PVI, PVIPVA, PVPBAc, PVPCEA, PVPCTREN or PVPy.

10. The BNPC of claim 1 wherein [SF] is DEIDA or [CM].

11. The BNPC of claim 1 wherein [SF] is an enzyme.

12. A bio-nano power cell (BNPC) which comprises:

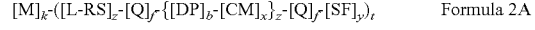
    Formula 2A wherein:
  [M] is an iron, cobalt, ruthenium, osmium, or vanadium metal ion;
  k means an integer of 2 where [M] can be the same or different metal ions;
  [L-RS] means a ligand or groups of ligands, including monodentate, bidentate, and tridentate ligands as shown by the following Formula 1:

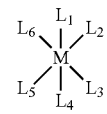
    Formula 1 wherein:
  $L_1, L_2, L_3, L_4, L_5, L_6$, collectively [L], means the same or different ligand that is bound or associated with the metal [M] and is any organic or inorganic moiety that can associate with [M]; and provided that at least one [L] have at its end terminus a reactive site [RS];
  z is independently from 1 to 6;
  [Q] means a linker moiety having at least 2 reactive sites and if more than 1 [Q] is present, they may be the same or different moieties;
  f is independently 0 or from 1 to the number of [RS];
  [DP] means Dendritic Polymer having the ability to react with [RS] and the number of generations, G, of [DP], where G=from 1.0 to the de Gennes dense packing of the surface or N-SIS effects; preferably the surface groups on the [DP] are biocompatible;

b is independently from 1 to at least the number of [L-RS] present;

[CM] means carried material;

x means 0 or an integer from 1 to 4000;

[SF] means the surface functionality groups that can either react with or associate with an enzyme, analyte, cross-linking group, [CM], or be inert;

y means from 1 to the total number of possible surface groups available, and if greater than 1 may be the same or different moiety; and t is from 1 to 6, provided that when t is less than 6, the other available sites on [M] are [L], H, F, Cl, Br, I, CN, SCN, OH, $H_2O$, $NH_3$, alkylamine, dialkylamine, trialkylamine, alkoxy, or heterocyclic compounds; and provided that for at least one entity where t is 1 or more, all z are at least 1.

13. The BNPC of claim 12 wherein [M], [L-RS], [Q], [DP], [CM] and [SF] of Formula 2A can appear in the structure any order so long as they are bound to at least one other moiety in Formula 2A and one moiety is bound to [M], and configured such that an anode and a cathode are present.

14. The BNPC of claim 12 wherein t=6.

15. The BNPC of claim 14 wherein z=6 for [L-RS].

16. The BNPC of claim 15 wherein f=0 or 1.

17. The BNPC of claim 12 wherein z=5 for [L-RS], f=0 or 1; and b=5.

18. The BNPC of claim 12 wherein z=4 for [L-RS], f=0 or 1; and b=4.

19. The BNPC of claim 12 wherein z=3 for [L-RS], f=0 or 1; and b=3.

20. The BNPC of claim 12 wherein z=2 for [L-RS], f=0 or 1; and b=2.

21. The BNPC of claim 12 wherein [L-RS] is PyMIM, BiPyDA, BiPyDADme, BiPyDAE, BiPyDCBOA4, BiPyDCBOX, BiPyDCHMDA, BiPyDCPIPZ, BiPyDCTMDA, BiPyDDEDAOP, BiPyDTMDA or BiPyDHMDA.

22. The BNPC of claim 12 wherein [M] is osmium.

23. The BNPC of claim 12 wherein [Q] is DDEDA, DETA, HMDA, TREN, EDA, PMDA or PIPZ.

24. The BNPC of claim 12 wherein [DP] is PETGE, PETriGE, DO3A, DOTA, PETAE or PETAZ.

25. The BNPC of claim 12 wherein [SF] is DEIDA or [CM].

26. The BNPC of claim 12 wherein [M], [L-RS], [Q], [DP], and [SF] of Formula 2A can appear in the structure in any order so long as they are bound to at least one other moiety in Formula 2A and one moiety is bound to [M].

27. The BNPC of claim 12 wherein [SF] is an enzyme that electrooxidizes an anode reductant.

28. The BNPC of claim 12 wherein [SF] is an enzyme that electroreduces a cathode oxidant.

\* \* \* \* \*